US009029450B2

(12) United States Patent
Albert et al.

(10) Patent No.: US 9,029,450 B2
(45) Date of Patent: *May 12, 2015

(54) MIXTURES OF SILICON-CONTAINING COUPLING REAGENTS

(75) Inventors: Philipp Albert, Lörrach (DE); Manuel Friedel, Zürich (CH); Karsten Korth, Grenzach-Wyhlen (DE); Andre Hasse, Linnich-Ederen (DE); Oliver Klockmann, Niederzier (DE)

(73) Assignee: Evonik Degussa GmbH, Essen (DE)

( * ) Notice: Subject to any disclaimer, the term of this patent is extended or adjusted under 35 U.S.C. 154(b) by 677 days.

This patent is subject to a terminal disclaimer.

(21) Appl. No.: 12/309,703

(22) PCT Filed: Jun. 11, 2007

(86) PCT No.: PCT/EP2007/055711
§ 371 (c)(1),
(2), (4) Date: Jan. 27, 2009

(87) PCT Pub. No.: WO2008/009514
PCT Pub. Date: Jan. 24, 2008

(65) Prior Publication Data
US 2011/0034584 A1    Feb. 10, 2011

(30) Foreign Application Priority Data
Jul. 17, 2006 (DE) .......................... 10 2006 033 310

(51) Int. Cl.
*B60C 1/00* (2006.01)
*C07F 7/18* (2006.01)
*C08K 5/548* (2006.01)

(52) U.S. Cl.
CPC ............... *B60C 1/0016* (2013.01); *C07F 7/18* (2013.01); *C08K 5/548* (2013.01)

(58) Field of Classification Search
USPC ............................ 524/262; 556/427, 428, 429
See application file for complete search history.

(56) References Cited

U.S. PATENT DOCUMENTS

| 6,197,105 B1 | 3/2001 | Freeman et al. | |
| 2003/0229166 A1* | 12/2003 | Krafczyk et al. | 524/261 |
| 2006/0052622 A1* | 3/2006 | Korth et al. | 556/437 |
| 2006/0161015 A1* | 7/2006 | Klockmann et al. | 556/427 |

FOREIGN PATENT DOCUMENTS

| DE | 1163820 B | 2/1964 |
| EP | 1285926 A1 | 2/2003 |
| EP | 1637535 A1 | 3/2006 |
| EP | 1672017 A2 | 6/2006 |
| EP | 1683801 A2 | 7/2006 |

OTHER PUBLICATIONS

Plueddemann, E.P., Silane Coupling Agents, 2nd Ed., Plenum Press, 1982.*
International Preliminary Report on Patentability Along with the English Translation for PCT/EP2007/055711 (Jan. 20, 2009).

* cited by examiner

*Primary Examiner* — Vickey Nerangis
(74) *Attorney, Agent, or Firm* — Smith, Gambrell & Russell, LLP

(57) ABSTRACT

Mixtures of silicon-containing coupling reagents comprising (mercaptoorganyl)alkylpolyethersilanes containing silanol groups and (mercaptoorganyl)alkylpolyethersilanes free of silanol groups in a weight ratio of from 5:95 to 95:5. The mixtures can be prepared by transesterification and hydrolysis. The mixtures can be used in rubber mixtures.

12 Claims, No Drawings

MIXTURES OF SILICON-CONTAINING COUPLING REAGENTS

INTRODUCTION AND BACKGROUND

The invention relates to mixtures composed of silicon-containing coupling reagents, processes for their production, and also their use.

It is known that silanes can be used as coupling agents. By way of example, aminoalkyltrialkoxysilanes, methacryloxy-alkyltrialkoxysilanes, polysulfanealkyltrialkoxysilanes, and mercaptoalkyltrialkoxysilanes (E. P. Plueddemann, "Silane Coupling Agents", 2nd edn. Plenum Press 1982) are used as coupling agents between inorganic materials and organic polymers, as crosslinking agents, and as surface modifiers.

These coupling agents or bonding agents form bonds both to the filler and to the elastomer, thus bringing about good interaction between the filler surface and the elastomer.

It is moreover known that the use of commercially available silane coupling agents (DE 22 55 577) having three alkoxy substituents on the silicon atom leads to liberation of considerable amounts of alcohol during and after binding to the filler. Since trimethoxy- and triethoxy-substituted silanes are generally used, considerable amounts of the corresponding alcohols—methanol and ethanol—are liberated (Berkemeier, D.; Hader, W.; Rinker, M.; Heiss, G. Mixing of silica compounds from the viewpoint of a manufacturer of internal mixers. Gummi, Fasern, Kunststoffe (2001), 54(1), 17-22).

It is moreover known that methoxy- and ethoxy-substituted silanes are more reactive than the corresponding long-chain alkoxy-substituted silanes, and therefore can bind more rapidly to the filler, and for technical and economic reasons it has therefore been impossible hitherto to forgo the use of methoxy and ethoxy substituents. DE 10137890, JP 62-181346, De 3426987, and EP 0085831 disclose various mercaptosilanes.

DE 102005032658.7 moreover discloses polyether-substituted mercaptosilanes. These silanes are synthesized by reacting alkoxysilanes with an alkoxylated alcohol, with catalysis.

DE 102005052233 discloses a process for the production of organosilanes by reaction of (haloorganyl)alkoxysilanes with hydrous sulfurization reagents.

JP 2005232354 moreover discloses the use of mercaptosilanes with partial esters of maleic anhydride with (poly)oxypropylene derivatives in rubber mixtures.

EP 1672017 discloses rubber mixtures comprising rubber, fillers, if appropriate further rubber auxiliaries, and at least one mercaptosilane.

Disadvantages of the known alkoxy-substituted and/or alkylpolyether-substituted mercaptosilanes having long-chain alkoxy groups, when used in rubber mixtures, are poor processing properties and/or dynamic properties accompanied by reduced alcohol emission or good processing properties and/or dynamic properties accompanied by increased alcohol emission.

It is an object of the present invention to provide coupling reagents which in filler-reinforced rubber mixtures lead to at least identical processing properties and/or at least identical dynamic properties in comparison with known coupling reagents, e.g. alkylpolyether-alcohol-substituted mercaptoorganylsilanes, where this is accompanied by reduced alcohol emission.

SUMMARY OF THE INVENTION

The invention provides mixtures composed of silicon-containing coupling reagents, characterized in that these comprise (mercaptoorganyl)alkylpolyethersilanes containing silanol groups and (mercaptoorganyl)alkylpolyethersilanes free from silanol groups in a ratio by weight of from 5:95 to 95:5, preferably of from 8:92 to 92:8, particularly preferably from 12:88 to 88:12, very particularly preferably from 17:83 to 85:15, and extremely preferably from 25:75 to 75:25.

(Mercaptoorganyl)alkylpolyethersilanes containing silanol groups can be compounds of the general formula I

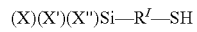

where independently of one another

X is an alkylpolyether group O—$((CR^{II}_2)_w$—O—$)_v$ Alk, preferably O—$(CH_2$—$CH_2$—O—$)_v$ Alk, or O—$(CH(CH_3)$—$CH_2$—O—$)_v$ Alk, v=from 1 to 40, preferably from 2 to 30, particularly preferably from 3 to 25, very particularly preferably from 4 to 20, extremely preferably from 5 to 16, w=from 1 to 40, preferably from 2 to 30, particularly preferably from 2 to 20, very particularly preferably from 3 to 10, $R^{II}$, independently of one another, is H, a phenyl group, or an unbranched or branched alkyl group, preferably a $C_1$-$C_{11}$-alkyl group, particularly preferably a $CH_3$— or $CH_2$—$CH_3$-group, Alk is a branched or unbranched, saturated or unsaturated, substituted or unsubstituted, aliphatic, aromatic, or mixed aliphatic/aromatic monovalent $C_1$-$C_{35}$—, preferably $C_2$-$C_{22}$—, particularly preferably $C_3$-$C_{18}$—, very particularly preferably $C_4$-$C_{13}$—, extremely preferably $C_6$-$C_{10}$—, hydrocarbon group, X' is branched or unbranched alkyl, preferably $C_1$-$C_{18}$-alkyl, particularly preferably $CH_3$, $CH_2$—$CH_3$, $CH(CH_3)$—$CH_3$, $CH_2$—$CH_2$—$CH_3$, or $C_4$-$C_{18}$-alkyl, branched or unbranched alkoxy, preferably $C_1$-$C_{18}$-alkoxy, particularly preferably —$OCH_3$, —$OCH_2$—$CH_3$, —$OCH(CH_3)$—$CH_3$, —$OCH_2$—$CH_2$—$CH_3$, —$OC_{12}H_{25}$, —$OC_{13}H_{27}$, —$OC_{14}H_{29}$, or $C_{15}$-$C_{18}$-alkoxy, branched or unbranched $C_2$-$C_{25}$-alkenyloxy, preferably $C_4$-$C_{20}$-alkenyloxy, particularly preferably $C_6$-$C_{18}$-alkenyloxy, a $C_6$-$C_{35}$-aryloxy group, preferably $C_9$-$C_{30}$-aryloxy, particularly preferably phenyloxy (—$OC_6H_5$) or $C_9$-$C_{18}$-aryloxy, a branched or unbranched $C_7$-$C_{35}$-alkylaryloxy group, preferably $C_9$-$C_{30}$-alkylaryloxy group, particularly preferably benzyloxy, (—O—$CH_2$—$C_6H_5$) or —O—$CH_2$—$CH_2$—$C_5H_5$, a branched or unbranched $C_7$-$C_{35}$-aralkyloxy group, preferably $C_7$-$C_{25}$-aralkyloxy group, particularly preferably tolyloxy (—O—$C_6H_4$—$CH_3$) or a $C_9$-$C_{18}$-aralkyloxy group, an X, or a hydroxy group (—OH), X" is a hydroxy group (—OH), and $R^I$ is a branched or unbranched, saturated or unsaturated, aliphatic, aromatic or mixed aliphatic/aromatic divalent $C_1$-$C_{30}$-hydrocarbon group, optionally having substitution.

DETAILED DESCRIPTION OF THE INVENTION

The mixtures composed of silicon-containing coupling reagents can comprise >5% by weight, preferably >25% by weight, particularly preferably >40% by weight, very particularly preferably >70% by weight, extremely preferably >90% by weight, of (mercaptoorganyl)alkylpolyethersilanes containing silanol groups and (mercaptoorganyl)alkylpolyethersilanes free from silanol groups.

The mixtures composed of silicon-containing coupling reagents can consist essentially of (mercaptoorganyl)alkylpolyethersilanes containing silanol groups and (mercaptoorganyl)alkylpolyethersilanes free from silanol groups.

(Mercaptoorganyl)alkylpolyethersilanes free from silanol groups can be compounds of the general formula II

where, independently of one another, X and $R^I$ are defined as above, and X''', independently of one another, is branched or unbranched alkyl, preferably $C_1$-$C_{18}$-alkyl, particularly preferably $CH_3$, $CH_2$—$CH_3$, $CH(CH_3)$—$CH_3$, $CH_2$—$CH_2$—$CH_3$, or $C_4$-$C_{18}$-alkyl, branched or unbranched alkoxy, preferably $C_1$-$C_{18}$-alkoxy, particularly preferably —$OCH_3$, —$OCH_2$—$CH_3$, —$OCH(CH_3)$—$CH_3$, —$OCH_2$—$CH_2$—$CH_3$, —$OC_{12}H_{25}$, —$OC_{13}H_{27}$, —$OC_{14}H_{29}$, or $C_{15}$-$C_{18}$-alkoxy, branched or unbranched $C_2$-$C_{25}$-alkenyloxy, preferably $C_4$-$C_{20}$-alkenyloxy, particularly preferably $C_6$-$C_{18}$-alkenyloxy, $C_6$-$C_{35}$-aryloxy, preferably $C_6$-$C_{30}$-aryloxy, particularly preferably phenyloxy (—$OC_6H_5$) or $C_9$-$C_{18}$-aryloxy, a branched or unbranched $C_7$-$C_{35}$-alkylaryloxy group, preferably $C_9$-$C_{30}$-alkylaryloxy group, particularly preferably benzyloxy, (—O—$CH_2$—$C_6H_5$) or —O—$CH_2$—$CH_2$—$C_6H_5$, a branched or unbranched $C_7$-$C_{35}$-aralkyloxy group, preferably $C_7$-$C_{25}$-aralkyloxy group, particularly preferably tolyloxy (—O—$C_6H_4$—$CH_3$) or a $C_9$-$C_{18}$-aralkyloxy group, or an X.

The group $((CR^{II}_2)_w$—O—$)$ can be ethylene oxide units ($CH_2$—$CH_2$—O), propylene oxide units, for example ($CH(CH_3)$—$CH_2$—O) or ($CH_2$—$CH(CH_3)$—O), or butylene oxide units, for example (—$CH_2$—$CH_2$—$CH_2$—$CH_2$—O), (—$CH(CH_2$—$CH_3)$—$CH_2$—O) or (—$CH_2$—$CH(CH_2$—$CH_3)$—O)

The group O—$(CR^{II}_2$—$CR^{II}_2$—O$)_v$ can preferably be:
O—(—$CH_2$—$CH_2$—O—$)_a$,
O—(—$CH(CH_3)$—$CH_2$—O—$)_a$,
O—(—$CH_2$—$CH(CH_3)$—O—$)_a$,
O—(—$CH_2$—$CH_2$—O—$)_a$(—$CH(CH_3)$—$CH_2$—O—),
O—(—$CH_2$—$CH_2$—O—)(—$CH(CH_3)$—$CH_2$—O—$)_a$,
O—(—$CH_2$—$CH_2$—O—$)_a$(—$CH_2$—$CH(CH_3$—O—),
O—(—$CH_2$—$CH_2$—O—)(—$CH_2$—$CH(CH_3)$—O—$)_a$,
O—(—$CH(CH_3)$—$CH_2$—O—$)_a$(—$CH_2$—$CH(CH_3)$—O—),
O—(—$CH(CH_3)$—$CH_2$—O—) (—$CH_2$—$CH(CH_3)$—O—$)_a$,
O—(—$CH_2$—$CH_2$—O—$)_a$(—$CH(CH_3)$—$CH_2$—O—$)_b$(—$CH_2$—$CH(CH_3)$—O—$)_c$, or a mutual combination,
where a+b+c=v.

The indices a, b, and c are whole numbers, and designate the number of repeat units.

The alkylpolyether group X using —O($CR^{II}_2$—$CR^{II}_2$—O$)_v$-Alk can be
O—($CH_2$—$CH_2$O$)_2$—$C_3H_7$, O—($CH_2$—$CH_2$O$)_3$—$C_3H_7$, O—($CH_2$—$CH_2$O$)_4$—$C_3H_7$, O—($CH_2$—$CH_2$O$)_5$—$C_3H_7$, O—($CH_2$—$CH_2$O$)_6$—$C_3H_7$, O—($CH_2$—$CH_2$O$)_7$—$C_3H_7$, O—($CH(CH_3)$—$CH_2$O$)_2$—$C_3H_7$, O—($CH(CH_3)$—$CH_2$O$)_3$—$C_3H_7$, O—($CH(CH_3)$—$CH_2$O$)_4$—$C_3H_7$, O—($CH(CH_3)$—$CH_2$O$)_5$—$C_3H_7$, O—($CH(CH_3)$—$CH_2$O$)_6$—$C_3H_7$,
O—($CH_2$—$CH_2$O$)_2$—$C_4H_9$, O—($CH_2$—$CH_2$O$)_3$—$C_4H_9$, O—($CH_2$—$CH_2$O$)_4$—$C_4H_9$, O—($CH_2$—$CH_2$O$)_5$—$C_4H_9$, O—($CH_2$—$CH_2$O$)_6$—$C_4H_9$, O—($CH_2$—$CH_2$O$)_7$—$C_4H_9$, O—($CH(CH_3)$—($CH_2$O$)_2$—$C_4H_9$, O—($CH(CH_3)$—$CH_2$O$)_3$—$C_4H_9$, O—($CH(CH_3)$—$CH_2$O$)_4$—$C_4H_9$, O—($CH(CH_3)$—$CH_2$O$)_5$—$C_4H_9$, O—($CH(CH_3)$—$CH_2$O$)_6$—$C_4H_9$,
O—($CH_2$—$CH_2$O$)_2$—$C_5H_{11}$, O—($CH_2$—$CH_2$O$)_3$—$C_5H_{11}$, O—($CH_2$—$CH_2$O$)_4$—$C_5H_{11}$, O—($CH_2$—$CH_2$O$)_5$—$C_5H_{11}$, O—($CH_2$—$CH_2$O$)_6$—$C_5H_{11}$, O—($CH_2$—$CH_2$O$)_7$—$C_5H_{11}$, O—($CH(CH_3)$—$CH_2$O$)_2$—$C_5H_{11}$, O—($CH(CH_3)$—$CH_2$O$)_3$—$C_5H_{11}$, O—($CH(CH_3)$—$CH_2$O$)_4$—$C_5H_{11}$, O—($CH(CH_3)$—$CH_2$O$)_5$—$C_5H_{11}$, O—($CH(CH_3)$—$CH_2$O$)_6$—$C_5H_{11}$,
O—($CH_2$—$CH_2$O$)_2$—$C_6H_{13}$, O—($CH_2$—$CH_2$O$)_3$—$C_6H_{13}$, O—($CH_2$—$CH_2$O$)_4$—$C_6H_{13}$, O—($CH_2$—$CH_2$O$)_5$—$C_6H_{13}$, O—($CH_2$—$CH_2$O$)_6$—$C_6H_{13}$, O—($CH_2$—$CH_2$O$)_7$—$C_6H_{13}$, O—($CH(CH_3)$—$CH_2$O$)_2$—$C_6H_{13}$, O—($CH(CH_3)$—$CH_2$O$)_3$—$C_6H_{13}$, O—($CH(CH_3)$—$CH_2$O$)_4$—$C_6H_{13}$, O—($CH(CH_3)$—$CH_2$O$)_5$—$C_6H_{13}$, O—($CH(CH_3)$—$CH_2$O$)_6$—$C_6H_{13}$,
O—($CH_2$—$CH_2$O$)_2$—$C_7H_{15}$, O—($CH_2$—$CH_2$O$)_3$—$C_7H_{15}$, O—($CH_2$—$CH_2$O$)_4$—$C_7H_{15}$, O—($CH_2$—$CH_2$O$)_5$—$C_7H_{15}$, O—($CH_2$—$CH_2$O$)_6$—$C_7H_{15}$, O—($CH_2$—$CH_2$O$)_7$—$C_7H_{15}$, O—($CH(CH_3)$—$CH_2$O$)_2$—$C_7H_{15}$, O—($CH(CH_3)$—$CH_2$O$)_3$—$C_7H_{15}$, O—($CH(CH_3)$—$CH_2$O$)_4$—$C_7H_{15}$, O—($CH(CH_3)$—$CH_2$O$)_5$—$C_7H_{15}$, O—($CH(CH_3)$—$CH_2$O$)_6$—$C_7H_{15}$,
O—($CH_2$—$CH_2$O$)_2$—$C_8H_{17}$, O—($CH_2$—$CH_2$O$)_3$—$C_8H_{17}$, O—($CH_2$—$CH_2$O$)_4$—$C_8H_{17}$, O—($CH_2$—$CH_2$O$)_5$—$C_8H_{17}$, O—($CH_2$—$CH_2$O$)_6$—$C_8H_{17}$, O—($CH_2$—$CH_2$O$)_7$—$C_8H_{17}$, O—($CH(CH_3)$—$CH_2$O$)_2$—$C_8H_{17}$, O—($CH(CH_3)$—$CH_2$O$)_3$—$C_8H_{17}$, O—($CH(CH_3)$—$CH_2$O$)_4$—$C_8H_{17}$, O—($CH(CH_3)$—$CH_2$O$)_5$—$C_8H_{17}$, O—($CH(CH_3)$—$CH_2$O$)_6$—$C_8H_{17}$,
O—($CH_2$—$CH_2$O$)_2$—$C_9H_{19}$, O—($CH_2$—$CH_2$O$)_3$—$C_9H_{19}$, O—($CH_2$—$CH_2$O$)_4$—$C_9H_{19}$, O—($CH_2$—$CH_2$O$)_5$—$C_9H_{19}$, O—($CH_2$—$CH_2$O$)_6$—$C_9H_{19}$, O—($CH_2$—$CH_2$O$)_7$—$C_9H_{19}$, O—($CH(CH_3)$—$CH_2$O$)_2$—$C_9H_{19}$, O—($CH(CH_3)$—$CH_2$O$)_3$—$C_9H_{19}$, O—($CH(CH_3)$—$CH_2$O$)_4$—$C_9H_{19}$, O—($CH(CH_3)$—$CH_2$O$)_5$—$C_9H_{19}$, O—($CH(CH_3)$—$CH_2$O$)_6$—$C_9H_{19}$,
O—($CH_2$—$CH_2$O$)_2$—$C_{10}H_{21}$, O—($CH_2$—$CH_2$O$)_3$—$C_{10}H_{21}$, O—($CH_2$—$CH_2$O$)_4$—$C_{10}H_{21}$, O—($CH_2$—$CH_2$O$)_5$—$C_{10}H_{21}$, O—($CH_2$—$CH_2$O$)_6$—$C_{10}H_{21}$, O—($CH_2$—$CH_2$O$)_7$—$C_{10}H_{21}$, O—($CH(CH_3)$—$CH_2$O$)_2$—$C_{10}H_{21}$, O—($CH(CH_3)$—$CH_2$O$)_3$—$C_{10}H_{21}$, O—($CH(CH_3)$—$CH_2$O$)_4$—$C_{10}H_{21}$, O—($CH(CH_3)$—$CH_2$O$)_5$—$C_{10}H_{21}$, O—($CH(CH_3)$—$CH_2$O$)_6$—$C_{10}H_{21}$,
O—($CH_2$—$CH_2$O$)_2$—$C_{11}H_{23}$, O—($CH_2$—$CH_2$O$)_3$—$C_{11}H_{23}$, O—($CH_2$—$CH_2$O$)_4$—$C_{11}H_{23}$, O—($CH_2$—$CH_2$O$)_5$—$C_{11}H_{23}$, O—($CH_2$—$CH_2$O$)_6$—$C_{11}H_{23}$, O—($CH_2$—$CH_2$O$)_7$—$C_{11}H_{23}$, O—($CH(CH_3)$—$CH_2$O$)_2$—$C_{11}H_{23}$, O—($CH(CH_3)$—$CH_2$O$)_3$—$C_{11}H_{23}$, O—($CH(CH_3)$—$CH_2$O$)_4$—$C_{11}H_{23}$, O—($CH(CH_3)$—$CH_2$O$)_5$—$C_{11}H_{23}$, O—($CH(CH_3)$—$CH_2$O$)_6$—$C_{11}H_{23}$,
O—($CH_2$—$CH_2$O$)_2$—$C_{12}H_{25}$, O—($CH_2$—$CH_2$O$)_3$—$C_{12}H_{25}$, O—($CH_2$—$CH_2$O$)_4$—$C_{12}H_{25}$, O—($CH_2$—$CH_2$O$)_5$—$C_{12}H_{25}$, O—($CH_2$—$CH_2$O$)_6$—$C_{12}H_{25}$, O—($CH_2$—$CH_2$O$)_7$—$C_{12}H_{25}$, O—($CH(CH_3)$—$CH_2$O$)_2$—$C_{12}H_{25}$, O—($CH(CH_3)$—$CH_2$O$)_3$—$C_{12}H_{25}$, O—($CH(CH_3)$—$CH_2$O$)_4$—$C_{12}H_{25}$, O—($CH(CH_3)$—$CH_2$O$)_5$—$C_{12}H_{25}$,
O—($CH_2$—$CH_2$O$)_2$—$C_{13}H_{27}$, O—($CH_2$—$CH_2$O$)_3$—$C_{13}H_{27}$, O—($CH_2$—$CH_2$O$)_4$—$C_{13}H_{27}$, O—($CH_2$—$CH_2$O$)_5$—$C_{13}H_{27}$, O—($CH_2$—$CH_2$O$)_6$—$C_{13}H_{27}$, O—($CH_2$—$CH_2$O$)_7$—$C_{13}H_{27}$, O—($CH(CH_3)$—$CH_2$O$)_2$—$C_{13}H_{27}$, O—($CH(CH_3)$—$CH_2$O$)_3$—$C_{13}H_{27}$, O—($CH(CH_3)$—$CH_2$O$)_4$—$C_{13}H_{27}$, O—($CH(CH_3)$—$CH_2$O$)_5$—$C_{13}H_{27}$,
O—($CH_2$—$CH_2$O$)_2$—$C_{14}H_{29}$, O—($CH_2$—$CH_2$O$)_3$—$C_{14}H_{29}$, O—($CH_2$—$CH_2$O$)_4$—$C_{14}H_{29}$, O—($CH_2$—$CH_2$O$)_5$—$C_{14}H_{29}$, O—($CH_2$—$CH_2$O$)_6$—$C_{14}H_{29}$, O—($CH_2$—$CH_2$O$)_7$—$C_{14}H_{29}$, O—($CH(CH_3)$—$CH_2$O$)_2$—$C_{14}H_{29}$, O—($CH(CH_3)$—$CH_2$O$)_3$—$C_{14}H_{29}$, O—($CH(CH_3)$—$CH_2$O$)_4$—$C_{14}H_{29}$, O—($CH(CH_3)$—$CH_2$O$)_5$—$C_{14}H_{29}$,
O—($CH_2$—$CH_2$O$)_2$—$C_{15}H_{31}$, O—($CH_2$—$CH_2$O)$, O—($CH_2$—$CH_2$O$)_4$—$C_{15}H_{31}$, O—($CH_2$—$CH_2$O$)_5$—$C_{15}H_{31}$, O—($CH_2$—$CH_2$O$)_6$—$C_{15}H_{31}$, O—($CH_2$—$CH_2$O$)_7$—$C_{15}H_{31}$, O—($CH(CH_3)$—$CH_2$O), O—($CH(CH_3)$—$CH_2$O$)_3$—$C_{15}H_{31}$, O—($CH(CH_3)$—$CH_2$O$)_4$—$C_{15}H_{31}$,
O—($CH_2$—$CH_2$O$)_2$—$C_{16}H_{33}$, O—($CH_2$—$CH_2$O$)_3$—$C_{16}H_{33}$, O—($CH_2$—$CH_2$O$)_4$—$C_{16}H_{33}$, O—($CH_2$—$CH_2$O$)_5$—$C_{16}H_{33}$, O—($CH_2$—$CH_2$O$)_6$—$C_{16}H_{33}$, O—($CH(CH_3)$—$CH_2$O$)_2$—$C_{16}H_{33}$, O—($CH(CH_3)$—$CH_2$O$)_3$—$C_{16}H_{33}$, O—($CH(CH_3)$—$CH_2$O$)_4$—$C_{16}H_{33}$, O—(CH$_2$—CH$_2$O)$_2$—C$_{17}$H$_{35}$, O—(CH$_2$—CH$_2$O)$_3$—C$_{17}$H$_{35}$, O—(CH$_2$—CH$_2$O)$_4$—C$_{17}$H$_{35}$, O—(CH$_2$—CH$_2$O)$_5$—C$_{17}$H$_{35}$, O—(CH$_2$—CH$_2$O)$_6$—C$_{17}$H$_{35}$, O—(CH(CH$_3$)—CH$_2$O)$_2$—C$_{17}$H$_{35}$, O—(CH(CH$_3$)—CH$_2$O)$_3$—C$_{17}$H$_{35}$, O—(CH(CH$_3$)—CH$_2$O)$_4$—C$_{17}$H$_{35}$,
O—(CH$_2$—CH$_2$O)$_2$—C$_{18}$H$_{37}$, O—(CH$_2$—CH$_2$O)$_3$—C$_{18}$H$_{37}$, O—(CH$_2$—CH$_2$O)$_4$—C$_{18}$H$_{37}$, O—(CH$_2$—CH$_2$O)$_5$—C$_{18}$H$_{37}$, O—(CH(CH$_3$)—CH$_2$O)$_2$—C$_{18}$H$_{37}$, O—(CH(CH$_3$)—CH$_2$O)$_3$—C$_{18}$H$_{37}$,
O—(CH$_2$—CH$_2$O)$_2$—C$_6$H$_4$—C$_9$H$_{19}$, O—(CH$_2$—CH$_2$O)$_3$—C$_6$H$_4$—C$_9$H$_{19}$, O—(CH$_2$—CH$_2$O)$_4$—C$_6$H$_4$—C$_9$H$_{19}$, O—(CH$_2$—CH$_2$O)$_5$—C$_6$H$_4$—C$_9$H$_{19}$, O—(CH$_2$—CH$_2$O)$_6$—C$_6$H$_4$—C$_9$H$_{19}$, O—(CH$_2$—CH$_2$O)$_7$—C$_6$H$_4$—C$_9$H$_{19}$, O—(CH(CH$_3$)—CH$_2$O)$_2$—C$_6$H$_4$—C$_9$H$_{19}$, O—(CH(CH$_3$)—CH$_2$O)$_3$—C$_6$H$_4$—C$_9$H$_{19}$, or O—(CH(CH$_3$)—CH$_2$O)$_4$—C$_6$H$_4$—C$_9$H$_{19}$.

The alkylpolyether group X using O—(CR$^{II}_2$—CR$^{II}_2$—O)$_v$-Alk can, for v=5, R$^{II}$=H, and Alk equal to C$_{13}$H$_{27}$, be

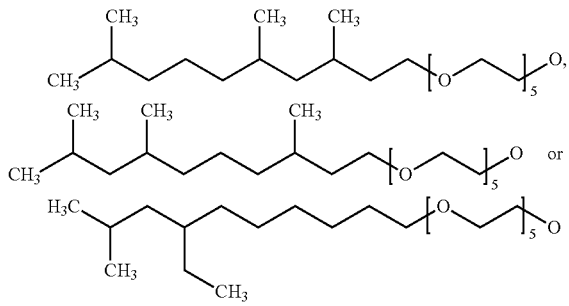

The average branching number of the Alk carbon chain can be from 1 to 5, preferably from 1.2 to 4. The average branching number is defined here as the (number of CH$_3$ groups)-1.

R$^I$ can be —CH$_2$—, —CH$_2$CH$_2$—, —CH$_2$CH$_2$CH$_2$—, —CH$_2$CH$_2$CH$_2$CH$_2$—CH(CH$_3$)—, —CH$_2$CH(CH$_3$)—, —CH(CH$_3$)CH$_2$—, —C(CH$_3$)$_2$—, —CH(C$_2$H$_5$)—, —CH$_2$CH$_2$CH(CH$_3$)—, —CH$_2$ (CH$_3$)CH$_2$CH$_2$—, —CH$_2$CH(CH$_3$)CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$—, —CH$_2$CH$_2$CH$_2$CH$_2$CH$_2$ CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$CH$_2$CH$_2$CH$_2$CH$_2$—, or

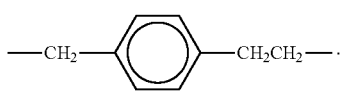

Preferred compounds of the general formula I can be:
[[C$_3$H$_7$O—(CH$_2$—CH$_2$O)$_2$](Me)(HO)Si(CH$_2$)$_3$]—SH,
[[C$_3$H$_7$O—(CH$_2$—CH$_2$O)$_3$](Me)(HO)Si(CH$_2$)$_3$]—SH,
[[C$_3$H$_7$O—(CH$_2$—CH$_2$O)$_4$](Me)(HO)Si(CH$_2$)$_3$]—SH,
[[C$_3$H$_7$O—(CH$_2$—CH$_2$O)$_5$](Me)(Ho)Si(CH$_2$)$_3$]—SH,
[[C$_3$H$_7$O—(CH$_2$—CH$_2$O)$_6$](Me)(HO)Si(CH$_2$)$_3$]—SH,
[[C$_4$H$_9$O—(CH$_2$—CH$_2$O)$_2$](Me)(HO)Si(CH$_2$)$_3$]—SH,
[[C$_4$H$_9$O—(CH$_2$—CH$_2$O)$_3$](Me)(HO)Si(CH$_2$)$_3$]—SH,
[[C$_4$H$_9$O—(CH$_2$—CH$_2$O)$_4$](Me)(HO)Si(CH$_2$)$_3$]—SH,
[[C$_4$H$_9$O—(CH$_2$—CH$_2$O)$_5$](Me)(HO)Si(CH$_2$)$_3$]—SH,
[[C$_4$H$_9$O—(CH$_2$—CH$_2$O)$_6$](Me)(HO)Si(CH$_2$)$_3$]—SH,
[[C$_5$H$_{11}$O—(CH$_2$—CH$_2$O)$_2$](Me)(HO)Si(CH$_2$)$_3$]—SH,
[[C$_5$H$_{11}$O—(CH$_2$—CH$_2$O)$_3$](Me)(HO)Si(CH$_2$)$_3$]—SH,
[[C$_5$H$_{11}$O—(CH$_2$—CH$_2$O)$_4$](Me)(HO)Si(CH$_2$)$_3$]—SH,
[[C$_5$H$_{11}$O—(CH$_2$—CH$_2$O)$_5$](Me)(HO)Si(CH$_2$)$_3$]—SH,
[[C$_5$H$_{11}$O—(CH$_2$—CH$_2$O)$_6$](Me)(HO)Si(CH$_2$)$_3$]—SH,
[[C$_6$H$_{13}$O—(CH$_2$—CH$_2$O)$_2$](Me)(HO)Si(CH$_2$)$_3$]—SH,
[[C$_6$H$_{13}$O—(CH$_2$—CH$_2$O)$_3$](Me)(HO)Si(CH$_2$)$_3$]—SH,
[[C$_6$H$_3$O—(CH$_2$—CH$_2$O)$_4$](Me)(HO)Si(CH$_2$)$_3$]—SH,
[[C$_6$H$_{13}$O—(CH$_2$—CH$_2$O)$_5$](Me)(HO)Si(CH$_2$)$_3$]—SH,
[[C$_6$H$_{13}$O—(CH$_2$—CH$_2$O)$_6$](Me)(HO)Si(CH$_2$)$_3$]—SH,
[[C$_7$H$_{15}$O—(CH$_2$—CH$_2$O)$_2$](Me)(HO)Si(CH$_2$)$_3$]—SH,
[[C$_7$H$_{15}$O—(CH$_2$—CH$_2$O)$_3$](Me)(Ho)Si(CH$_2$)$_3$]—SH,
[[C$_7$H$_{15}$O—(CH$_2$—CH$_2$O)$_4$](Me)(HO)Si(CH$_2$)$_3$]—SH,
[[C$_7$H$_{15}$O—(CH$_2$—CH$_2$O)$_5$](Me)(HO)Si(CH$_2$)$_3$]—SH,
[[C$_7$H$_{15}$O—(CH$_2$—CH$_2$O)$_6$](Me)(HO)Si(CH$_2$)$_3$]—SH,
[[C$_8$H$_{17}$O—(CH$_2$—CH$_2$O)$_2$](Me)(HO)Si(CH$_2$)$_3$]—SH,
[[C$_8$H$_{17}$O—(CH$_2$—CH$_2$O)$_3$](Me)(HO)Si(CH$_2$)$_3$]—SH,
[[C$_8$H$_{17}$O—(CH$_2$—CH$_2$O)$_4$](Me)(HO)Si(CH$_2$)$_3$]—SH,
[[C$_8$H$_{17}$O—(CH$_2$—CH$_2$O)$_5$](Me)(HO)Si(CH$_2$)$_3$]—SH,
[[C$_8$H$_{17}$O—(CH$_2$—CH$_2$O)$_6$](Me)(HO)Si(CH$_2$)$_3$]—SH,
[[C$_9$H$_{19}$O—(CH$_2$—CH$_2$O)$_2$](Me)(HO)Si(CH$_2$)$_3$]—SH,
[[C$_9$H$_{19}$O—(CH$_2$—CH$_2$O)$_3$](Me)(HO)Si(CH$_2$)$_3$]—SH,
[[C$_9$H$_{19}$O—(CH$_2$—CH$_2$O)$_4$](Me)(HO)Si(CH$_2$)$_3$]—SH,
[[C$_9$H$_{19}$O—(CH$_2$—CH$_2$O)$_5$](Me)(HO)Si(CH$_2$)$_3$]—SH,
[[C$_9$H$_{19}$O—(CH$_2$—CH$_2$O)$_6$](Me)(HO)Si(CH$_2$)$_3$]—SH,
[[C$_{10}$H$_{21}$O—(CH$_2$—CH$_2$O)$_2$](Me)(HO)Si(CH$_2$)$_3$]—SH,
[[C$_{10}$H$_{21}$O—(CH$_2$—CH$_2$O)$_3$](Me)(HO)Si(CH$_2$)$_3$]—SH,
[[C$_{10}$H$_{21}$O—(CH$_2$—CH$_2$O)$_4$](Me)(HO)Si(CH$_2$)$_3$]—SH,
[[C$_{10}$H$_{21}$O—(CH$_2$—CH$_2$O)$_5$](Me)(HO)Si(CH$_2$)$_3$]—SH,
[[C$_{10}$H$_{21}$O—(CH$_2$—CH$_2$O)$_6$](Me)(HO)Si(CH$_2$)$_3$]—SH,
[[C$_{11}$H$_{23}$O—(CH$_2$—CH$_2$O)$_2$](Me)(Ho)Si(CH$_2$)$_3$]—SH,
[[C$_{11}$H$_{23}$O—(CH$_2$—CH$_2$O)$_3$](Me)(HO)Si(CH$_2$)$_3$]—SH,
[[C$_{11}$H$_{23}$O—(CH$_2$—CH$_2$O)$_4$](Me)(HO)Si(CH$_2$)$_3$]—SH,
[[C$_{11}$H$_{23}$O—(CH$_2$—CH$_2$O)$_5$](Me)(HO)Si(CH$_2$)$_3$]—SH,
[[C$_{11}$H$_{23}$O—(CH$_2$—CH$_2$O)$_6$](Me)(HO)Si(CH$_2$)$_3$]—SH,
[[C$_{12}$H$_{25}$O—(CH$_2$—CH$_2$O)$_2$](Me)(HO)Si(CH$_2$)$_3$]—SH,
[[C$_{12}$H$_{25}$O—(CH$_2$—CH$_2$O)$_3$](Me)(HO)Si(CH$_2$)$_3$]—SH,
[[C$_{12}$H$_{25}$O—(CH$_2$—CH$_2$O)$_4$](Me)(HO)Si(CH$_2$)$_3$]—SH,
[[C$_{12}$H$_{25}$O—(CH$_2$—CH$_2$O)$_5$](Me)(HO)Si(CH$_2$)$_3$]—SH,
[[C$_{12}$H$_{25}$O—(CH$_2$—CH$_2$O)$_6$](Me)(HO)Si(CH$_2$)$_3$]—SH,
[[C$_{13}$H$_{27}$O—(CH$_2$—CH$_2$O)$_2$](Me)(HO)Si(CH$_2$)$_3$]—SH,
[[C$_{13}$H$_{27}$O—(CH$_2$—CH$_2$O)$_3$](Me)(HO)Si(CH$_2$)$_3$]—SH,
[[C$_{13}$H$_{27}$O—(CH$_2$—CH$_2$O)$_4$](Me)(HO)Si(CH$_2$)$_3$]—SH,
[[C$_{13}$H$_{27}$O—(CH$_2$—CH$_2$O)$_5$](Me)(HO)Si(CH$_2$)$_3$]—SH,
[[C$_{13}$H$_{27}$O—(CH$_2$—CH$_2$O)$_6$](Me)(HO)Si(CH$_2$)$_3$]—SH,
[[C$_{14}$H$_{29}$O—(CH$_2$—CH$_2$O)$_2$](Me)(HO)Si(CH$_2$)$_3$]—SH,
[[C$_{14}$H$_{29}$O—(CH$_2$—CH$_2$O)$_3$](Me)(HO)Si(CH$_2$)$_3$]—SH,
[[C$_{14}$H$_{29}$O—(CH$_2$—CH$_2$O)$_4$](Me)(HO)Si(CH$_2$)$_3$]—SH,
[[C$_{14}$H$_{29}$O—(CH$_2$—CH$_2$O)$_5$](Me)(HO)Si(CH$_2$)$_3$]—SH,
[[C$_{14}$H$_{29}$O—(CH$_2$—CH$_2$O)$_6$](Me)(HO)Si(CH$_2$)$_3$]—SH,
[[C$_{15}$H$_{31}$O—(CH$_2$—CH$_2$O)$_2$](Me)(HO)Si(CH$_2$)$_3$]—SH,
[[C$_{15}$H$_{31}$O—(CH$_2$—CH$_2$O)$_3$](Me)(HO)Si(CH$_2$)$_3$]—SH,
[[C$_{15}$H$_{31}$O—(CH$_2$—CH$_2$O)$_4$](Me)(HO)Si(CH$_2$)$_3$]—SH,
[[C$_{15}$H$_{31}$O—(CH$_2$—CH$_2$O)$_5$](Me)(HO)Si(CH$_2$)$_3$]—SH,
[[C$_{15}$H$_{31}$O—(CH$_2$—CH$_2$O)$_6$](Me)(HO)Si(CH$_2$)$_3$]—SH,
[[C$_{16}$H$_{33}$O—(CH$_2$—CH$_2$O)$_2$](Me)(HO)Si(CH$_2$)$_3$]—SH,
[[C$_{16}$H$_{33}$O—(CH$_2$—CH$_2$O)$_3$](Me)(HO)Si(CH$_2$)$_3$]—SH,
[[C$_{16}$H$_{33}$O—(CH$_2$—CH$_2$O)$_4$](Me)(HO)Si(CH$_2$)$_3$]—SH,
[[C$_{16}$H$_{33}$O—(CH$_2$—CH$_2$O)$_5$](Me)(HO)Si(CH$_2$)$_3$]—SH,
[[C$_{16}$H$_{33}$O—(CH$_2$—CH$_2$O)$_6$](Me)(HO)Si(CH$_2$)$_3$]—SH,
[[C$_{17}$H$_{35}$O—(CH$_2$—CH$_2$O)$_2$](Me)(HO)Si(CH$_2$)$_3$]—SH,
[[C$_{17}$H$_{35}$O—(CH$_2$—CH$_2$O)$_3$](Me)(HO)Si(CH$_2$)$_3$]—SH,
[[C$_{17}$H$_{35}$O—(CH$_2$—CH$_2$O)$_4$](Me)(HO)Si(CH$_2$)$_3$]—SH,
[[C$_{17}$H$_{35}$O—(CH$_2$—CH$_2$O)$_5$](Me)(HO)Si(CH$_2$)$_3$]—SH,
[[C$_{17}$H$_{35}$O—(CH$_2$—CH$_2$O)$_6$](Me)(HO)Si(CH$_2$)$_3$]—SH,

[[C₁₈H₃₇O—(CH₂—CH₂O)₂](Me)(HO)Si(CH₂)₃]—SH,
[[C₁₈H₃₇O—(CH₂—CH₂O)₃](Me)(HO)Si(CH₂)₃]—SH,
[[C₁₈H₃₇O—(CH₂—CH₂O)₄](Me)(HO)Si(CH₂)₃]—SH,
[[C₁₈H₃₇O—(CH₂—CH₂O)₅](Me)(HO)Si(CH₂)₃]—SH,
[[C₁₈H₃₇O—(CH₂—CH₂O)₆](Me)(HO)Si(CH₂)₃]—SH,
[[C₃H₇O—(CH₂—CH₂O)₂](MeO)(HO)Si(CH₂)₃]—SH,
[[C₃H₇O—(CH₂—CH₂O)₃](MeO)(HO)Si(CH₂)₃]—SH,
[[C₃H₇O—(CH₂—CH₂O)₄](MeO)(HO)Si(CH₂)₃]—SH,
[[C₃H₇O—(CH₂—CH₂O)₅](MeO)(HO)Si(CH₂)₃]—SH,
[[C₃H₇O—(CH₂—CH₂O)₆](MeO)(HO)Si(CH₂)₃]—SH,
[[C₄H₉O—(CH₂—CH₂O)₂](MeO)(HO)Si(CH₂)₃]—SH,
[[C₄H₉O—(CH₂—CH₂O)₃](MeO)(HO)Si(CH₂)₃]—SH,
[[C₄H₉O—(CH₂—CH₂O)₄](MeO)(HO)Si(CH₂)₃]—SH,
[[C₄H₉O—(CH₂—CH₂O)₅](MeO)(HO)Si(CH₂)₃]—SH,
[[C₄H₉O—(CH₂—CH₂O)₆](MeO)(HO)Si(CH₂)₃]—SH,
[[C₅H₁₁O—(CH₂—CH₂O)₂](MeO)(HO)Si(CH₂)₃]—SH,
[[C₅H₁₁O—(CH₂—CH₂O)₃](MeO)(HO)Si(CH₂)₃]—SH,
[[C₅H₁₁O—(CH₂—CH₂O)₄](MeO)(HO)Si(CH₂)₃]—SH,
[[C₅H₁₁O—(CH₂—CH₂O)₅](MeO)(HO)Si(CH₂)₃]—SH,
[[C₅H₁₁O—(CH₂—CH₂O)₆](MeO)(HO)Si(CH₂)₃]—SH,
[[C₆H₁₃O—(CH₂—CH₂O)₂](MeO)(HO)Si(CH₂)₃]—SH,
[[C₆H₁₃O—(CH₂—CH₂O)₃](MeO)(HO)Si(CH₂)₃]—SH,
[[C₆H₁₃O—(CH₂—CH₂O)₄](MeO)(HO)Si(CH₂)₃]—SH,
[[C₆H₁₃O—(CH₂—CH₂O)₅](MeO)(HO)Si(CH₂)₃]—SH,
[[C₆H₁₃O—(CH₂—CH₂O)₆](MeO)(HO)Si(CH₂)₃]—SH,
[[C₇H₁₅O—(CH₂—CH₂O)₂](MeO)(HO)Si(CH₂)₃]—SH,
[[C₇H₁₅O—(CH₂—CH₂O)₃](MeO)(HO)Si(CH₂)₃]—SH,
[[C₇H₁₅O—(CH₂—CH₂O)₄](MeO)(HO)Si(CH₂)₃]—SH,
[[C₇H₁₅O—(CH₂—CH₂O)₅](MeO)(HO)Si(CH₂)₃]—SH,
[[C₇H₁₅O—(CH₂—CH₂O)₆](MeO)(HO)Si(CH₂)₃]—SH,
[[C₈H₁₇O—(CH₂—CH₂O)₂](MeO)(HO)Si(CH₂)₃]—SH,
[[C₈H₁₇O—(CH₂—CH₂O)₃](MeO)(HO)Si(CH₂)₃]—SH,
[[C₈H₁₇O—(CH₂—CH₂O)₄](MeO)(HO)Si(CH₂)₃]—SH,
[[C₈H₁₇O—(CH₂—CH₂O)₅](MeO)(HO)Si(CH₂)₃]—SH,
[[C₈H₁₇O—(CH₂—CH₂O)₆](MeO)(HO)Si(CH₂)₃]—SH,
[[C₉H₁₉O—(CH₂—CH₂O)₂](MeO)(HO)Si(CH₂)₃]—SH,
[[C₉H₁₉O—(CH₂—CH₂O)₃](MeO)(HO)Si(CH₂)₃]—SH,
[[C₉H₁₉O—(CH₂—CH₂O)₄](MeO)(HO)Si(CH₂)₃]—SH,
[[C₉H₁₉O—(CH₂—CH₂O)₅](MeO)(HO)Si(CH₂)₃]—SH,
[[C₉H₁₉O—(CH₂—CH₂O)₆](MeO)(HO)Si(CH₂)₃]-al,
[[C₁₀H₂₁O—(CH₂—CH₂O)₂](MeO)(HO)Si(CH₂)₃]—SH,
[[C₁₀H₂₁O—(CH₂—CH₂O)₃](MeO)(HO)Si(CH₂)₃]—SH,
[[C₁₀H₂₁O—(CH₂—CH₂O)₄](MeO)(HO)Si(CH₂)₃]—SH,
[[C₁₀H₂₁O—(CH₂—CH₂O)₅](MeO)(HO)Si(CH₂)₃]—SH,
[[C₁₀H₂₁O—(CH₂—CH₂O)₆](MeO)(HO)Si(CH₂)₃]—SH,
[[C₁₁H₂₃O—(CH₂—CH₂O)₂](MeO)(HO)Si(CH₂)₃]—SH,
[[C₁₁H₂₃O—(CH₂—CH₂O)₃](MeO)(HO)Si(CH₂)₃]—SH,
[[C₁₁H₂₃O—(CH₂—CH₂O)₄](MeO)(HO)Si(CH₂)₃]—SH,
[[C₁₁H₂₃O—(CH₂—CH₂O)₅](MeO)(HO)Si(CH₂)₃]—SH,
[[C₁₁H₂₃O—(CH₂—CH₂O)₆](MeO)(HO)Si(CH₂)₃]—SH,
[[C₁₂H₂₅O—(CH₂—CH₂O)₂](MeO)(HO)Si(CH₂)₃]—SH,
[[C₁₂H₂₅O—(CH₂—CH₂O)₃](MeO)(HO)Si(CH₂)₃]—SH,
[[C₁₂H₂₅O—(CH₂—CH₂O)₄](MeO)(HO)Si(CH₂)₃]-SH,
[[C₁₂H₂₅O—(CH₂—CH₂O)₅](MeO)(HO)Si(CH₂)₃]—SH,
[[C₁₂H₂₅O—(CH₂—CH₂O)₆](MeO)(HO)Si(CH₂)₃]—SH,
[[C₁₃H₂₇O—(CH₂—CH₂O)₂](MeO)(HO)Si(CH₂)₃]—SH,
[[C₁₃H₂₇O—(CH₂—CH₂O)₃](MeO)(HO)Si(CH₂)₃]—SH,
[[C₁₃H₂₇O—(CH₂—CH₂O)₄](MeO)(HO)Si(CH₂)₃]—SH,
[[C₁₃H₂₇O—(CH₂—CH₂O)₅](MeO)(HO)Si(CH₂)₃]—SH,
[[C₁₃H₂₇O—(CH₂—CH₂O)₆](MeO)(HO)Si(CH₂)₃]—SH,
[[C₁₄H₂₉O—(CH₂—CH₂O)₂](MeO)(HO)Si(CH₂)₃]—SH,
[[C₁₄H₂₉O—(CH₂—CH₂O)₃](MeO)(HO)Si(CH₂)₃]—SH,
[[C₁₄H₂₉O—(CH₂—CH₂O)₄](MeO)(HO)Si(CH₂)₃]—SH,
[[C₁₄H₂₉O—(CH₂—CH₂O)₅](MeO)(HO)Si(CH₂)₃]—SH,
[[C₁₄H₂₉O—(CH₂—CH₂O)₆](MeO)(HO)Si(CH₂)₃]—SH,
[[C₁₆H₃₃O—(CH₂—CH₂O)₂](MeO)(HO)Si(CH₂)₃]—SH,
[[C₁₆H₃₃O—(CH₂—CH₂O)₃](MeO)(HO)Si(CH₂)₃]—SH,
[[C₁₆H₃₃O—(CH₂—CH₂O)₄](MeO)(HO)Si(CH₂)₃]—SH,
[[C₁₆H₃₃O—(CH₂—CH₂O)₅](MeO)(HO)Si(CH₂)₃]—SH,
[[C₁₆H₃₃O—(CH₂—CH₂O)₆](MeO)(HO)Si(CH₂)₃]—SH,
[[C₁₈H₃₇O—(CH₂—CH₂O)₂](MeO)(HO)Si(CH₂)₃]—SH,
[[C₁₈H₃₇O—(CH₂—CH₂O)₃](MeO)(HO)Si(CH₂)₃]—SH,
[[C₁₈H₃₇O—(CH₂—CH₂O)₄](MeO)(HO)Si(CH₂)₃]—SH,
[[C₁₈H₃₇O—(CH₂—CH₂O)₅](MeO)(HO)Si(CH₂)₃]—SH,
[[C₁₈H₃₇O—(CH₂—CH₂O)₆](MeO)(HO)Si(CH₂)₃]—SH,
[[C₃H₇O—(CH₂—CH₂O)₂]₂(HO)Si(CH₂)₃]—SH,
[[C₃H₇O—(CH₂—CH₂O)₃]₂(HO)Si(CH₂)₃]—SH,
[[C₃H₇O—(CH₂—CH₂O)₄]₂(HO)Si(CH₂)₃]—SH,
[[C₃H₇O—(CH₂—CH₂O)₅]₂(HO)Si(CH₂)₃]—SH,
[[C₃H₇O—(CH₂—CH₂O)₆]₂(HO)Si(CH₂)₃]—SH,
[[C₄H₉O—(CH₂—CH₂O)₂]₂(HO)Si(CH₂)₃]—SH,
[[C₄H₉O—(CH₂—CH₂O)₃]₂(HO)Si(CH₂)₃]—SH,
[[C₄H₉O—(CH₂—CH₂O)₄]₂(HO)Si(CH₂)₃]—SH,
[[C₄H₉O—(CH₂—CH₂O)₅]₂(HO)Si(CH₂)₃]—SH,
[[C₄H₉O—(CH₂—CH₂O)₆]₂(HO)Si(CH₂)₃]—SH,
[[C₅H₁₁O—(CH₂—CH₂O)₂]₂(HO)Si(CH₂)₃]—SH,
[[C₅H₁₁O—(CH₂—CH₂O)₃]₂(HO)Si(CH₂)₃]—SH,
[[C₅H₁₁O—(CH₂—CH₂O)₄]₂(HO)Si(CH₂)₃]—SH,
[[C₅H₁₁O—(CH₂—CH₂O)₅]₂(HO)Si(CH₂)₃]—SH,
[[C₅H₁₁O—(CH₂—CH₂O)₆]₂(HO)Si(CH₂)₃]—SH,
[[C₆H₁₃O—(CH₂—CH₂O)₂]₂(HO)Si(CH₂)₃]—SH,
[[C₆H₁₃O—(CH₂—CH₂O)₃]₂(HO)Si(CH₂)₃]—SH,
[[C₆H₁₃O—(CH₂—CH₂O)₄]₂(HO)Si(CH₂)₃]—SH,
[[C₆H₁₃O—(CH₂—CH₂O)₅]₂(HO)Si(CH₂)₃]—SH,
[[C₆H₁₃O—(CH₂—CH₂O)₆]₂(HO)Si(CH₂)₃]—SH,
[[C₇H₁₅O—(CH₂—CH₂O)₂]₂(HO)Si(CH₂)₃]—SH,
[[C₇H₁₅O—(CH₂—CH₂O)₃]₂(HO)Si(CH₂)₃]—SH,
[[C₇H₁₅O—(CH₂—CH₂O)₄]₂(HO)Si(CH₂)₃]—SH,
[[C₇H₁₅O—(CH₂—CH₂O)₅]₂(HO)Si(CH₂)₃]—SH,
[[C₇H₁₅O—(CH₂—CH₂O)₆]₂(HO)Si(CH₂)₃]—SH,
[[C₈H₁₇O—(CH₂—CH₂O)₂]₂(HO)Si(CH₂)₃]—SH,
[[C₈H₇O—(CH₂—CH₂O)₃]₂(HO)Si(CH₂)₃]—SH,
[[C₈H₁₇O—(CH₂—CH₂O)₄]₂(HO)Si(CH₂)₃]—SH,
[[C₈H₁₇O—(CH₂—CH₂O)₅]₂(HO)Si(CH₂)₃]—SH,
[[C₈H₁₇O—(CH₂—CH₂O)₆]₂(HO)Si(CH₂)₃]—SH,
[[C₉H₁₉O—(CH₂—CH₂O)₂]₂(HO)Si(CH₂)₃]—SH,
[[C₉H₁₉O—(CH₂—CH₂O)₃]₂(HO)Si(CH₂)₃]—SH,
[[C₉H₁₉O—(CH₂—CH₂O)₄]₂(HO)Si(CH₂)₃]—SH,
[[C₉H₁₉O—(CH₂—CH₂O)₅]₂(HO)Si(CH₂)₃]—SH,
[[C₉H₁₉O—(CH₂—CH₂O)₆]₂(HO)Si(CH₂)₃]—SH,
[[C₁₀H₂₁O—(CH₂—CH₂O)₂]₂(HO)Si(CH₂)₃]—SH,
[[C₁₀H₂₁O—(CH₂—CH₂O)₃]₂(HO)Si(CH₂)₃]—SH,
[[C₁₀H₂₁O—(CH₂—CH₂O)₄]₂(HO)Si(CH₂)₃]—SH,
[[C₁₀H₂₁O—(CH₂—CH₂O)₅]₂(HO)Si(CH₂)₃]—SH,
[[C₁₀H₂₁O—(CH₂—CH₂O)₆]₂(HO)Si(CH₂)₃]—SH,
[[C₁₁H₂₃O—(CH₂—CH₂O)₂]₂(HO)Si(CH₂)₃]—SH,
[[C₁₁H₂₃O—(CH₂—CH₂O)₃]₂(HO)Si(CH₂)₃]—SH,
[[C₁₁H₂₃O—(CH₂—CH₂O)₄]₂(HO)Si(CH₂)₃]—SH,
[[C₁₁H₂₃O—(CH₂—CH₂O)₅]₂(HO)Si(CH₂)₃]—SH,
[[C₁₁H₂₃O—(CH₂—CH₂O)₆]₂(HO)Si(CH₂)₃]—SH,
[[C₁₂H₂₅O—(CH₂—CH₂O)₂]₂(HO)Si(CH₂)₃]—SH,
[[C₁₂H₂₅O—(CH₂—CH₂O)₃]₂(HO)Si(CH₂)₃]—SH,
[[C₁₂H₂₅O—(CH₂—CH₂O)₄]₂(HO)Si(CH₂)₃]—SH,
[[C₁₂H₂₅O—(CH₂—CH₂O)₅]₂(HO)Si(CH₂)₃]—SH,
[[C₁₂H₂₅O—(CH₂—CH₂O)₆]₂(HO)Si(CH₂)₃]—SH,
[[C₁₃H₂₇O—(CH₂—CH₂O)₂]₂(HO)Si(CH₂)₃]—SH,
[[C₁₃H₂₇O—(CH₂—CH₂O)₃]₂(HO)Si(CH₂)₃]—SH,
[[C₁₃H₂₇O—(CH₂—CH₂O)₄]₂(HO)Si(CH₂)₃]—SH,
[[C₁₃H₂₇O—(CH₂—CH₂O)₅]₂(HO)Si(CH₂)₃]—SH,
[[C₁₃H₂₇O—(CH₂—CH₂O)₆]₂(HO)Si(CH₂)₃]—SH,
[[C₁₄H₂₉O—(CH₂—CH₂O)₂]₂(HO)Si(CH₂)₃]—SH,
[[C₁₄H₂₉O—(CH₂—CH₂O)₃]₂(HO)Si(CH₂)₃]—SH,
[[C₁₄H₂₉O—(CH₂—CH₂O)₄]₂(HO)Si(CH₂)₃]—SH,

[[C₁₄H₂₉O—(CH₂—CH₂O)₅]₂(HO)Si(CH₂)₃]—SH,
[[C₁₄H₂₉O—(CH₂—CH₂O)₆]₂(HO)Si(CH₂)₃]—SH,
[[C₁₆H₃₃O—(CH₂—CH₂O)₂]₂(HO)Si(CH₂)₃]—SH,
[[C₁₆H₃₃O—(CH₂—CH₂O)₃]₂(HO)Si(CH₂)₃]—SH,
[[C₁₆H₃₃O—(CH₂—CH₂O)₄]₂(HO)Si(CH₂)₃]—SH,
[[C₁₆H₃₃O—(CH₂—CH₂O)₅]₂(HO)Si(CH₂)₃]—SH,
[[C₁₆H₃₃O—(CH₂—CH₂O)₆]₂(HO)Si(CH₂)₃]—SH,
[[C₁₈H₃₇O—(CH₂—CH₂O)₂]₂(HO)Si(CH₂)₃]—SH,
[[C₁₈H₃₇O—(CH₂—CH₂O)₃]₂(HO)Si(CH₂)₃]—SH,
[[C₁₈H₃₇O—(CH₂—CH₂O)₄]₂(HO)Si(CH₂)₃]—SH,
[[C₁₈H₃₇O—(CH₂—CH₂O)₅]₂(HO)Si(CH₂)₃]—SH,
[[C₁₈H₃₇O—(CH₂—CH₂O)₆]₂(HO)Si(CH₂)₃]—SH,
[[C₃H₇O—(CH₂—CH₂O)₂](EtO)(HO)Si(CH₂)₃]—SH,
[[C₃H₇O—(CH₂—CH₂O)₃](EtO)(HO)Si(CH₂)₃]—SH,
[[C₃H₇O—(CH₂—CH₂O)₄](EtO)(HO)Si(CH₂)₃]—SH,
[[C₃H₇O—(CH₂—CH₂O)₅](EtO)(HO)Si(CH₂)₃]—SH,
[[C₃H₇O—(CH₂—CH₂O)₆](EtO)(HO)Si(CH₂)₃]—SH,
[[C₄H₉O—(CH₂—CH₂O)₂](EtO)(HO)Si(CH₂)₃]—SH,
[[C₄H₉O—(CH₂—CH₂O)₃](EtO)(HO)Si(CH₂)₃]—SH,
[[C₄H₉O—(CH₂—CH₂O)₄](EtO)(HO)Si(CH₂)₃]—SH,
[[C₄H₉O—(CH₂—CH₂O)₅](EtO)(HO)Si(CH₂)₃]—SH,
[[C₄H₉O—(CH₂—CH₂O)₆](EtO)(HO)Si(CH₂)₃]—SH,
[[C₅H₁₁O—(CH₂—CH₂O)₂](EtO)(HO)Si(CH₂)₃]—SH,
[[C₅H₁₁O—(CH₂—CH₂O)₃](EtO)(HO)Si(CH₂)₃]—SH,
[[C₅H₁₁O—(CH₂—CH₂O)₄](EtO)(HO)Si(CH₂)₃]—SH,
[[C₅H₁₁O—(CH₂—CH₂O)₅](EtO)(HO)Si(CH₂)₃]—SH,
[[C₅H₁₁O—(CH₂—CH₂O)₆](EtO)(HO)Si(CH₂)₃]—SH,
[[C₆H₁₃O—(CH₂—CH₂O)₂](EtO)(HO)Si(CH₂)₃]—SH,
[[C₆H₁₃O—(CH₂—CH₂O)₃](EtO)(HO)Si(CH₂)₃]—SH,
[[C₆H₁₃O—(CH₂—CH₂O)₄](EtO)(HO)Si(CH₂)₃]—SH,
[[C₆H₁₃O—(CH₂—CH₂O)₅](EtO)(HO)Si(CH₂)₃]—SH,
[[C₆H₁₃O—(CH₂—CH₂O)₆](EtO)(HO)Si(CH₂)₃]—SH,
[[C₇H₁₅O—(CH₂—CH₂O)₂](EtO)(HO)Si(CH₂)₃]—SH,
[[C₇H₅O—(CH₂—CH₂O)₃](EtO)(HO)Si(CH₂)₃]—SH,
[[C₇H₅O—(CH₂—CH₂O)₄](EtO)(HO)Si(CH₂)₃]—SH,
[[C₇H₁₅O—(CH₂—CH₂O)₅](EtO)(HO)Si(CH₂)₃]—SH,
[[C₇H₁₅O—(CH₂—CH₂O)₆](EtO)(HO)Si(CH₂)₃]—SH,
[[C₈H₁₇O—(CH₂—CH₂O)₂](EtO)(HO)Si(CH₂)₃]—SH,
[[C₈H₁₇O—(CH₂—CH₂O)₃](EtO)(HO)Si(CH₂)₃]—SH,
[[C₈H₁₇O—(CH₂—CH₂O)₄](EtO)(HO)Si(CH₂)₃]—SH,
[[C₈H₁₇O—(CH₂—CH₂O)₅](EtO)(HO)Si(CH₂)₃]—SH,
[[C₈H₁₇O—(CH₂—CH₂O)₆](EtO)(HO)Si(CH₂)₃]—SH,
[[C₉H₁₉O—(CH₂—CH₂O)₂](EtO)(HO)Si(CH₂)₃]—SH,
[[C₉H₁₉O—(CH₂—CH₂O)₃](EtO)(HO)Si(CH₂)₃]—SH,
[[C₉H₁₉O—(CH₂—CH₂O)₄](EtO)(HO)Si(CH₂)₃]—SH,
[[C₉H₁₉O—(CH₂—CH₂O)₅](EtO)(HO)Si(CH₂)₃]—SH,
[[C₉H₁₉O—(CH₂—CH₂O)₆](EtO)(HO)Si(CH₂)₃]—SH,
[[C₁₀H₂₁O—(CH₂—CH₂O)₂](EtO)(HO)Si(CH₂)₃]—SH,
[[C₁₀H₂₁O—(CH₂—CH₂O)₃](EtO)(HO)Si(CH₂)₃]—SH,
[[C₁₀H₂₁O—(CH₂—CH₂O)₄](EtO)(HO)Si(CH₂)₃]—SH,
[[C₁₀H₂₁O—(CH₂—CH₂O)₅](EtO)(HO)Si(CH₂)₃]—SH,
[[C₁₀H₂₁O—(CH₂—CH₂O)₆](EtO)(HO)Si(CH₂)₃]—SH,
[[C₁₁H₂₃O—(CH₂—CH₂O)₂](EtO)(HO)Si(CH₂)₃]—SH,
[[C₁₁H₂₃O—(CH₂—CH₂O)₃](EtO)(HO)Si(CH₂)₃]—SH,
[[C₁₁H₂₃O—(CH₂—CH₂O)₄](EtO)(HO)Si(CH₂)₃]—SH,
[[C₁₁H₂₃O—(CH₂—CH₂O)₅](EtO)(HO)Si(CH₂)₃]—SH,
[[C₁₁H₂₃O—(CH₂—CH₂O)₆](EtO)(HO)Si(CH₂)₃]—SH,
[[C₁₂H₂₅O—(CH₂—CH₂O)₂](EtO)(HO)Si(CH₂)₃]—SH,
[[C₁₂H₂₅O—(CH₂—CH₂O)₃](EtO)(HO)Si(CH₂)₃]—SH,
[[C₁₂H₂₅O—(CH₂—CH₂O)₄](EtO)(HO)Si(CH₂)₃]—SH,
[[C₁₂H₂₅O—(CH₂—CH₂O)₅](EtO)(HO)Si(CH₂)₃]—SH,
[[C₁₂H₂₅—(CH₂—CH₂O)₆](EtO)(HO)Si(CH₂)₃]—SH,
[[C₁₃H₂₇O—(CH₂—CH₂O)₂](EtO)(HO)Si(CH₂)₃]—SH,
[[C₁₃H₂₇O—(CH₂—CH₂O)₃](EtO)(HO)Si(CH₂)₃]—SH,
[[C₁₃H₂₇O—(CH₂—CH₂O)₄](EtO)(HO)Si(CH₂)₃]—SH,
[[C₁₃H₂₇O—(CH₂—CH₂O)₅](EtO)(HO)Si(CH₂)₃]—SH,
[[C₁₃H₂₇O—(CH₂—CH₂O)₆](EtO)(HO)Si(CH₂)₃]—SH,
[[C₁₄H₂₉O—(CH₂—CH₂O)₂](EtO)(HO)Si(CH₂)₃]—SH,
[[C₁₄H₂₉O—(CH₂—CH₂O)₃](EtO)(HO)Si(CH₂)₃]—SH,
[[C₁₄H₂₉O—(CH₂—CH₂O)₄](EtO)(HO)Si(CH₂)₃]—SH,
[[C₁₄H₂₉O—(CH₂—CH₂O)₅](EtO)(HO)Si(CH₂)₃]—SH,
[[C₁₄H₂₉O—(CH₂—CH₂O)₆](EtO)(HO)Si(CH₂)₃]—SH,
[[C₁₆H₃₃O—(CH₂—CH₂O)₃](EtO)(HO)Si(CH₂)₃]—SH,
[[C₁₆H₃₃O—(CH₂—CH₂O)₄](EtO)(HO)Si(CH₂)₃]—SH,
[[C₁₆H₃₃O—(CH₂—CH₂O)₅](EtO)(HO)Si(CH₂)₃]—SH,
[[C₁₆H₃₃O—(CH₂—CH₂O)₆](EtO)(HO)Si(CH₂)₃]—SH,
[[C₁₇H₃₅O—(CH₂—CH₂O)₂](EtO)(HO)Si(CH₂)₃]—SH,
[[C₁₇H₃₅O—(CH₂—CH₂O)₃](EtO)(HO)Si(CH₂)₃]—SH,
[[C₁₇H₃₅O—(CH₂—CH₂O)₄](EtO)(HO)Si(CH₂)₃]—SH,
[[C₁₇H₃₅O—(CH₂—CH₂O)₅](EtO)(HO)Si(CH₂)₃]—SH,
[[C₁₇H₃₅O—(CH₂—CH₂O)₆](EtO)(HO)Si(CH₂)₃]—SH,
[[C₁₈H₃₇O—(CH₂—CH₂O)₂](EtO)(HO)Si(CH₂)₃]—SH,
[[C₁₈H₃₇O—(CH₂—CH₂O)₃](EtO)(HO)Si(CH₂)₃]—SH,
[[C₁₈H₃₇O—(CH₂—CH₂O)₄](EtO)(HO)Si(CH₂)₃]—SH,
[[C₁₈H₃₇O—(CH₂—CH₂O)₅](EtO)(HO)Si(CH₂)₃]—SH,
[[C₁₈H₃₇O—(CH₂—CH₂O)₆](EtO)(HO)Si(CH₂)₃]—SH,
[[C₃H₇O—(CH₂—CH₂O)₂](HO)₂Si(CH₂)₃]—SH,
[[C₃H₇O—(CH₂—CH₂O)₃](HO)₂Si(CH₂)₃]—SH,
[[C₃H₇O—(CH₂—CH₂O)₄](HO)₂Si(CH₂)₃]—SH,
[[C₃H₇O—(CH₂—CH₂O)₅](HO)₂Si(CH₂)₃]—SH,
[[C₃H₇O—(CH₂—CH₂O)₆](HO)₂Si(CH₂)₃]—SH,
[[C₄H₉O—(CH₂—CH₂O)₂](HO)₂Si(CH₂)₃]—SH,
[[C₄H₉O—(CH₂—CH₂O)₃](HO)₂Si(CH₂)₃]—SH,
[[C₄H₉O—(CH₂—CH₂O)₄](HO)₂Si(CH₂)₃]—SH,
[[C₄H₉O—(CH₂—CH₂O)₅](HO)₂Si(CH₂)₃]—SH,
[[C₄H₉O—(CH₂—CH₂O)₆](HO)₂Si(CH₂)₃]—SH
[[C₅H₁₁O—(CH₂—CH₂O)₂](HO)₂Si(CH₂)₃]—SH,
[[C₅H₁₁O—(CH₂—CH₂O)₃](HO)₂Si(CH₂)₃]—SH,
[[C₅H₁₁O—(CH₂—CH₂O)₄](HO)₂Si(CH₂)₃]—SH,
[[C₅H₁₁O—(CH₂—CH₂O)₅](HO)₂Si(CH₂)₃]—SH,
[[C₅H₁₁O—(CH₂—CH₂O)₆](HO)₂Si(CH₂)₃]—SH,
[[C₆H₁₃O—(CH₂—CH₂O)₂](HO)₂Si(CH₂)₃]—SH,
[[C₆H₁₃O—(CH₂—CH₂O)₃](HO)₂Si(CH₂)₃]—SH,
[[C₆H₁₃O—(CH₂—CH₂O)₄](HO)₂Si(CH₂)₃]—SH,
[[C₆H₁₃O—(CH₂—CH₂O)₅](HO)₂Si(CH₂)₃]—SH,
[[C₆H₁₃O—(CH₂—CH₂O)₆](HO)₂Si(CH₂)₃]—SH,
[[C₇H₁₅O—(CH₂—CH₂O)₂](HO)₂Si(CH₂)₃]—SH,
[[C₇H₁₅O—(CH₂—CH₂O)₃](HO)₂Si(CH₂)₃]—SH,
[[C₇H₁₅O—(CH₂—CH₂O)₄](HO)₂Si(CH₂)₃]—SH,
[[C₇H₁₅O—(CH₂—CH₂O)₅](HO)₂Si(CH₂)₃]—SH,
[[C₇H₁₅O—(CH₂—CH₂O)₆](HO)₂Si(CH₂)₃]—SH,
[[C₈H₁₇O—(CH₂—CH₂O)₂](HO)₂Si(CH₂)₃]—SH,
[[C₈H₁₇O—(CH₂—CH₂O)₃](HO)₂Si(CH₂)₃]—SH,
[[C₈H₁₇O—(CH₂—CH₂O)₄](HO)₂Si(CH₂)₃]—SH,
[[C₈H₁₇O—(CH₂—CH₂O)₅](HO)₂Si(CH₂)₃]—SH,
[[C₈H₁₇O—(CH₂—CH₂O)₆](HO)₂Si(CH₂)₃]—SH,
[[C₉H₁₉O—(CH₂—CH₂O)₂](HO)₂Si(CH₂)₃]—SH,
[[C₉H₁₉O—(CH₂—CH₂O)₃](HO)₂Si(CH₂)₃]—SH,
[[C₉H₁₉O—(CH₂—CH₂O)₄](HO)₂Si(CH₂)₃]—SH,
[[C₉H₁₉O—(CH₂—CH₂O)₅](HO)₂Si(CH₂)₃]—SH,
[[C₉H₁₉O—(CH₂—CH₂O)₆](HO)₂Si(CH₂)₃]—SH,
[[C₁₀H₂₁O—(CH₂—CH₂O)₂](HO)₂Si(CH₂)₃]—SH,
[[C₁₀H₂₁O—(CH₂—CH₂O)₃](HO)₂Si(CH₂)₃]—SH,
[[C₁₀H₂₁O—(CH₂—CH₂O)₄](HO)₂Si(CH₂)₃]—SH,
[[C₁₀H₂₁O—(CH₂—CH₂O)₅](HO)₂Si(CH₂)₃]—SH,
[[C₁₀H₂₁O—(CH₂—CH₂O)₆](HO)₂Si(CH₂)₃]—SH,
[[C₁₁H₂₃O—(CH₂—CH₂O)₂](HO)₂Si(CH₂)₃]—SH,
[[C₁₁H₂₃O—(CH₂—CH₂O)₃](HO)₂Si(CH₂)₃]—SH,
[[C₁₁H₂₃O—(CH₂—CH₂O)₄](HO)₂Si(CH₂)₃]—SH,
[[C₁₁H₂₃O—(CH₂—CH₂O)₅](HO)₂Si(CH₂)₃]—SH,
[[C₁₁H₂₃O—(CH₂—CH₂O)₆](HO)₂Si(CH₂)₃]—SH,
[[C₁₂H₂₅O—(CH₂—CH₂O)₂](HO)₂Si(CH₂)₃]—SH,
[[C₁₂H₂₅O—(CH₂—CH₂O)₃](HO)₂Si(CH₂)₃]—SH,

[[C$_{12}$H$_{25}$O—(CH$_2$—CH$_2$O)$_4$](HO)$_2$Si(CH$_2$)$_3$]—SH,
[[C$_{12}$H$_{25}$O—(CH$_2$—CH$_2$O)$_5$](HO)$_2$Si(CH$_2$)$_3$]—SH,
[[C$_{12}$H$_{25}$O—(CH$_2$—CH$_2$O)$_6$](HO)$_2$Si(CH$_2$)$_3$]—SH,
[[C$_{13}$H$_{27}$O—(CH$_2$—CH$_2$O)$_2$](HO)$_2$Si(CH$_2$)$_3$]—SH,
[[C$_{13}$H$_{27}$O—(CH$_2$—CH$_2$O)$_3$](HO)$_2$Si(CH$_2$)$_3$]—SH,
[[C$_{13}$H$_{27}$O—(CH$_2$—CH$_2$O)$_4$](HO)$_2$Si(CH$_2$)$_3$]—SH,
[[C$_{13}$H$_{27}$O—(CH$_2$—CH$_2$O)$_5$](HO)$_2$Si(CH$_2$)$_3$]—SH,
[[C$_{13}$H$_{27}$O—(CH$_2$—CH$_2$O)$_6$](HO)$_2$Si(CH$_2$)$_3$]—SH,
[[C$_{14}$H$_{29}$O—(CH$_2$—CH$_2$O)$_2$](HO)$_2$Si (CH$_2$)$_3$]—SH,
[[C$_{14}$H$_{29}$O—(CH$_2$—CH$_2$O)$_3$](HO)$_2$Si(CH$_2$)$_3$]—SH,
[[C$_{14}$H$_{29}$O—(CH$_2$—CH$_2$O)$_4$](HO)$_2$Si(CH$_2$)$_3$]—SH,
[[C$_{14}$H$_{29}$O—(CH$_2$—CH$_2$O)$_5$](HO)$_2$Si(CH$_2$)$_3$]—SH,
[[C$_{14}$H$_{29}$O—(CH$_2$—CH$_2$O)$_6$](HO)$_2$Si(CH$_2$)$_3$]—SH,
[[C$_{16}$H$_{33}$O—(CH$_2$—CH$_2$O)$_2$](HO)$_2$Si(CH$_2$)$_3$]—SH,
[[C$_{16}$H$_{33}$O—(CH$_2$—CH$_2$O)$_3$](HO)$_2$Si(CH$_2$)$_3$]—SH,
[[C$_{16}$H$_{33}$O—(CH$_2$—CH$_2$O)$_4$](HO)$_2$Si(CH$_2$)$_3$]—SH,
[[C$_{16}$H$_{33}$O—(CH$_2$—CH$_2$O)$_5$](HO)$_2$Si(CH$_2$)$_3$]—SH,
[[C$_{16}$H$_{33}$O—(CH$_2$—CH$_2$O)$_6$](HO)$_2$Si(CH$_2$)$_3$]—SH,
[[C$_{17}$H$_{35}$O—(CH$_2$—CH$_2$O)$_2$](HO)$_2$Si(CH$_2$)$_3$]—SH,
[[C$_{17}$H$_{35}$O—(CH$_2$—CH$_2$O)$_3$](HO)$_2$Si(CH$_2$)$_3$]—SH,
[[C$_{17}$H$_{35}$O—(CH$_2$—CH$_2$O)$_4$](HO)$_2$Si(CH$_2$)$_3$]—SH,
[[C$_{17}$H$_{35}$O—(CH$_2$—CH$_2$O)$_5$](HO)$_2$Si(CH$_2$)$_3$]—SH,
[[C$_{17}$H$_{35}$O—(CH$_2$—CH$_2$O)$_6$](HO)$_2$Si(CH$_2$)$_3$]—SH,
[[C$_{18}$H$_{37}$O—(CH$_2$—CH$_2$O)$_2$](HO)$_2$Si(CH$_2$)$_3$]—SH,
[[C$_{18}$H$_{37}$O—(CH$_2$—CH$_2$O)$_3$](HO)$_2$Si(CH$_2$)$_3$]—SH,
[[C$_{18}$H$_{37}$O—(CH$_2$—CH$_2$O)$_4$](HO)$_2$Si(CH$_2$)$_3$]—SH,
[[C$_{18}$H$_{37}$O—(CH$_2$—CH$_2$O)$_5$](HO)$_2$Si(CH$_2$)$_3$]—SH, or
[[C$_{18}$H$_{37}$O—(CH$_2$—CH$_2$O)$_6$](M)$_2$Si(CH$_2$)$_3$]—SH, where the alkyl moieties can be unbranched or branched.

Compounds of the formula I, where Alk =C$_3$H$_7$, C$_4$H$_9$, C$_5$H$_{11}$, C$_6$H$_{13}$, C$_7$H$_{15}$, C$_8$H$_{17}$, C$_9$H$_{19}$, C$_{10}$H$_{21}$, C$_{11}$H$_{23}$, C$_{12}$H$_{25}$, C$_{13}$H$_{27}$, C$_{14}$H$_{29}$, C$_{15}$H$_{31}$ C$_{16}$H$_{33}$, C$_{17}$H$_{35}$, or C$_{19}$H$_{37}$, can be:
[[Alk-O—(CH$_2$—CH(CH$_3$)O—)$_2$](MeO)(HO)Si(CH$_2$)$_3$]—SH, [[Alk-O—(CH$_2$—CH(CH$_3$)O—)$_3$](MeO)(HO)Si(CH$_2$)$_3$]—SH, [[Alk-O—(CH$_2$—CH(CH$_3$)O—)$_4$](MeO)(HO)Si(CH$_2$)$_3$]—SH, [[Alk-O—(CH$_2$—CH(CH$_3$)O—)$_5$](MeO)(HO)Si(CH$_2$)$_3$]—SH, [[Alk-O—(CH$_2$—CH(CH$_3$)O—)$_6$](MeO)(HO)Si(CH$_2$)$_3$]—SH,
[[Alk-O—(CH$_2$—CH(CH$_3$)O—)$_2$]$_2$(HO)Si(CH$_2$)$_3$]—SH,
[[Alk-O—(CH$_2$—CH(CH$_3$)O—)$_3$]$_2$(HO)Si(CH$_2$)$_3$]—SH,
[[Alk-O—(CH$_2$—CH(CH$_3$)O—)$_4$]$_2$(HO)Si(CH$_2$)$_3$]—SH,
[[Alk-O—(CH$_2$—CH(CH$_3$)O—)$_5$]$_2$(HO)Si(CH$_2$)$_3$]—SH,
[[Alk-O—(CH$_2$—CH(CH$_3$)O—)$_6$]$_2$(HO)Si(CH$_2$)$_3$]—SH,
[[Alk-O—(CH$_2$—CH(CH$_3$)O—)$_2$](Me)(HO)Si(CH$_2$)$_3$]—SH, [[Alk-O—(CH$_2$—CH(CH$_3$)O—)$_3$](Me)(HO)Si(CH$_2$)$_3$]—SH, [[Alk-O—(CH$_2$—CH(CH$_3$)O—)$_4$](Me)(HO)Si(CH$_2$)$_3$]—SH, [[Alk-O—(CH$_2$—CH(CH$_3$)O—)$_5$](Me)(HO)Si(CH$_2$)$_3$]—SH, [[Alk-O—(CH$_2$—CH(CH$_3$)O—)$_6$](Me)(HO)Si(CH$_2$)$_3$]—SH,
[[Alk-O—(CH$_2$—CH(CH$_3$)O—)$_2$](EtO)(HO)Si(CH$_2$)$_3$]—SH, [[Alk-O—(CH$_2$—CH(CH$_3$)O—)$_3$](EtO)(HO)Si(CH$_2$)$_3$]—SH, [[Alk-O—(CH$_2$—CH(CH$_3$)O—)$_4$](EtO)(HO)Si(CH$_2$)$_3$]—SH, [[Alk-O—(CH$_2$—CH(CH$_3$)O—)$_5$](EtO)(HO)Si(CH$_2$)$_3$]—SH, [[Alk-O—(CH$_2$—CH(CH$_3$)O—)$_6$](EtO)(HO)Si(CH$_2$)$_3$]—SH,
where the Alk groups can be unbranched or branched.

Preferred compounds of the general formula II can be:
[[C$_3$H$_7$O—(CH$_2$—CH$_2$O)$_2$](Me)(MeO)Si(CH$_2$)$_3$]—SH,
[[C$_3$H$_7$O—(CH$_2$—CH$_2$O)$_3$](Me)(MeO)Si(CH$_2$)$_3$]—SH,
[[C$_3$H$_7$O—(CH$_2$—CH$_2$O)$_4$](Me)(MeO)Si(CH$_2$)$_3$]—SH,
[[C$_3$H$_7$O—(CH$_2$—CH$_2$O)$_5$](Me)(MeO)Si(CH$_2$)$_3$]—SH,
[[C$_3$H$_7$O—(CH$_2$—CH$_2$O)$_6$](Me)(MeO)Si(CH$_2$)$_3$]—SH,
[[C$_4$H$_9$O—(CH$_2$—CH$_2$O)$_2$](Me)(MeO)Si(CH$_2$)$_3$]—SH,
[[C$_4$H$_9$O—(CH$_2$—CH$_2$O)$_3$](Me)(MeO)Si(CH$_2$)$_3$]—SH,
[[C$_4$H$_9$O—(CH$_2$—CH$_2$O)$_4$](Me)(MeO)Si(CH$_2$)$_3$]—SH,
[[C$_4$H$_9$O—(CH$_2$—CH$_2$O)$_5$](Me)(MeO)Si(CH$_2$)$_3$]—SH,
[[C$_4$H$_9$O—(CH$_2$—CH$_2$O)$_6$](Me)(MeO)Si(CH$_2$)$_3$]—SH,
[[C$_5$H$_{11}$O—(CH$_2$—CH$_2$O)$_2$](Me)(MeO)Si(CH$_2$)$_3$]—SH,
[[C$_5$H$_{11}$O—(CH$_2$—CH$_2$O)$_3$](Me)(MeO)Si(CH$_2$)$_3$]—SH,
[[C$_5$H$_{11}$O—(CH$_2$—CH$_2$O)$_4$](Me)(MeO)Si(CH$_2$)$_3$]—SH,
[[C$_5$H$_{11}$O—(CH$_2$—CH$_2$O)$_5$](Me)(MeO)Si(CH$_2$)$_3$]—SH,
[[C$_5$H$_{11}$O—(CH$_2$—CH$_2$O)$_6$](Me)(MeO)Si(CH$_2$)$_3$]—SH,
[[C$_6$H$_{13}$O—(CH$_2$—CH$_2$O)$_2$](Me)(MeO)Si(CH$_2$)$_3$]—SH,
[[C$_6$H$_{13}$O—(CH$_2$—CH$_2$O)$_3$](Me)(MeO)Si(CH$_2$)$_3$]—SH,
[[C$_6$H$_{13}$O—(CH$_2$—CH$_2$O)$_4$](Me)(MeO)Si(CH$_2$)$_3$]—SH,
[[C$_6$H$_{13}$O—(CH$_2$—CH$_2$O)$_5$](Me)(MeO)Si(CH$_2$)$_3$]—SH,
[[C$_6$H$_{13}$O—(CH$_2$—CH$_2$O)$_6$](Me)(MeO)Si(CH$_2$)$_3$]—SH,
[[C$_7$H$_{15}$O—(CH$_2$—CH$_2$O)$_2$](Me)(MeO)Si(CH$_2$)$_3$]—SH,
[[C$_7$H$_{15}$O—(CH$_2$—CH$_2$O)$_3$](Me)(MeO)Si(CH$_2$)$_3$]—SH,
[[C$_7$H$_{15}$O—(CH$_2$—CH$_2$O)$_4$](Me)(MeO)Si(CH$_2$)$_3$]—SH,
[[C$_7$H$_{15}$O—(CH$_2$—CH$_2$O)$_5$](Me)(MeO)Si(CH$_2$)$_3$]—SH,
[[C$_7$H$_{15}$O—(CH$_2$—CH$_2$O)$_6$](Me)(MeO)Si(CH$_2$)$_3$]—SH,
[[C$_8$H$_{17}$O—(CH$_2$—CH$_2$O)$_2$](Me)(MeO)Si(CH$_2$)$_3$]—SH,
[[C$_8$H$_{17}$O—(CH$_2$—CH$_2$O)$_3$](Me)(MeO)Si(CH$_2$)$_3$]—SH,
[[C$_8$H$_{17}$O—(CH$_2$—CH$_2$O)$_4$](Me)(MeO)Si(CH$_2$)$_3$]—SH,
[[C$_8$H$_{17}$O—(CH$_2$—CH$_2$O)$_5$](Me)(MeO)Si(CH$_2$)$_3$]—SH,
[[C$_8$H$_{17}$O—(CH$_2$—CH$_2$O)$_6$](Me)(MeO)Si(CH$_2$)$_3$]—SH,
[[C$_9$H$_{19}$O—(CH$_2$—CH$_2$O)$_2$](Me)(MeO)Si(CH$_2$)$_3$]—SH,
[[C$_9$H$_{19}$O—(CH$_2$—CH$_2$O)$_3$](Me)(MeO)Si(CH$_2$)$_3$]—SH,
[[C$_9$H$_{19}$O—(CH$_2$—CH$_2$O)$_4$](Me)(MeO)Si(CH$_2$)$_3$]—SH,
[[C$_9$H$_{19}$O—(CH$_2$—CH$_2$O)$_5$](Me)(MeO)Si(CH$_2$)$_3$]—SH,
[[C$_9$H$_{19}$O—(CH$_2$—CH$_2$O)$_6$](Me)(MeO)Si(CH$_2$)$_3$]—SH,
[[C$_{10}$H$_{21}$O—(CH$_2$—CH$_2$O)$_2$](Me)(MeO)Si(CH$_2$)$_3$]—SH,
[[C$_{10}$H$_{21}$O—(CH$_2$—CH$_2$O)$_3$](Me)(MeO)Si(CH$_2$)$_3$]—SH,
[[C$_{10}$H$_{21}$O—(CH$_2$—CH$_2$O)$_4$](Me)(MeO)Si(CH$_2$)$_3$]—SH,
[[C$_{10}$H$_{21}$—(CH$_2$—CH$_2$O)$_5$](Me)(MeO)Si(CH$_2$)$_3$]—SH,
[[C$_{10}$H$_{21}$—(CH$_2$—CH$_2$O)$_6$](Me)(MeO)Si(CH$_2$)$_3$]—SH,
[[C$_{11}$H$_{23}$O—(CH$_2$—CH$_2$O)$_2$](Me)(MeO)Si(CH$_2$)$_3$]—SH,
[[C$_{11}$H$_{23}$O—(CH$_2$—CH$_2$O)$_3$](Me)(MeO)Si(CH$_2$)$_3$]—SH,
[[C$_{11}$H$_{23}$O—(CH$_2$—CH$_2$O)$_4$](Me)(MeO)Si(CH$_2$)$_3$]—SH,
[[C$_{11}$H$_{23}$O—(CH$_2$—CH$_2$O)$_5$](Me)(MeO)Si(CH$_2$)$_3$]—SH,
[[C$_{11}$H$_{23}$O—(CH$_2$—CH$_2$O)$_6$](Me)(MeO)Si(CH$_2$)$_3$]—SH,
[[C$_{12}$H$_{25}$O—(CH$_2$—CH$_2$O)$_2$](Me)(MeO)Si(CH$_2$)$_3$]—SH,
[[C$_{12}$H$_{25}$O—(CH$_2$—CH$_2$O)$_3$](Me)(MeO)Si(CH$_2$)$_3$]—SH,
[[C$_{12}$H$_{25}$O—(CH$_2$—CH$_2$O)$_4$](Me)(MeO)Si(CH$_2$)$_3$]—SH,
[[C$_{12}$H$_{25}$O—(CH$_2$—CH$_2$O)$_5$](Me)(MeO)Si(CH$_2$)$_3$]—SH,
[[C$_{12}$H$_{25}$O—(CH$_2$—CH$_2$O)$_6$](Me)(MeO)Si(CH$_2$)$_3$]—SH,
[[C$_{13}$H$_{27}$O—(CH$_2$—CH$_2$O)$_2$](Me)(MeO)Si(CH$_2$)$_3$]—SH,
[[C$_{13}$H$_{27}$O—(CH$_2$—CH$_2$O)$_3$](Me)(MeO)Si(CH$_2$)$_3$]—SH,
[[C$_{13}$H$_{27}$O—(CH$_2$—CH$_2$O)$_4$](Me)(MeO)Si(CH$_2$)$_3$]—SH,
[[C$_{13}$H$_{27}$O—(CH$_2$—CH$_2$O)$_5$](Me)(MeO)Si(CH$_2$)$_3$]—SH,
[[C$_{13}$H$_{27}$O—(CH$_2$—CH$_2$O)$_6$](Me)(MeO)Si(CH$_2$)$_3$]—SH,
[[C$_{14}$H$_{29}$O—(CH$_2$—CH$_2$O)$_2$](Me)(MeO)Si(CH$_2$)$_3$]—SH,
[[C$_{14}$H$_{29}$O—(CH$_2$—CH$_2$O)$_3$](Me)(MeO)Si(CH$_2$)$_3$]—SH,
[[C$_{14}$H$_{29}$O—(CH$_2$—CH$_2$O)$_4$](Me)(MeO)Si(CH$_2$)$_3$]—SH,
[[C$_{14}$H$_{29}$O—(CH$_2$—CH$_2$O)$_5$](Me)(MeO)Si(CH$_2$)$_3$]—SH,
[[C$_{14}$H$_{29}$O—(CH$_2$—CH$_2$O)$_6$](Me)(MeO)Si(CH$_2$)$_3$]—SH,
[[C$_{15}$H$_{31}$O—(CH$_2$—CH$_2$O)$_2$](Me)(MeO)Si(CH$_2$)$_3$]—SH,
[[C$_{15}$H$_{31}$O—(CH$_2$—CH$_2$O)$_3$](Me)(MeO)Si(CH$_2$)$_3$]—SH,
[[C$_{15}$H$_{31}$O—(CH$_2$—CH$_2$O)$_4$](Me)(MeO)Si(CH$_2$)$_3$]—SH,
[[C$_{15}$H$_{31}$O—(CH$_2$—CH$_2$O)$_5$](Me)(MeO)Si(CH$_2$)$_3$]—SH,
[[C$_{15}$H$_{31}$O—(CH$_2$—CH$_2$O)$_6$](Me)(MeO)Si(CH$_2$)$_3$]—SH,
[[C$_{16}$H$_{33}$O—(CH$_2$—CH$_2$O)$_2$](Me)(MeO)Si(CH$_2$)$_3$]—SH,
[[C$_{16}$H$_{33}$O—(CH$_2$—CH$_2$O)$_3$](Me)(MeO)Si(CH$_2$)$_3$]—SH,
[[C$_{16}$H$_{33}$O—(CH$_2$—CH$_2$O)$_4$](Me)(MeO)Si(CH$_2$)$_3$]—SH,
[[C$_{16}$H$_{33}$O—(CH$_2$—CH$_2$O)$_5$](Me)(MeO)Si(CH$_2$)$_3$]—SH,
[[C$_{16}$H$_{33}$O—(CH$_2$—CH$_2$O)$_6$](Me)(MeO)Si(CH$_2$)$_3$]—SH,
[[C$_{17}$H$_{35}$O—(CH$_2$—CH$_2$O)$_2$](Me)(MeO)Si(CH$_2$)$_3$]—SH,
[[C$_{17}$H$_{35}$O—(CH$_2$—CH$_2$O)$_3$](Me)(MeO)Si(CH$_2$)$_3$]—SH,
[[C$_{17}$H$_{35}$O—(CH$_2$—CH$_2$O)$_4$](Me)(MeO)Si(CH$_2$)$_3$]—SH,
[[C$_{17}$H$_{35}$O—(CH$_2$—CH$_2$O)$_5$](Me)(MeO)Si(CH$_2$)$_3$]—SH,
[[C$_{17}$H$_{35}$O—(CH$_2$—CH$_2$O)$_6$](Me)(MeO)Si(CH$_2$)$_3$]—SH,

[[C$_{18}$H$_{37}$O—(CH$_2$—CH$_2$O)$_2$](Me)(MeO)Si(CH$_2$)$_3$]—SH,
[[C$_{18}$H$_{37}$O—(CH$_2$—CH$_2$O)$_3$](Me)(MeO)Si(CH$_2$)$_3$]—SH,
[[C$_{18}$H$_{37}$O—(CH$_2$—CH$_2$O)$_4$](Me)(MeO)Si(CH$_2$)$_3$]—SH,
[[C$_{18}$H$_{37}$O—(CH$_2$—C$_{1-12}$O)$_5$](Me)(MeO)Si(CH$_2$)$_3$]—SH,
[[C$_{18}$H$_{37}$O—(CH$_2$—CH$_2$O)$_6$](Me)(MeO)Si(CH$_2$)$_3$]—SH,
[[C$_3$H$_7$O—(CH$_2$—CH$_2$O)$_2$](Me)(EtO)Si(CH$_2$)$_3$]—SH,
[[C$_3$H$_7$O—(CH$_2$—CH$_2$O)$_3$](Me)(EtO)Si(CH$_2$)$_3$]—SH,
[[C$_3$H$_7$O—(CH$_2$—CH$_2$O)$_4$](Me)(EtO)Si(CH$_2$)$_3$]—SH,
[[C$_3$H$_7$O—(CH$_2$—CH$_2$O)$_5$](Me)(EtO)Si(CH$_2$)$_3$]—SH,
[[C$_3$H$_7$O—(CH$_2$—CH$_2$O)$_6$](Me)(EtO)Si(CH$_2$)$_3$]—SH,
[[C$_4$H$_9$O—(CH$_2$—CH$_2$O)$_2$](Me)(EtO)Si(CH$_2$)$_3$]—SH,
[[C$_4$H$_9$O—(CH$_2$—CH$_2$O)$_3$](Me)(EtO)Si(CH$_2$)$_3$]—SH,
[[C$_4$H$_9$O—(CH$_2$—CH$_2$O)$_4$](Me)(EtO)Si(CH$_2$)$_3$]—SH,
[[C$_4$H$_9$O—(CH$_2$—CH$_2$O)$_5$](Me)(EtO)Si(CH$_2$)$_3$]—SH,
[[C$_4$H$_9$O—(CH$_2$—CH$_2$O)$_6$](Me)(EtO)Si(CH$_2$)$_3$]—SH,
[[C$_5$H$_{11}$O—(CH$_2$—CH$_2$O)$_2$](Me)(EtO)Si(CH$_2$)$_3$]—SH,
[[C$_5$H$_{11}$O—(CH$_2$—CH$_2$O)$_3$](Me)(EtO)Si(CH$_2$)$_3$]—SH,
[[C$_5$H$_{11}$O—(CH$_2$—CH$_2$O)$_4$](Me)(EtO)Si(CH$_2$)$_3$]—SH,
[[C$_5$H$_{11}$O—(CH$_2$—CH$_2$O)$_5$](Me)(EtO)Si(CH$_2$)$_3$]—SH,
[[C$_5$H$_{11}$O—(CH$_2$—CH$_2$O)$_6$](Me)(EtO)Si(CH$_2$)$_3$]—SH,
[[C$_6$H$_{13}$O—(CH$_2$—CH$_2$O)$_2$](Me)(EtO)Si(CH$_2$)$_3$]—SH,
[[C$_6$H$_3$O—(CH$_2$—CH$_2$O)$_3$](Me)(EtO)Si(CH$_2$)$_3$]—SH,
[[C$_6$H$_{13}$O—(CH$_2$—CH$_2$O)$_4$](Me)(EtO)Si(CH$_2$)$_3$]—SH,
[[C$_6$H$_{13}$O—(CH$_2$—CH$_2$O)$_5$](Me)(EtO)Si(CH$_2$)$_3$]—SH,
[[C$_6$H$_{13}$O—(CH$_2$—CH$_2$O)$_6$](Me)(EtO)Si(CH$_2$)$_3$]—SH,
[[C$_7$H$_{15}$O—(CH$_2$—CH$_2$O)$_2$](Me)(EtO)Si(CH$_2$)$_3$]—SH,
[[C$_7$H$_{15}$O—(CH$_2$—CH$_2$O)$_3$](Me)(EtO)Si(CH$_2$)$_3$]—SH,
[[C$_7$H$_{15}$O—(CH$_2$—CH$_2$O)$_4$](Me)(EtO)Si(CH$_2$)$_3$]—SH,
[[C$_7$H$_5$O—(CH$_2$—CH$_2$O)$_5$](Me)(EtO)Si(CH$_2$)$_3$]—SH,
[[C$_7$H$_{15}$O—(CH$_2$—CH$_2$O)$_6$](Me)(EtO)Si(CH$_2$)$_3$]—SH,
[[C$_8$H$_{17}$O—(CH$_2$—CH$_2$O)$_2$](Me)(EtO)Si(CH$_2$)$_3$]—SH,
[[C$_8$H$_{17}$O—(CH$_2$—CH$_2$O)$_3$](Me)(EtO)Si(CH$_2$)$_3$]—SH,
[[C$_8$H$_{17}$O—(CH$_2$—CH$_2$O)$_4$](Me)(EtO)Si(CH$_2$)$_3$]—SH,
[[C$_8$H$_{17}$O—(CH$_2$—CH$_2$O)$_5$](Me)(EtO)Si(CH$_2$)$_3$]—SH,
[[C$_8$H$_{17}$O—(CH$_2$—CH$_2$O)$_6$](Me)(EtO)Si(CH$_2$)$_3$]—SH,
[[C$_9$H$_{19}$O—(CH$_2$—CH$_2$O)$_2$](Me)(EtO)Si(CH$_2$)$_3$]—SH,
[[C$_9$H$_{19}$O—(CH$_2$—CH$_2$O)$_3$](Me)(EtO)Si(CH$_2$)$_3$]—SH,
[[C$_9$H$_{19}$O—(CH$_2$—CH$_2$O)$_4$](Me)(EtO)Si(CH$_2$)$_3$]—SH,
[[C$_9$H$_{19}$O—(CH$_2$—CH$_2$O)$_5$](Me)(EtO)Si(CH$_2$)$_3$]—SH,
[[C$_9$H$_{19}$O—(CH$_2$—CH$_2$O)$_6$](Me)(EtO)Si(CH$_2$)$_3$]—SH,
[[C$_{10}$H$_{21}$O—(CH$_2$—CH$_2$O)$_2$](Me)(EtO)Si(CH$_2$)$_3$]—SH,
[[C$_{10}$H$_{21}$O—(CH$_2$—CH$_2$O)$_3$](Me)(EtO)Si(CH$_2$)$_3$]—SH,
[[C$_{10}$H$_{21}$O—(CH$_2$—CH$_2$O)$_4$](Me)(EtO)Si(CH$_2$)$_3$]—SH,
[[C$_{10}$H$_{21}$O—(CH$_2$—CH$_2$O)$_5$](Me)(EtO)Si(CH$_2$)$_3$]—SH,
[[C$_{10}$H$_{21}$O—(CH$_2$—CH$_2$O)$_6$](Me)(EtO)Si(CH$_2$)$_3$]—SH,
[[C$_{11}$H$_{23}$O—(CH$_2$—CH$_2$O)$_2$](Me)(EtO)Si(CH$_2$)$_3$]—SH,
[[C$_{11}$H$_{23}$O—(CH$_2$—CH$_2$O)$_3$](Me)(EtO)Si(CH$_2$)$_3$]—SH,
[[C$_{11}$H$_{23}$O—(CH$_2$—CH$_2$O)$_4$](Me)(EtO)Si(CH$_2$)$_3$]—SH,
[[C$_{11}$H$_{23}$O—(CH$_2$—CH$_2$O)$_5$](Me)(EtO)Si(CH$_2$)$_3$]—SH,
[[C$_{11}$H$_{23}$O—(CH$_2$—CH$_2$O)$_6$](Me)(EtO)Si(CH$_2$)$_3$]—SH,
[[C$_{12}$H$_{25}$O—(CH$_2$—CH$_2$O)$_2$](Me)(EtO)Si(CH$_2$)$_3$]—SH,
[[C$_{12}$H$_{25}$O—(CH$_2$—CH$_2$O)$_3$](Me)(EtO)Si(CH$_2$)$_3$]—SH,
[[C$_{12}$H$_{25}$O—(CH$_2$—CH$_2$O)$_4$](Me)(EtO)Si(CH$_2$)$_3$]—SH,
[[C$_{12}$H$_{25}$O—(CH$_2$—CH$_2$O)$_5$](Me)(EtO)Si(CH$_2$)$_3$]—SH,
[[C$_{12}$H$_{25}$O—(CH$_2$—CH$_2$O)$_6$](Me)(EtO)Si(CH$_2$)$_3$]—SH,
[[C$_{13}$H$_{27}$O—(CH$_2$—CH$_2$O)$_2$](Me)(EtO)Si(CH$_2$)$_3$]—SH,
[[C$_{13}$H$_{27}$O—(CH$_2$—CH$_2$O)$_3$](Me)(EtO)Si(CH$_2$)$_3$]—SH,
[[C$_{13}$H$_{27}$O—(CH$_2$—CH$_2$O)$_4$](Me)(EtO)Si(CH$_2$)$_3$]—SH,
[[C$_{13}$H$_{27}$O—(CH$_2$—CH$_2$O)$_5$](Me)(EtO)Si(CH$_2$)$_3$]—SH,
[[C$_{13}$H$_{27}$O—(CH$_2$—CH$_2$O)$_6$](Me)(EtO)Si(CH$_2$)$_3$]—SH,
[[C$_{14}$H$_{29}$O—(CH$_2$—CH$_2$O)$_2$](Me)(EtO)Si(CH$_2$)$_3$]—SH,
[[C$_{14}$H$_{29}$O—(CH$_2$—CH$_2$O)$_3$](Me)(EtO)Si(CH$_2$)$_3$]—SH,
[[C$_{14}$H$_{29}$O—(CH$_2$—CH$_2$O)$_4$](Me)(EtO)Si(CH$_2$)$_3$]—SH,
[[C$_{14}$H$_{29}$O—(CH$_2$—CH$_2$O)$_5$](Me)(EtO)Si(CH$_2$)$_3$]—SH,
[[C$_{14}$H$_{29}$O—(CH$_2$—CH$_2$O)$_6$](Me)(EtO)Si(CH$_2$)$_3$]—SH,
[[C$_{15}$H$_{31}$O—(CH$_2$—CH$_2$O)$_2$](Me)(EtO)Si(CH$_2$)$_3$]—SH,
[[C$_{15}$H$_{31}$O—(CH$_2$—CH$_2$O)$_3$](Me)(EtO)Si(CH$_2$)$_3$]—SH,
[[C$_{15}$H$_{31}$O—(CH$_2$—CH$_2$O)$_4$](Me)(EtO)Si(CH$_2$)$_3$]—SH,
[[C$_{15}$H$_{31}$O—(CH$_2$—CH$_2$O)$_5$](Me)(EtO)Si(CH$_2$)$_3$]—SH,
[[C$_{15}$H$_{31}$O—(CH$_2$—CH$_2$O)$_6$](Me)(EtO)Si(CH$_2$)$_3$]—SH,
[[C$_{16}$H$_{33}$O—(CH$_2$—CH$_2$O)$_2$](Me)(EtO)Si(CH$_2$)$_3$]—SH,
[[C$_{16}$H$_{33}$O—(CH$_2$—CH$_2$O)$_3$](Me)(EtO)Si(CH$_2$)$_3$]—SH,
[[C$_{16}$H$_{33}$O—(CH$_2$—CH$_2$O)$_4$](Me)(EtO)Si(CH$_2$)$_3$]—SH,
[[C$_{16}$H$_{33}$O—(CH$_2$—CH$_2$O)$_5$](Me)(EtO)Si(CH$_2$)$_3$]—SH,
[[C$_{16}$H$_{33}$O—(CH$_2$—CH$_2$O)$_6$](Me)(EtO)Si(CH$_2$)$_3$]—SH,
[[C$_{17}$H$_{35}$O—(CH$_2$—CH$_2$O)$_2$](Me)(EtO)Si(CH$_2$)$_3$]—SH,
[[C$_{17}$H$_{35}$O—(CH$_2$—CH$_2$O)$_3$](Me)(EtO)Si(CH$_2$)$_3$]—SH,
[[C$_{17}$H$_{35}$O—(CH$_2$—CH$_2$O)$_4$](Me)(EtO)Si(CH$_2$)$_3$]—SH,
[[C$_{17}$H$_{35}$O—(CH$_2$—CH$_2$O)$_5$](Me)(EtO)Si(CH$_2$)$_3$]—SH,
[[C$_{17}$H$_{35}$O—(CH$_2$—CH$_2$O)$_6$](Me)(EtO)Si(CH$_2$)$_3$]—SH,
[[C$_{18}$H$_{37}$O—(CH$_2$—CH$_2$O)$_2$](Me)(EtO)Si(CH$_2$)$_3$]—SH,
[[C$_{18}$H$_{37}$O—(CH$_2$—CH$_2$O)$_3$](Me)(EtO)Si(CH$_2$)$_3$]—SH,
[[C$_{18}$H$_{37}$O—(CH$_2$—CH$_2$O)$_4$](Me)(EtO)Si(CH$_2$)$_3$]—SH,
[[C$_{18}$H$_{37}$O—(CH$_2$—CH$_2$O)$_5$](Me)(EtO)Si(CH$_2$)$_3$]—SH,
[[C$_3$H$_7$O—(CH$_2$—CH$_2$O)$_2$](MeO)$_2$Si(CH$_2$)$_3$]—SH,
[[C$_3$H$_7$O—(CH$_2$—CH$_2$O)$_3$](MeO)$_2$Si(CH$_2$)$_3$]—SH,
[[C$_3$H$_7$O—(CH$_2$—CH$_2$O)$_4$](MeO)$_2$Si(CH$_2$)$_3$]—SH,
[[C$_3$H$_7$O—(CH$_2$—CH$_2$O)$_5$](MeO)$_2$Si(CH$_2$)$_3$]—SH,
[[C$_3$H$_7$O—(CH$_2$—CH$_2$O)$_6$](MeO)$_2$Si(CH$_2$)$_3$]—SH,
[[C$_4$H$_9$O—(CH$_2$—CH$_2$O)$_2$](MeO)$_2$Si(CH$_2$)$_3$]—SH,
[[C$_4$H$_9$O—(CH$_2$—CH$_2$O)$_3$](MeO)$_2$Si(CH$_2$)$_3$]—SH,
[[C$_4$H$_9$O—(CH$_2$—CH$_2$O)$_4$](MeO)$_2$Si(CH$_2$)$_3$]—SH,
[[C$_4$H$_9$O—(CH$_2$—CH$_2$O)$_5$](MeO)$_2$Si(CH$_2$)$_3$]—SH,
[[C$_4$H$_9$O—(CH$_2$—CH$_2$O)$_6$](MeO)$_2$Si(CH$_2$)$_3$]—SH,
[[C$_5$H$_{11}$O—(CH$_2$—CH$_2$O)$_2$](MeO)$_2$Si(CH$_2$)$_3$]—SH,
[[C$_5$H$_{11}$O—(CH$_2$—CH$_2$O)$_3$](MeO)$_2$Si(CH$_2$)$_3$]—SH,
[[C$_5$H$_{11}$O—(CH$_2$—CH$_2$O)$_4$](MeO)$_2$Si(CH$_2$)$_3$]—SH,
[[C$_5$H$_{11}$O—(CH$_2$—CH$_2$O)$_5$](MeO)$_2$Si(CH$_2$)$_3$]—SH,
[[C$_5$H$_{11}$O—(CH$_2$—CH$_2$O)$_6$](MeO)$_2$Si(CH$_2$)$_3$]—SH,
[[C$_6$H$_{13}$O—(CH$_2$—CH$_2$O)$_2$](MeO)$_2$Si(CH$_2$)$_3$]—SH,
[[C$_6$H$_3$O—(CH$_2$—CH$_2$O)$_3$](MeO)$_2$Si(CH$_2$)$_3$]—SH,
[[C$_6$H$_3$O—(CH$_2$—CH$_2$O)$_4$](MeO)$_2$Si(CH$_2$)$_3$]—SH,
[[C$_6$H$_3$O—(CH$_2$—CH$_2$O)$_5$](MeO)$_2$Si(CH$_2$)$_3$]—SH,
[[C$_6$H$_{13}$O—(CH$_2$—CH$_2$O)$_6$](MeO)$_2$Si(CH$_2$)$_3$]—SH,
[[C$_7$H$_{15}$O—(CH$_2$—CH$_2$O)$_2$](MeO)$_2$Si(CH$_2$)$_3$]—SH,
[[C$_7$H$_5$O—(CH$_2$—CH$_2$O)$_3$](MeO)$_2$Si(CH$_2$)$_3$]—SH,
[[C$_7$H$_5$O—(CH$_2$—CH$_2$O)$_4$](MeO)$_2$Si(CH$_2$)$_3$]—SH,
[[C$_7$H$_{15}$O—(CH$_2$—CH$_2$O)$_5$](MeO)$_2$Si(CH$_2$)$_3$]—SH,
[[C$_7$H$_{15}$O—(CH$_2$—CH$_2$O)$_6$](MeO)$_2$Si(CH$_2$)$_3$]—SH,
[[C$_8$H$_{17}$O—(CH$_2$—CH$_2$O)$_2$](MeO)$_2$Si(CH$_2$)$_3$]—SH,
[[C$_8$H$_{17}$O—(CH$_2$—CH$_2$O)$_3$](MeO)$_2$Si(CH$_2$)$_3$]—SH,
[[C$_8$H$_{17}$O—(CH$_2$—CH$_2$O)$_4$](MeO)$_2$Si(CH$_2$)$_3$]—SH,
[[C$_8$H$_{17}$O—(CH$_2$—CH$_2$O)$_5$](MeO)$_2$Si(CH$_2$)$_3$]—SH,
[[C$_8$H$_7$O—(CH$_2$—CH$_2$O)$_6$](MeO)$_2$Si(CH$_2$)$_3$]—SH,
[[C$_9$H$_{19}$O—(CH$_2$—CH$_2$O)$_2$](MeO)$_2$Si(CH$_2$)$_3$]—SH,
[[C$_9$H$_{19}$O—(CH$_2$—CH$_2$O)$_3$](MeO)$_2$Si(CH$_2$)$_3$]—SH,
[[C$_9$H$_{19}$O—(CH$_2$—CH$_2$O)$_4$](MeO)$_2$Si(CH$_2$)$_3$]—SH,
[[C$_9$H$_{19}$O—(CH$_2$—CH$_2$O)$_5$](MeO)$_2$Si(CH$_2$)$_3$]—SH,
[[C$_9$H$_{19}$O—(CH$_2$—CH$_2$O)$_6$](MeO)$_2$Si(CH$_2$)$_3$]—SH,
[[C$_{10}$H$_{21}$O—(CH$_2$—CH$_2$O)$_2$](MeO)$_2$Si(CH$_2$)$_3$]—SH,
[[C$_{10}$H$_{21}$O—(CH$_2$—CH$_2$O)$_3$](MeO)$_2$Si(CH$_2$)$_3$]—SH,
[[C$_{10}$H$_{21}$O—(CH$_2$—CH$_2$O)$_4$](MeO)$_2$Si(CH$_2$)$_3$]—SH,
[[C$_{10}$H$_{21}$O—(CH$_2$—CH$_2$O)$_5$](MeO)$_2$Si(CH$_2$)$_3$]—SH,
[[C$_{10}$H$_{21}$O—(CH$_2$—CH$_2$O)$_6$](MeO)$_2$Si(CH$_2$)$_3$]—SH,
[[C$_{11}$H$_{23}$O—(CH$_2$—CH$_2$O)$_2$](MeO)$_2$Si(CH$_2$)$_3$]—SH,
[[C$_{11}$H$_{23}$O—(CH$_2$—CH$_2$O)$_3$](MeO)$_2$Si(CH$_2$)$_3$]—SH,
[[C$_{11}$H$_{23}$O—(CH$_2$—CH$_2$O)$_4$](MeO)$_2$Si(CH$_2$)$_3$]—SH,
[[C$_{11}$H$_{23}$O—(CH$_2$—CH$_2$O)$_5$](MeO)$_2$Si(CH$_2$)$_3$]—SH,
[[C$_{11}$H$_{23}$O—(CH$_2$—CH$_2$O)$_6$](MeO)$_2$Si(CH$_2$)$_3$]—SH,
[[C$_{12}$H$_{25}$O—(CH$_2$—CH$_2$O)$_2$](MeO)$_2$Si(CH$_2$)$_3$]—SH,
[[C$_{12}$H$_{25}$O—(CH$_2$—CH$_2$O)$_3$](MeO)$_2$Si(CH$_2$)$_3$]—SH,
[[C$_{12}$H$_{25}$O—(CH$_2$—CH$_2$O)$_4$](MeO)$_2$Si(CH$_2$)$_3$]—SH,
[[C$_{12}$H$_{25}$O—(CH$_2$—CH$_2$O)$_5$](MeO)$_2$Si(CH$_2$)$_3$]—SH,
[[C$_{12}$H$_{25}$O—(CH$_2$—CH$_2$O)$_6$](MeO)$_2$Si(CH$_2$)$_3$]—SH,

[[C$_{13}$H$_{27}$O—(CH$_2$—CH$_2$O)$_2$](MeO)$_2$Si(CH$_2$)$_3$]—SH,
[[C$_{13}$H$_{27}$O—(CH$_2$—CH$_2$O)$_3$](MeO)$_2$Si(CH$_2$)$_3$]—SH,
[[C$_{13}$H$_{27}$O—(CH$_2$—CH$_2$O)$_4$](MeO)$_2$Si(CH$_2$)$_3$]—SH,
[[C$_{13}$H$_{27}$O—(CH$_2$—CH$_2$O)$_5$](MeO)$_2$Si(CH$_2$)$_3$]—SH,
[[C$_{13}$H$_{27}$O—(CH$_2$—CH$_2$O)$_6$](MeO)$_2$Si(CH$_2$)$_3$]—SH,
[[C$_{14}$H$_{29}$O—(CH$_2$—CH$_2$O)$_2$](MeO)$_2$Si(CH$_2$)$_3$]—SH,
[[C$_{14}$H$_{29}$O—(CH$_2$—CH$_2$O)$_3$](MeO)$_2$Si(CH$_2$)$_3$]—SH,
[[C$_{14}$H$_{29}$O—(CH$_2$—CH$_2$O)$_4$](MeO)$_2$Si(CH$_2$)$_3$]—SH,
[[C$_{14}$H$_{29}$O—(CH$_2$—CH$_2$O)$_5$](MeO)$_2$Si(CH$_2$)$_3$]—SH,
[[C$_{14}$H$_{29}$O—(CH$_2$—CH$_2$O)$_6$](MeO)$_2$Si(CH$_2$)$_3$]—SH,
[[C$_{16}$H$_{33}$O—(CH$_2$—CH$_2$O)$_2$](MeO)$_2$Si(CH$_2$)$_3$]—SH,
[[C$_{16}$H$_{33}$O—(CH$_2$—CH$_2$O)$_3$](MeO)$_2$Si(CH$_2$)$_3$]—SH,
[[C$_{16}$H$_{33}$O—(CH$_2$—CH$_2$O)$_4$](MeO)$_2$Si(CH$_2$)$_3$]—SH,
[[C$_{16}$H$_{33}$O—(CH$_2$—CH$_2$O)$_5$](MeO)$_2$Si(CH$_2$)$_3$]—SH,
[[C$_{16}$H$_{33}$O—(CH$_2$—CH$_2$O)$_6$](MeO)$_2$Si(CH$_2$)$_3$]—SH,
[[C$_{18}$H$_{37}$O—(CH$_2$—CH$_2$O)$_2$](MeO)$_2$Si(CH$_2$)$_3$]—SH,
[[C$_{18}$H$_{37}$O—(CH$_2$—CH$_2$O)$_3$](MeO)$_2$Si(CH$_2$)$_3$]—SH,
[[C$_{18}$H$_{37}$O—(CH$_2$—CH$_2$O)$_4$](MeO)$_2$Si(CH$_2$)$_3$]—SH,
[[C$_{18}$H$_{37}$O—(CH$_2$—CH$_2$O)$_5$](MeO)$_2$Si(CH$_2$)$_3$]—SH,
[[C$_{18}$H$_{37}$O—(CH$_2$—CH$_2$O)$_6$](MeO)$_2$Si(CH$_2$)$_3$]—SH,
[[C$_3$H$_7$O—(CH$_2$—CH$_2$O)$_2$]$_2$(MeO)Si(CH$_2$)$_3$]—SH,
[[C$_3$H$_7$O—(CH$_2$—CH$_2$O)$_3$]$_2$(MeO)Si(CH$_2$)$_3$]—SH,
[[C$_3$H$_7$O—(CH$_2$—CH$_2$O)$_4$]$_2$(MeO)Si(CH$_2$)$_3$]—SH,
[[C$_3$H$_7$O—(CH$_2$—CH$_2$O)$_5$]$_2$(MeO)Si(CH$_2$)$_3$]—SH,
[[C$_3$H$_7$O—(CH$_2$—CH$_2$O)$_6$]$_2$(MeO)Si(CH$_2$)$_3$]—SH,
[[C$_4$H$_9$O—(CH$_2$—CH$_2$O)$_2$]$_2$(MeO)Si(CH$_2$)$_3$]—SH,
[[C$_4$H$_9$O—(CH$_2$—CH$_2$O)$_3$]$_2$(MeO)Si(CH$_2$)$_3$]—SH,
[[C$_4$H$_9$O—(CH$_2$—CH$_2$O)$_4$]$_2$(MeO)Si(CH$_2$)$_3$]—SH,
[[C$_4$H$_9$O—(CH$_2$—CH$_2$O)$_5$]$_2$(MeO)Si(CH$_2$)$_3$]—SH,
[[C$_4$H$_9$O—(CH$_2$—CH$_2$O)$_6$]$_2$(MeO)Si(CH$_2$)$_3$]—SH,
[[C$_5$H$_{11}$O—(CH$_2$—CH$_2$O)$_2$]$_2$(MeO)Si(CH$_2$)$_3$]—SH,
[[C$_5$H$_{11}$O—(CH$_2$—CH$_2$O)$_3$]$_2$(MeO)Si(CH$_2$)$_3$]—SH,
[[C$_5$H$_1$O—(CH$_2$—CH$_2$O)$_4$]$_2$(MeO)Si(CH$_2$)$_3$]—SH,
[[C$_5$H$_{11}$O—(CH$_2$—CH$_2$O)$_5$]$_2$(MeO)Si(CH$_2$)$_3$]—SH,
[[C$_5$H$_{11}$O—(CH$_2$—CH$_2$O)$_6$]$_2$(MeO)Si(CH$_2$)$_3$]—SH,
[[C$_6$H$_{13}$O—(CH$_2$—CH$_2$O)$_2$]$_2$(MeO)Si(CH$_2$)$_3$]—SH,
[[C$_6$H$_{13}$O—(CH$_2$—CH$_2$O)$_3$]$_2$(MeO)Si(CH$_2$)$_3$]—SH,
[[C$_6$H$_{13}$O—(CH$_2$—CH$_2$O)$_4$]$_2$(MeO)Si(CH$_2$)$_3$]—SH,
[[C$_6$H$_{13}$O—(CH$_2$—CH$_2$O)$_5$]$_2$(MeO)Si(CH$_2$)$_3$]—SH,
[[C$_6$H$_{13}$O—(CH$_2$—CH$_2$O)$_6$]$_2$(MeO)Si(CH$_2$)$_3$]—SH,
[[C$_7$H$_{15}$O—(CH$_2$—CH$_2$O)$_2$]$_2$(MeO)Si(CH$_2$)$_3$]—SH,
[[C$_7$H$_{15}$O—(CH$_2$—CH$_2$O)$_3$]$_2$(MeO)Si(CH$_2$)$_3$]—SH,
[[C$_7$H$_{15}$O—(CH$_2$—CH$_2$O)$_4$]$_2$(MeO)Si(CH$_2$)$_3$]—SH,
[[C$_7$H$_{15}$O—(CH$_2$—CH$_2$O)$_5$]$_2$(MeO)Si(CH$_2$)$_3$]—SH,
[[C$_7$H$_{15}$O—(CH$_2$—CH$_2$O)$_6$]$_2$(MeO)Si(CH$_2$)$_3$]—SH,
[[C$_8$H$_{17}$O—(CH$_2$—CH$_2$O)$_2$]$_2$(MeO)Si(CH$_2$)$_3$]—SH,
[[C$_8$H$_{17}$O—(CH$_2$—CH$_2$O)$_3$]$_2$(MeO)Si(CH$_2$)$_3$]—SH,
[[C$_8$H$_{17}$O—(CH$_2$—CH$_2$O)$_4$]$_2$(MeO)Si(CH$_2$)$_3$]—SH,
[[C$_8$H$_{17}$O—CH$_2$—CH$_2$O)$_5$]$_2$(MeO)Si(CH$_2$)$_3$]—SH,
[[C$_8$H$_{17}$O—(CH$_2$—CH$_2$O)$_6$]$_2$(MeO)Si(CH$_2$)$_3$]—SH,
[[C$_9$H$_{19}$O—(CH$_2$—CH$_2$O)$_2$]$_2$(MeO)Si(CH$_2$)$_3$]—SH,
[[C$_9$H$_{19}$O—(CH$_2$—CH$_2$O)$_3$]$_2$(MeO)Si(CH$_2$)$_3$]—SH,
[[C$_9$H$_{19}$O—(CH$_2$—CH$_2$O)$_4$]$_2$(MeO)Si(CH$_2$)$_3$]—SH,
[[C$_9$H$_{19}$O—(CH$_2$—CH$_2$O)$_5$]$_2$(MeO)Si(CH$_2$)$_3$]—SH,
[[C$_9$H$_{19}$O—(CH$_2$—CH$_2$O)$_6$]$_2$(MeO)Si(CH$_2$)$_3$]—SH,
[[C$_{10}$H$_{21}$O—(CH$_2$—CH$_2$O)$_2$]$_2$(MeO)Si(CH$_2$)$_3$]—SH,
[[C$_{10}$H$_{21}$O—(CH$_2$—CH$_2$O)$_3$]$_2$(MeO)Si(CH$_2$)$_3$]—SH,
[[C$_{10}$H$_{21}$O—(CH$_2$—CH$_2$O)$_4$]$_2$(MeO)Si(CH$_2$)$_3$]—SH,
[[C$_{10}$H$_{21}$O—(CH$_2$—CH$_2$O)$_5$]$_2$(MeO)Si(CH$_2$)$_3$]—SH,
[[C$_{10}$H$_{21}$O—(CH$_2$—CH$_2$O)$_6$]$_2$(MeO)Si(CH$_2$)$_3$]—SH,
[[C$_{11}$H$_{23}$—(CH$_2$—CH$_2$O)$_2$]$_2$(MeO)Si(CH$_2$)$_3$]—SH,
[[C$_{11}$H$_{23}$O—(CH$_2$—CH$_2$O)$_3$]$_2$(MeO)Si(CH$_2$)$_3$]—SH,
[[C$_{11}$H$_{23}$—(CH$_2$—CH$_2$O)$_4$]$_2$(MeO)Si(CH$_2$)$_3$]—SH,
[[C$_{11}$H$_{23}$O—(CH$_2$—CH$_2$O)$_5$]$_2$(MeO)Si(CH$_2$)$_3$]—SH,
[[C$_{11}$H$_{23}$O—(CH$_2$—CH$_2$O)$_6$]$_2$(MeO)Si(CH$_2$)$_3$]—SH,
[[C$_{12}$H$_{25}$O—(CH$_2$—CH$_2$O)$_2$]$_2$(MeO)Si(CH$_2$)$_3$]—SH,
[[C$_{12}$H$_{25}$O—(CH$_2$—CH$_2$O)$_3$]$_2$(MeO)Si(CH$_2$)$_3$]—SH,
[[C$_{12}$H$_{25}$O—(CH$_2$—CH$_2$O)$_4$]$_2$(MeO)Si(CH$_2$)$_3$]—SH,
[[C$_{12}$H$_{25}$O—(CH$_2$—CH$_2$O)$_5$]$_2$(MeO)Si(CH$_2$)$_3$]—SH,
[[C$_{12}$H$_{25}$O—(CH$_2$—CH$_2$O)$_6$]$_2$(MeO)Si(CH$_2$)$_3$]—SH,
[[C$_{13}$H$_{27}$O—(CH$_2$—CH$_2$O)$_2$]$_2$(MeO)Si(CH$_2$)$_3$]—SH,
[[C$_{13}$H$_{27}$O—(CH$_2$—CH$_2$O)$_3$]$_2$(MeO)Si(CH$_2$)$_3$]—SH,
[[C$_{13}$H$_{27}$O—(CH$_2$—CH$_2$O)$_4$]$_2$(MeO)Si(CH$_2$)$_3$]—SH,
[[C$_{13}$H$_{27}$O—(CH$_2$—CH$_2$O)$_5$]$_2$(MeO)Si(CH$_2$)$_3$]—SH,
[[C$_{13}$H$_{27}$O—(CH$_2$—CH$_2$O)$_6$]$_2$(MeO)Si(CH$_2$)$_3$]—SH,
[[C$_{14}$H$_{29}$O—(CH$_2$—CH$_2$O)$_2$]$_2$(MeO)Si(CH$_2$)$_3$]—SH,
[[C$_{14}$H$_{29}$O—(CH$_2$—CH$_2$O)$_3$]$_2$(MeO)Si(CH$_2$)$_3$]—SH,
[[C$_{14}$H$_{29}$O—(CH$_2$—CH$_2$O)$_4$]$_2$(MeO)Si(CH$_2$)$_3$]—SH,
[[C$_{14}$H$_{29}$O—(CH$_2$—CH$_2$O)$_5$]$_2$(MeO)Si(CH$_2$)$_3$]—SH,
[[C$_{14}$H$_{29}$O—(CH$_2$—CH$_2$O)$_6$]$_2$(MeO)Si(CH$_2$)$_3$]—SH,
[[C$_{16}$H$_{33}$O—(CH$_2$—CH$_2$O)$_2$]$_2$(MeO)Si(CH$_2$)$_3$]—SH,
[[C$_{16}$H$_{33}$O—(CH$_2$—CH$_2$O)$_3$]$_2$(MeO)Si(CH$_2$)$_3$]—SH,
[[C$_{16}$H$_{33}$O—(CH$_2$—CH$_2$O)$_4$]$_2$(MeO)Si(CH$_2$)$_3$]—SH,
[[C$_{16}$H$_{33}$O—(CH$_2$—CH$_2$O)$_5$]$_2$(MeO)Si(CH$_2$)$_3$]—SH,
[[C$_{16}$H$_{33}$O—(CH$_2$—CH$_2$O)$_6$]$_2$(MeO)Si(CH$_2$)$_3$]—SH,
[[C$_{18}$H$_{37}$O—(CH$_2$—CH$_2$O)$_2$]$_2$(MeO)Si(CH$_2$)$_3$]—SH,
[[C$_{18}$H$_{37}$O—(CH$_2$—CH$_2$O)$_3$]$_2$(MeO)Si(CH$_2$)$_3$]—SH,
[[C$_{18}$H$_{37}$O—(CH$_2$—CH$_2$O)$_4$]$_2$(Mea) Si (CH$_2$)$_3$]—SH,
[[C$_{18}$H$_{37}$O—(CH$_2$—CH$_2$O)$_5$]$_2$(MeO)Si(CH$_2$)$_3$]—SH,
[[C$_{18}$H$_{37}$—(CH$_2$—CH$_2$O)$_6$]$_2$(MeO)Si(CH$_2$)$_3$]—SH,
[[C$_3$H$_7$O—(CH$_2$—CH$_2$O)$_2$](EtO)$_2$Si(CH$_2$)$_3$]—SH,
[[C$_3$H$_7$O—(CH$_2$—CH$_2$O)$_3$](EtO)$_2$Si(CH$_2$)$_3$]—SH,
[[C$_3$H$_7$O—(CH$_2$—CH$_2$O)$_4$](EtO)$_2$Si(CH$_2$)$_3$]—SH,
[[C$_3$H$_7$O—(CH$_2$—CH$_2$O)$_5$](EtO)$_2$Si(CH$_2$)$_3$]—SH,
[[C$_3$H$_7$O—(CH$_2$—CH$_2$O)$_6$](EtO)$_2$Si(CH$_2$)$_3$]—SH,
[[C$_4$H$_9$O—(CH$_2$—CH$_2$O)$_2$](EtO)$_2$Si(CH$_2$)$_3$]—SH,
[[C$_4$H$_9$O—(CH$_2$—CH$_2$O)$_3$](EtO)$_2$Si(CH$_2$)$_3$]—SH,
[[C$_4$H$_9$O—(CH$_2$—CH$_2$O)$_4$](EtO)$_2$Si(CH$_2$)$_3$]—SH,
[[C$_4$H$_9$O—(CH$_2$—CH$_2$O)$_5$](EtO)$_2$Si(CH$_2$)$_3$]—SH,
[[C$_4$H$_9$O—(CH$_2$—CH$_2$O)$_6$](EtO)$_2$Si(CH$_2$)$_3$]—SH,
[[C$_5$H$_{11}$O—(CH$_2$—CH$_2$O)$_2$](EtO)$_2$Si(CH$_2$)$_3$]—SH,
[[C$_5$H$_{11}$O—(CH$_2$—CH$_2$O)$_3$](EtO)$_2$Si(CH$_2$)$_3$]—SH,
[[C$_5$H$_{11}$O—(CH$_2$—CH$_2$O)$_4$](EtO)$_2$Si(CH$_2$)$_3$]—SH,
[[C$_5$H$_{11}$O—(CH$_2$—CH$_2$O)$_5$](EtO)$_2$Si(CH$_2$)$_3$]—SH,
[[C$_5$H$_{11}$O—(CH$_2$—CH$_2$O)$_6$](EtO)$_2$Si(CH$_2$)$_3$]—SH,
[[C$_6$H$_{13}$O—(CH$_2$—CH$_2$O)$_2$](EtO)$_2$Si(CH$_2$)$_3$]—SH,
[[C$_6$H$_{13}$O—(CH$_2$—CH$_2$O)$_3$](EtO)$_2$Si(CH$_2$)$_3$]—SH,
[[C$_6$H$_{13}$O—(CH$_2$—CH$_2$O)$_4$](EtO)$_2$Si(CH$_2$)$_3$]—SH,
[[C$_6$H$_{13}$O—(CH$_2$—CH$_2$O)$_5$](EtO)$_2$Si(CH$_2$)$_3$]—SH,
[[C$_6$H$_3$O—(CH$_2$—CH$_2$O)$_6$](EtO)$_2$Si(CH$_2$)$_3$]—SH,
[[C$_7$H$_{15}$O—(CH$_2$—CH$_2$O)$_2$](EtO)$_2$Si(CH$_2$)$_3$]—SH,
[[C$_7$H$_{15}$O—(CH$_2$—CH$_2$O)$_3$](EtO)$_2$Si(CH$_2$)$_3$]—SH,
[[C$_7$H$_{15}$O—(CH$_2$—CH$_2$O)$_4$](Eta)$_2$Si (CH$_2$)$_3$]—SH,
[[C$_7$H$_{15}$O—(CH$_2$—CH$_2$O)$_5$](Eta)$_2$Si (CH$_2$)$_3$]—SH,
[[C$_7$H$_{15}$O—(CH$_2$—CH$_2$O)$_6$](EtO)$_2$Si(CH$_2$)$_3$]—SH,
[[C$_8$H$_{17}$O—(CH$_2$—CH$_2$O)$_2$](EtO)$_2$Si(CH$_2$)$_3$]—SH,
[[C$_8$H$_{17}$O—(CH$_2$—CH$_2$O)$_3$](EtO)$_2$Si(CH$_2$)$_3$]—SH,
[[C$_8$H$_{17}$O—(CH$_2$—CH$_2$O)$_4$](EtO)$_2$Si(CH$_2$)$_3$]—SH,
[[C$_8$H$_{17}$O—(CH$_2$—CH$_2$O)$_5$](EtO)$_2$Si(CH$_2$)$_3$]—SH,
[[C$_8$H$_{17}$O—(CH$_2$—CH$_2$O)$_6$](EtO)$_2$Si(CH$_2$)$_3$]—SH,
[[C$_9$H$_{19}$O—(CH$_2$—CH$_2$O)$_2$](EtO)$_2$Si(CH$_2$)$_3$]—SH,
[[C$_9$H$_{19}$O—(CH$_2$—CH$_2$O)$_3$](EtO)$_2$Si(CH$_2$)$_3$]—SH,
[[C$_9$H$_{19}$O—(CH$_2$—CH$_2$O)$_4$](EtO)$_2$Si(CH$_2$)$_3$]—SH,
[[C$_9$H$_{19}$O—(CH$_2$—CH$_2$O)$_5$](EtO)$_2$Si(CH$_2$)$_3$]—SH,
[[C$_9$H$_{19}$O—(CH$_2$—CH$_2$O)$_6$](EtO)$_2$Si(CH$_2$)$_3$]—SH,
[[C$_{10}$H$_{21}$O—(CH$_2$—CH$_2$O)$_2$](EtO)$_2$Si(CH$_2$)$_3$]—SH,
[[C$_{10}$H$_{21}$O—(CH$_2$—CH$_2$O)$_3$](EtO)$_2$Si(CH$_2$)$_3$]—SH,
[[C$_{10}$H$_{21}$O—(CH$_2$—CH$_2$O)$_4$](EtO)$_2$Si(CH$_2$)$_3$]—SH,
[[C$_{10}$H$_{21}$O—(CH$_2$—CH$_2$O)$_5$](EtO)$_2$Si(CH$_2$)$_3$]—SH,
[[C$_{10}$H$_{21}$O—(CH$_2$—CH$_2$O)$_6$](EtO)$_2$Si(CH$_2$)$_3$]—SH,
[[C$_{11}$H$_{23}$O—(CH$_2$—CH$_2$O)$_2$](EtO)$_2$Si(CH$_2$)$_3$]—SH,
[[C$_{11}$H$_{23}$O—(CH$_2$—CH$_2$O)$_3$](EtO)$_2$Si(CH$_2$)$_3$]—SH,
[[C$_{11}$H$_{23}$O—(CH$_2$—CH$_2$O)$_4$](EtO)$_2$Si(CH$_2$)$_3$]—SH,

[[C₁₁H₂₃O—(CH₂—CH₂O)₅](EtO)₂Si(CH₂)₃]—SH,
[[C₁₁H₂₃O—(CH₂—CH₂O)₆](EtO)₂Si(CH₂)₃]—SH,
[[C₁₂H₂₅O—(CH₂—CH₂O)₂](EtO)₂Si(CH₂)₃]—SH,
[[C₁₂H₂₅O—(CH₂—CH₂O)₃](EtO)₂Si(CH₂)₃]—SH,
[[C₁₂H₂₅O—(CH₂—CH₂O)₄](EtO)₂Si(CH₂)₃]—SH,
[[C₁₂H₂₅O—(CH₂—CH₂O)₅](EtO)₂Si(CH₂)₃]—SH,
[[C₁₂H₂₅O—(CH₂—CH₂O)₆](EtO)₂Si(CH₂)₃]—SH,
[[C₁₃H₂₇O—(CH₂—CH₂O)₂](EtO)₂Si(CH₂)₃]—SH,
[[C₁₃H₂₇O—(CH₂—CH₂O)₃](EtO)₂Si(CH₂)₃]—SH,
[[C₁₃H₂₇O—(CH₂—CH₂O)₄](EtO)₂Si(CH₂)₃]—SH,
[[C₁₃H₂₇O—(CH₂—CH₂O)₅](EtO)₂Si(CH₂)₃]—SH,
[[C₁₃H₂₇O—(CH₂—CH₂O)₆](EtO)₂Si(CH₂)₃]—SH,
[[C₁₄H₂₉O—(CH₂—CH₂O)₂](EtO)₂Si(CH₂)₃]—SH,
[[C₁₄H₂₉O—(CH₂—CH₂O)₃](EtO)₂Si(CH₂)₃]—SH,
[[C₁₄H₂₉O—(CH₂—CH₂O)₄](EtO)₂Si(CH₂)₃]—SH,
[[C₁₄H₂₉O—(CH₂—CH₂O)₅](EtO)₂Si(CH₂)₃]—SH,
[[C₁₄H₂₉O—(CH₂—CH₂O)₆](EtO)₂Si(CH₂)₃]—SH,
[[C₁₆H₃₃O—(CH₂—CH₂O)₂](EtO)₂Si(CH₂)₃]—SH,
[[C₁₆H₃₃O—(CH₂—CH₂O)₃](EtO)₂Si(CH₂)₃]—SH,
[[C₁₆H₃₃O—(CH₂—CH₂O)₄](EtO)₂Si(CH₂)₃]—SH,
[[C₁₆H₃₃O—(CH₂—CH₂O)₅](EtO)₂Si(CH₂)₃]—SH,
[[C₁₆H₃₃O—(CH₂—CH₂O)₆](EtO)₂Si(CH₂)₃]—SH,
[[C₁₇H₃₅O—(CH₂—CH₂O)₂](EtO)₂Si(CH₂)₃]—SH,
[[C₁₇H₃₆O—(CH₂—CH₂O)₃](EtO)₂Si(CH₂)₃]—SH,
[[C₁₇H₃₆O—(CH₂—CH₂O)₄](EtO)₂Si(CH₂)₃]—SH,
[[C₁₇H₃₆O—(CH₂—CH₂O)₅](EtO)₂Si(CH₂)₃]—SH,
[[C₁₇H₃₆O—(CH₂—CH₂O)₆](EtO)₂Si(CH₂)₃]—SH,
[[C₁₈H₃₇O—(CH₂—CH₂O)₂](EtO)₂Si(CH₂)₃]—SH,
[[C₁₈H₃₇O—(CH₂—CH₂O)₃](EtO)₂Si(CH₂)₃]—SH,
[[C₁₈H₃₇O—(CH₂—CH₂O)₄](EtO)₂Si(CH₂)₃]—SH,
[[C₁₈H₃₇O—(CH₂—CH₂O)₅](EtO)₂Si(CH₂)₃]—SH,
[[C₁₈H₃₇O—(CH₂—CH₂O)₆](EtO)₂Si(CH₂)₃]—SH,
[[C₃H₇O—(CH₂—CH₂O)₂](EtO)Si(CH₂)₃]—SH,
[[C₃H₇O—(CH₂—CH₂O)₃]₂(EtO)Si(CH₂)₃]—SH,
[[C₃H₇O—(CH₂—CH₂O)₄]₂(EtO)Si(CH₂)₃]—SH,
[[C₃H₇O—(CH₂—CH₂O)₅]₂(EtO)Si(CH₂)₃]—SH,
[[C₃H₇O—(CH₂—CH₂O)₆]₂(EtO)Si(CH₂)₃]—SH,
[[C₄H₉O—(CH₂—CH₂O)₂]₂(EtO)Si(CH₂)₃]—SH,
[[C₄H₉O—(CH₂—CH₂O)₃]₂(EtO)Si(CH₂)₃]—SH,
[[C₄H₉O—(CH₂—CH₂O)₄]₂(EtO)Si(CH₂)₃]—SH,
[[C₄H₉O—(CH₂—CH₂O)₅]₂(EtO)Si(CH₂)₃]—SH,
[[C₄H₉O—(CH₂—CH₂O)₆]₂(EtO)Si(CH₂)₃]—SH,
[[C₅H₁₁O—(CH₂—CH₂O)₂]₂(EtO)Si(CH₂)₃]—SH,
[[C₅H₁₁O—(CH₂—CH₂O)₃]₂(EtO)Si(CH₂)₃]—SH,
[[C₅H₁₁—(CH₂—CH₂O)₄]₂(EtO)Si(CH₂)₃]—SH,
[[C₅H₁₁—(CH₂—CH₂O)₅]₂(EtO)Si(CH₂)₃]—SH,
[[C₅H₁₁O—(CH₂—CH₂O)₆]₂(EtO)Si(CH₂)₃]—SH,
[[C₆H₃O—(CH₂—CH₂O)₂]₂(EtO)Si(CH₂)₃]—SH,
[[C₆H₁₃O—(CH₂—CH₂O)₃]₂(EtO)Si(CH₂)₃]—SH,
[[C₆H₁₃O—(CH₂—CH₂O)₄]₂(EtO)Si(CH₂)₃]—SH,
[[C₆H₁₃O—(CH₂—CH₂O)₅]₂(EtO)Si(CH₂)₃]—SH,
[[C₆H₁₃O—(CH₂—CH₂O)₆]₂(EtO)Si(CH₂)₃]—SH,
[[C₇H₁₅O—(CH₂—CH₂O)₂]₂(EtO)Si(CH₂)₃]—SH,
[[C₇H₁₅O—(CH₂—CH₂O)₃]₂(EtO)Si(CH₂)₃]—SH,
[[C₇H₁₅O—(CH₂—CH₂O)₄]₂(EtO)Si(CH₂)₃]—SH,
[[C₇H₁₅O—(CH₂—CH₂O)₅]₂(EtO)Si(CH₂)₃]—SH,
[[C₇H₁₅O—(CH₂—CH₂O)₆]₂(EtO)Si(CH₂)₃]—SH,
[[C₈H₁₇O—(CH₂—CH₂O)₂]₂(EtO)Si(CH₂)₃]—SH,
[[C₈H₁₇O—(CH₂—CH₂O)₃]₂(EtO)Si(CH₂)₃]—SH,
[[C₈H₁₇O—(CH₂—CH₂O)₄]₂(EtO)Si(CH₂)₃]—SH,
[[C₈H₁₇O—(CH₂—CH₂O)₅]₂(EtO)Si(CH₂)₃]—SH,
[[C₈H₁₇O—(CH₂—CH₂O)₆]₂(EtO)Si(CH₂)₃]—SH,
[[C₉H₁₉O—(CH₂—CH₂O)₂]₂(EtO)Si(CH₂)₃]—SH,
[[C₉H₁₉O—(CH₂—CH₂O)₃]₂(EtO)Si(CH₂)₃]—SH,
[[C₉H₁₉O—(CH₂—CH₂O)₄]₂(EtO)Si(CH₂)₃]—SH,
[[C₉H₁₉O—(CH₂—CH₂O)₅]₂(EtO)Si(CH₂)₃]—SH,
[[C₉H₁₉O—(CH₂—CH₂O)₆]₂(EtO)Si(CH₂)₃]—SH,
[[C₁₀H₂₁O—(CH₂—CH₂O)₂]₂(EtO)Si(CH₂)₃]—SH,
[[C₁₀H₂₁O—(CH₂—CH₂O)₃]₂(EtO)Si(CH₂)₃]—SH,
[[C₁₀H₂₁O—(CH₂—CH₂O)₄]₂(EtO)Si(CH₂)₃]—SH,
[[C₁₀H₂₁O—(CH₂—CH₂O)₅]₂(EtO)Si(CH₂)₃]—SH,
[[C₁₀H₂₁O—(CH₂—CH₂O)₆]₂(EtO)Si(CH₂)₃]—SH,
[[C₁₁H₂₃O—(CH₂—CH₂O)₃]₂(EtO)Si(CH₂)₃]—SH,
[[C₁₁H₂₃O—(CH₂—CH₂O)₄]₂(EtO)Si(CH₂)₃]—SH,
[[C₁₁H₂₃O—(CH₂—CH₂O)₅]₂(EtO)Si(CH₂)₃]—SH,
[[C₁₁H₂₃O—(CH₂—CH₂O)₆]₂(EtO)Si(CH₂)₃]—SH,
[[C₁₂H₂₅O—(CH₂—CH₂O)₂]₂(EtO)Si(CH₂)₃]—SH,
[[C₁₂H₂₅O—(CH₂—CH₂O)₃]₂(EtO)Si(CH₂)₃]—SH,
[[C₁₂H₂₅O—(CH₂—CH₂O)₄]₂(EtO)Si(CH₂)₃]—SH,
[[C₁₂H₂₅O—(CH₂—CH₂O)₅]₂(EtO)Si(CH₂)₃]—SH,
[[C₁₂H₂₅O—(CH₂—CH₂O)₆]₂(EtO)Si(CH₂)₃]—SH,
[[C₁₃H₂₇O—(CH₂—CH₂O)₂]₂(EtO)Si(CH₂)₃]—SH,
[[C₁₃H₂₇O—(CH₂—CH₂O)₃]₂(EtO)Si(CH₂)₃]—SH,
[[C₁₃H₂₇O—(CH₂—CH₂O)₄]₂(EtO)Si(CH₂)₃]—SH,
[[C₁₃H₂₇O—(CH₂—CH₂O)₅]₂(EtO)Si(CH₂)₃]—SH,
[[C₁₃H₂₇O—(CH₂—CH₂O)₆]₂(EtO)Si(CH₂)₃]—SH,
[[C₁₄H₂₉O—(CH₂—CH₂O)₂]₂(EtO)Si(CH₂)₃]—SH,
[[C₁₄H₂₉O—(CH₂—CH₂O)₃]₂(EtO)Si(CH₂)₃]—SH,
[[C₁₄H₂₉O—(CH₂—CH₂O)₄]₂(EtO)Si(CH₂)₃]—SH,
[[C₁₄H₂₉O—(CH₂—CH₂O)₅]₂(EtO)Si(CH₂)₃]—SH,
[[C₁₄H₂₉O—(CH₂—CH₂O)₆]₂(EtO)Si(CH₂)₃]—SH,
[[C₁₆H₃₃O—(CH₂—CH₂O)₂]₂(EtO)Si(CH₂)₃]—SH,
[[C₁₆H₃₃O—(CH₂—CH₂O)₃]₂(EtO)Si(CH₂)₃]—SH,
[[C₁₆H₃₃O—(CH₂—CH₂O)₄]₂(EtO)Si(CH₂)₃]—SH,
[[C₁₆H₃₃O—(CH₂—CH₂O)₅]₂(EtO)Si(CH₂)₃]—SH,
[[C₁₆H₃₃O—(CH₂—CH₂O)₆]₂(EtO)Si(CH₂)₃]—SH,
[[C₁₇H₃₅O—(CH₂—CH₂O)₂]₂(EtO)Si(CH₂)₃]—SH,
[[C₁₇H₃₅O—(CH₂—CH₂O)₃]₂(EtO)Si(CH₂)₃]—SH,
[[C₁₇H₃₅O—(CH₂—CH₂O)₄]₂(EtO)Si(CH₂)₃]—SH,
[[C₁₇H₃₅—(CH₂—CH₂O)₅]₂(EtO)Si(CH₂)₃]—SH,
[[C₁₇H₃₅O—(CH₂—CH₂O)₆]₂(EtO)Si(CH₂)₃]—SH,
[[C₁₈H₃₇O—(CH₂—CH₂O)₂]₂(EtO)Si(CH₂)₃]—SH,
[[C₁₈H₃₇O—(CH₂—CH₂O)₃]₂(EtO)Si(CH₂)₃]—SH,
[[C₁₈H₃₇O—(CH₂—CH₂O)₄]₂(EtO)Si(CH₂)₃]—SH,
[[C₁₈H₃₇O—(CH₂—CH₂O)₅]₂(EtO)Si(CH₂)₃]—SH,
[[C₁₈H₃₇O—(CH₂—CH₂O)₆]₂(EtO)Si(CH₂)₃]—SH,
[[C₁₀H₂₁O—(CH₂—CH₂O)₂]₃Si(CH₂)₃]—SH,
[[C₁₀H₂₁O—(CH₂—CH₂O)₃]₃Si(CH₂)₃]—SH,
[[C₁₀H₂₁O—(CH₂—CH₂O)₄]₃Si(CH₂)₃]—SH,
[[C₁₀H₂₁O—(CH₂—CH₂O)₅]₃Si(CH₂)₃]—SH,
[[C₁₀H₂₁O—(CH₂—CH₂O)₆]₃Si(CH₂)₃]—SH,
[[C₁₂H₂₅O—(CH₂—CH₂O)₂]₃Si(CH₂)₃]—SH,
[[C₁₂H₂₆O—(CH₂—CH₂O)₃]₃Si(CH₂)₃]—SH,
[[C₁₂H₂₅O—(CH₂—CH₂O)₄]₃Si(CH₂)₃]—SH,
[[C₁₂H₂₅O—(CH₂—CH₂O)₅]₃Si(CH₂)₃]—SH,
[[C₁₂H₂₅O—(CH₂—CH₂O)₆]₃Si(CH₂)₃]—SH,
[[C₁₃H₂₇O—(CH₂—CH₂O)₂]₃Si(CH₂)₃]—SH,
[[C₁₃H₂₇O—(CH₂—CH₂O)₃]₃Si(CH₂)₃]—SH,
[[C₁₃H₂₇O—(CH₂—CH₂O)₄]₃Si(CH₂)₃]—SH,
[[C₁₃H₂₇O—(CH₂—CH₂O)₅]₃Si(CH₂)₃]—SH,
[[C₁₃H₂₇O—(CH₂—CH₂O)₆]₃Si(CH₂)₃]—SH,
[[C₁₄H₂₉O—(CH₂—CH₂O)₂]₃Si(CH₂)₃]—SH,
[[C₁₄H₂₉O—(CH₂—CH₂O)₃]₃Si(CH₂)₃]—SH,
[[C₁₄H₂₉O—(CH₂—CH₂O)₄]₃Si(CH₂)₃]—SH,
[[C₁₄H₂₉O—(CH₂—CH₂O)₅]₃Si(CH₂)₃]—SH,
[[C₁₄H₂₉O—(CH₂—CH₂O)₆]₃Si(CH₂)₃]—SH,
[[C₁₅H₃₁O—(CH₂—CH₂O)₂]₃Si(CH₂)₃]—SH,
[[C₁₆H₃₁O—(CH₂—CH₂O)₃]₃Si(CH₂)₃]—SH,
[[C₁₅H₃₁O—(CH₂—CH₂O)₄]₃Si(CH₂)₃]—SH,
[[C₁₅H₃₁O—(CH₂—CH₂O)₅]₃Si(CH₂)₃]—SH,
[[C₁₆H₃₁O—(CH₂—CH₂O)₆]₃Si(CH₂)₃]—SH,
[[C₁₆H₃₃O—(CH₂—CH₂O)₂]₃Si(CH₂)₃]—SH,
[[C₁₆H₃₃O—(CH₂—CH₂O)₃]₃Si(CH₂)₃]—SH,

[[C$_{16}$H$_{33}$O—(CH$_2$—CH$_2$O)$_4$]$_3$Si(CH$_2$)$_3$]—SH,
[[C$_{16}$H$_{33}$O—(CH$_2$—CH$_2$O)$_5$]$_3$Si(CH$_2$)$_3$]—SH,
[[C$_{16}$H$_{33}$O—(CH$_2$—CH$_2$O)$_6$]$_3$Si(CH$_2$)$_3$]—SH,
[[C$_{18}$H$_{37}$O—(CH$_2$—CH$_2$O)$_2$]$_3$Si(CH$_2$)$_3$]—SH,
[[(C$_{18}$H$_{37}$O—(CH$_2$—CH$_2$O)$_3$]$_3$Si(CH$_2$)$_3$]—SH,
[[C$_{18}$H$_{37}$O—(CH$_2$—CH$_2$O)$_4$]$_3$Si(CH$_2$)$_3$]—SH, or
[[C$_{18}$H$_{37}$O—(CH$_2$—CH$_2$O)$_5$]$_3$Si(CH$_2$)$_3$]—SH,
[[C$_{18}$H$_{37}$O—(CH$_2$—CH$_2$O)$_6$]$_3$Si(CH$_2$)$_3$]—SH,
where the alkyl moieties can be unbranched or branched.

Compounds of the formula II, where Alk =C$_3$H$_7$, C$_4$H$_9$, C$_5$H$_{11}$, C$_6$H$_{13}$, C$_7$H$_{15}$, C$_8$H$_{17}$C$_9$H$_{19}$, C$_{10}$H$_{21}$, C$_{11}$H$_{23}$, C$_{12}$H$_{25}$, C$_{13}$H$_{27}$, C$_{14}$H$_{29}$, C$_{15}$H$_{31}$, C$_{16}$H$_{33}$, C$_{17}$H$_{35}$, or C$_{18}$H$_{37}$, can be:
[[Alk-O—(CH$_2$—CH(CH$_3$)O—)$_2$](MeO)$_2$Si(CH$_2$)$_3$]—SH,
[[Alk-O—(CH$_2$—CH(CH$_3$)O—)$_3$](MeO)$_2$Si(CH$_2$)$_3$]—SH,
[[Alk-O—(CH$_2$—CH(CH$_3$)O—)$_4$](MeO)$_2$Si(CH$_2$)$_3$]—SH,
[[Alk-O—(CH$_2$—CH(CH$_3$)O—)$_5$](MeO)$_2$Si(CH$_2$)$_3$]—SH,
[[Alk-O—(CH$_2$—CH(CH$_3$)O—)$_6$](MeO)$_2$Si(CH$_2$)$_3$]—SH,
[[Alk-O—(CH$_2$—CH(CH$_3$)O—)$_2$]$_2$ (MeO)Si(CH$_2$)$_3$]—SH,
[[Alk-O—(CH$_2$—CH(CH$_3$)O—)$_3$]$_2$(MeO)Si(CH$_2$)$_3$]—SH,
[[Alk-O—(CH$_2$—CH(CH$_3$)O—)$_4$]$_2$(MeO)Si(CH$_2$)$_3$]—SH,
[[Alk-O—(CH$_2$—CH(CH$_3$)O—)$_5$]$_2$(MeO)Si(CH$_2$)$_3$]—SH,
[[Alk-O—(CH$_2$—CH(CH$_3$)O—)$_6$]$_2$(MeO)Si(CH$_2$)$_3$]—SH,
[[Alk-O—(CH$_2$—CH(CH$_3$)O—)$_2$](Me)(MeO)Si(CH$_2$)$_3$]—SH, [[Alk-O—(CH$_2$—CH(CH$_3$)O—)$_3$](Me)(MeO)Si(CH$_2$)$_3$]—SH, [[Alk-O—(CH$_2$—CH(CH$_3$)O—)$_4$](Me)(MeO)Si(CH$_2$)$_3$]—SH, [[Alk-O—(CH$_2$—CH(CH$_3$)O—)$_5$](Me)(MeO)Si(CH$_2$)$_3$]—SH, [[Alk-O—(CH$_2$—CH(CH$_3$)O—)$_6$](Me)(MeO)Si(CH$_2$)$_3$]—SH,
[[Alk-O—(CH$_2$—CH(CH$_3$)O—)$_2$](EtO)$_2$Si(CH$_2$)$_3$]—SH,
[[Alk-O—(CH$_2$—CH(CH$_3$)O—)$_3$](EtO)$_2$Si(CH$_2$)$_3$]—SH,
[[Alk-O—(CH$_2$—CH(CH$_3$)O—)$_4$](EtO)$_2$Si(CH$_2$)$_3$]—SH,
[[Alk-O—(CH$_2$—CH(CH$_3$)O—)$_5$](EtO)$_2$Si(CH$_2$)$_3$]—SH,
[[Alk-O—(CH$_2$—CH(CH$_3$)O—)$_6$](EtO)$_2$Si(CH$_2$)$_3$]—SH,
[[Alk-O—(CH$_2$—CH(CH$_3$)O—)$_2$]$_2$(EtO)Si(CH$_2$)$_3$]—SH,
[[Alk-O—(CH$_2$—CH(CH$_3$)O—)$_3$]$_2$(EtO)Si(CH$_2$)$_3$]—SH,
[[Alk-O—(CH$_2$—CH(CH$_3$)O—)$_4$]$_2$(EtO)Si(CH$_2$)$_3$]—SH,
[[Alk-O—(CH$_2$—CH(CH$_3$)O—)$_5$]$_2$(EtO)Si(CH$_2$)$_3$]—SH,
[[Alk-O—(CH$_2$—CH(CH$_3$)O—)$_6$]$_2$(EtO)Si(CH$_2$)$_3$]—SH,
[[Alk-O—(CH$_2$—CH(CH$_3$)O—)$_2$](Me)(EtO)Si(CH$_2$)$_3$]—SH, [[Alk-O—(CH$_2$—CH(CH$_3$)O—)$_3$](Me)(EtO)Si(CH$_2$)$_3$]—SH, [[Alk-O—(CH$_2$—CH(CH$_3$)O—)$_4$](Me)(EtO)Si(CH$_2$)$_3$]—SH, [[Alk-O—(CH$_2$—CH(CH$_3$)O—)$_5$](Me)(EtO)Si(CH$_2$)$_3$]—SH, [[Alk-O—(CH$_2$—CH(CH$_3$)O—)$_6$](Me)(EtO)Si(CH$_2$)$_3$]—SH,
[[Alk-O—(CH$_2$—CH(CH$_3$)O—)$_2$]$_2$(Me)Si(CH$_2$)$_3$]—SH,
[[Alk-O—(CH$_2$—CH(CH$_3$)O—)$_3$]$_2$(Me)Si(CH$_2$)$_3$]—SH,
[[Alk-O—(CH$_2$—CH(CH$_3$)O—)$_4$]$_2$(Me)Si(CH$_2$)$_3$]—SH,
[[Alk-O—(CH$_2$—CH(CH$_3$)O—)$_5$]$_2$(Me)Si(CH$_2$)$_3$]—SH,
[[Alk-O—(CH$_2$—CH(CH$_3$)O—)$_6$]$_2$ (Me)Si(CH$_2$)$_3$]—SH,
[[Alk-O—(CH$_2$—CH(CH$_3$)O—)$_2$](Me)$_2$Si(CH$_2$)$_3$]—SH,
[[Alk-O—(CH$_2$—CH(CH$_3$)O—)$_3$](Me)$_2$Si(CH$_2$)$_3$]—SH,
[[Alk-O—(CH$_2$—CH(CH$_3$)O—)$_4$](Me)$_2$Si(CH$_2$)$_3$]—SH,
[[Alk-O—(CH$_2$—CH(CH$_3$)O—)$_5$](Me)$_2$Si(CH$_2$)$_3$]—SH, or
[[Alk-O—(CH$_2$—CH(CH$_3$)O—)$_6$](Me)$_2$Si(CH$_2$)$_3$]—SH,
where the Alk group can be unbranched or branched.

The mixtures of the invention can also comprise from 0.01 to 50% by weight, preferably from 0.05 to 40% by weight, particularly preferably from 0.1 to 25% by weight, very particularly preferably from 0.5 to 10% by weight, extremely preferably from 2 to 8% by weight, of polysulfidic organo (alkylpolyethersilanes) containing silanol groups, based on the total weight of the (mercaptoorganyl)alkylpolyethersilanes containing silanol groups and free from silanol groups.

The mixtures of the invention can also comprise from 0.1 to 50% by weight, or from 0.5 to 50% by weight, preferably from 1 to 50% by weight, particularly preferably from 1 to 35% by weight, very particularly preferably from 3 to 25% by weight, extremely preferably from 5 to 25% by weight, of polysulfidic organo(alkylpolyethersilanes) free from silanol groups, based on the total weight of the (mercaptoorganyl) alkylpolyethersilanes containing silanol groups and free from silanol groups.

The mixtures of the invention can also comprise from 0.1 to 50% by weight, preferably from 1 to 45% by weight, particularly preferably from 3 to 40% by weight, very particularly preferably from 5 to 30% by weight, extremely preferably from 8 to 25% by weight, of alkylpolyether alcohols, based on the total weight of the (mercaptoorganyl)alkylpolyethersilanes containing silanol groups and free from silanol groups.

Polysulfidic organo(alkylpolyethersilanes) containing silanol groups can be compounds of the general formula III

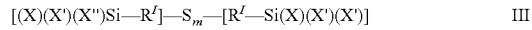

$$[(X)(X')(X'')Si—R^I]—S_m—[R^I—Si(X)(X')(X')] \quad \text{III}$$

where X, X', X'', and R$^I$ are independent of one another and are defined as above, and the average of m is from 1.5 to 8, preferably from 2 to 4, particularly from 2 to 3.5.

Polysulfidic organo(alkylpolyethersilanes) free from silanol groups can be compounds of the general formula IV

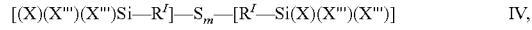

$$[(X)(X''')(X''')Si—R^I]—S_m—[R^I—Si(X)(X''')(X''')] \quad \text{IV,}$$

where X, X, X''', and R$^I$ are independent of one another and are defined as above.

Alkylpolyether alcohols can be compounds of the general formula V

$$HO—((CR^{II}_2)_w—O—)_v Alk \quad \text{V,}$$

where R$^{II}$, w, v, and Alk are defined as above.

Preferred compounds of the general formula III can be:
[[C$_3$H$_7$O—(CH$_2$—CH$_2$O)$_2$](Me)(HO)Si(CH$_2$)$_3$]—S$_m$—[(CH$_2$)$_3$Si (OMe)(Me)][(OCH$_2$—CH$_2$)$_3$—OC$_3$H$_7$]],
[[C$_3$H$_7$O—(CH$_2$—CH$_2$O)$_3$](Me)(HO)Si(CH$_2$)$_3$]—S$_m$—[(CH$_2$)$_3$Si(OMe)(Me)][(OCH$_2$—CH$_2$)$_3$—OC$_3$H$_7$]],
[[C$_3$H$_7$O—(CH$_2$—CH$_2$O)$_4$](Me)(HO)Si(CH$_2$)$_3$]—S$_m$—[(CH$_2$)$_3$Si(OMe)(Me)][(OCH$_2$—CH$_2$)$_3$—OC$_3$H$_7$]],
[[C$_3$H$_7$O—(CH$_2$—CH$_2$O)$_5$](Me)(HO)Si(CH$_2$)$_3$]—S$_m$—[(CH$_2$)$_3$Si(OMe)(Me)][(OCH$_2$—CH$_2$)$_3$—OC$_3$H$_7$]],
[[C$_3$H$_7$O—(CH$_2$—CH$_2$O)$_6$](Me)(HO)Si(CH$_2$)$_3$]—S$_m$—[(CH$_2$)$_3$Si(OMe)(Me)][(OCH$_2$—CH$_2$)$_3$OC$_3$H$_7$]],
[[C$_4$H$_9$O—(CH$_2$—CH$_2$O)$_2$](Me)(HO)Si(CH$_2$)$_3$]—S$_m$—[(CH$_2$)$_3$Si(OMe)(Me)][(OCH$_2$—CH$_2$)$_3$—OC$_4$H$_9$]],
[[C$_4$H$_9$O—(CH$_2$—CH$_2$O)$_3$](Me)(HO)Si(CH$_2$)$_3$]-S$_m$—[(CH$_2$)$_3$Si(OMe)(Me)][(OCH$_2$—CH$_2$)$_3$—OC$_4$H$_9$]],
[[C$_4$H$_9$O—(CH$_2$—CH$_2$O)$_4$](Me)(HO)Si(CH$_2$)$_3$]—S$_m$—[(CH$_2$)$_3$Si(OMe)(Me)][(OCH$_2$—CH$_2$)$_3$—C$_4$H$_9$]],
[[C$_4$H$_9$O—(CH$_2$—CH$_2$O)$_5$](Me)(HO)Si(CH$_2$)$_3$]—S$_m$—[(CH$_2$)$_3$Si(OMe)(Me)][(OCH$_2$—CH$_2$)$_3$—OC$_4$H$_9$]],
[[C$_4$H$_9$O—(CH$_2$—CH$_2$O)$_6$](Me)(HO)Si(CH$_2$)$_3$]-S$_m$—[(CH$_2$)$_3$Si(OMe)(Me)][(OCH$_2$—CH$_2$)$_3$—OC$_4$H$_9$]],
[[C$_5$H$_{11}$O—(CH$_2$—CH$_2$O)$_2$](Me)(HO)Si(CH$_2$)$_3$]—S$_m$—[(CH$_2$)$_3$Si(OMe)(Me)][(OCH$_2$—CH$_2$)$_3$—OC$_5$H$_{11}$]],
[[C$_5$H$_{11}$O—(CH$_2$—CH$_2$O)$_3$](Me)(HO)Si(CH$_2$)$_3$]-S$_m$—[(CH$_2$)$_3$Si(OMe)(Me)][(OCH$_2$—CH$_2$)$_3$—OC$_5$H$_{11}$]],
[[C$_5$H$_{11}$O—(CH$_2$—CH$_2$O)$_4$](Me)(HO)Si(CH$_2$)$_3$]—S$_m$—[(CH$_2$)$_3$Si(OMe)(Me)][(OCH$_2$—CH$_2$)$_3$—OC$_5$H$_{11}$]],
[[C$_5$H$_{11}$O—(CH$_2$—CH$_2$O)$_5$](Me)(HO)Si(CH$_2$)$_3$]-S$_m$—[(CH$_2$)$_3$Si(OMe)(Me)][(OCH$_2$—CH$_2$)$_3$—OC$_5$H$_{11}$]],
[[C$_5$H$_{11}$O—(CH$_2$—CH$_2$O)$_6$](Me)(HO)Si(CH$_2$)$_3$]-S$_m$—[(CH$_2$)$_3$Si(OMe)(Me)][(OCH$_2$—CH$_2$)$_3$—OC$_5$H$_{11}$]],
[[C$_6$H$_{13}$O—(CH$_2$—CH$_2$O)$_2$](Me)(HO)Si(CH$_2$)$_3$]-S$_m$—[(CH$_2$)$_3$Si(OMe)(Me)][(OCH$_2$—CH$_2$)$_3$OC$_6$H$_{13}$]],
[[C$_6$H$_{13}$O—(CH$_2$—CH$_2$O)$_3$](Me)(HO)Si(CH$_2$)$_3$]—S$_m$—[(CH$_2$)$_3$Si(OMe)(Me)][(OCH$_2$—CH$_2$)$_3$—OC$_6$H$_{13}$]],
[[C$_6$H$_{13}$O—(CH$_2$—CH$_2$O)$_4$](Me)(HO)Si(CH$_2$)$_3$]—S$_m$—

[(CH₂)₃Si(OMe)(Me)[(OCH₂—CH₂)₃—OC₆H₁₃]],
[[C₆H₁₃O—(CH₂—CH₂O)₅](Me)(HO)Si(CH₂)₃]-S_m—
[(CH₂)₃Si(OMe)(Me)[(OCH₂—CH₂)₃—OC₆H₁₃]],
[[C₆H₁₃O—(CH₂—CH₂O)₆](Me)(HO)Si(CH₂)₃]—S_m—
[(CH₂)₃Si(OMe)(Me)[(OCH₂—CH₂)₃—OC₆H₁₃]],
[[C₇H₁₅O—(CH₂—CH₂O)₂](Me)(HO)Si(CH₂)₃]-S_m—
[(CH₂)₃Si(OMe)(Me)[(OCH₂—CH₂)₃—OC₇H₁₅]],
[[C₇H₆O—(CH₂—CH₂O)₃](Me)(HO)Si(CH₂)₃]—S_m—
[(CH₂)₃Si(OMe)(Me)[(OCH₂—CH₂)₃OC₇H₁₅]],
[[C₇H₁₅O—(CH₂—CH₂O)₄](Me)(HO)Si(CH₂)₃]—S_m—
[(CH₂)₃Si(OMe)(Me)[(OCH₂—CH₂)₃OC₇H₁₅]],
[[C₇H₁₅O—(CH₂—CH₂O)₅](Me)(HO)Si(CH₂)₃]—S_m—
[(CH₂)₃Si(OMe)(Me)[(OCH₂—CH₂)₃—OC₇H₁₅]],
[[C₇H₁₅O—(CH₂—CH₂O)₆](Me)(HO)Si(CH₂)₃]—S_m—
[(CH₂)₃Si(OMe)(Me)[(OCH₂—CH₂)₃OC₇H₁₅]],
[[C₈H₁₇O—(CH₂—CH₂O)₂](Me)(HO)Si(CH₂)₃]—S_m—
[(CH₂)₃Si(OMe)(Me)[(OCH₂—CH₂)₃—OC₈H₁₇]],
[[C₈H₁₇O—(CH₂—CH₂O)₃](Me)(HO)Si(CH₂)₃]—S_m—
[(CH₂)₃Si(OMe)(Me)[(OCH₂—CH₂)₃—OC₈H₁₇]],
[[C₈H₁₇O—(CH₂—CH₂O)₄](Me)(HO)Si(CH₂)₃]-S_m—
[(CH₂)₃Si(OMe)(Me)[(OCH₂—CH₂)₃—OC₈H₁₇]],
[[C₈H₁₇O—(CH₂—CH₂O)₅](Me)(HO)Si(CH₂)₃]—S_m—
[(CH₂)₃Si(OMe)(Me)[(OCH₂—CH₂)₃—OC₈H₁₇]],
[[C₈H₁₇O—(CH₂—CH₂O)₆](Me)(HO)Si(CH₂)₃]—S_m—
[(CH₂)₃Si(OMe)(Me)[(OCH₂—CH₂)₃—OC₈H₁₇]],
[[C₉H₁₉O—(CH₂—CH₂O)₂](Me)(HO)Si(CH₂)₃]-S_m—
[(CH₂)₃Si(OMe)(Me)[(OCH₂—CH₂)₃—OC₉H₁₉]],
[[C₉H₁₉O—(CH₂—CH₂O)₃](Me)(HO)Si(CH₂)₃]—S_m—
[(CH₂)₃Si(OMe)(Me)[(OCH₂—CH₂)₃—OC₉H₁₉]],
[[C₉H₁₉O—(CH₂—CH₂O)₄](Me)(HO)Si(CH₂)₃]-S_m—
[(CH₂)₃Si(OMe)(Me)[(OCH₂—CH₂)₃—OC₉H₁₉]],
[[C₉H₁₉O—(CH₂—CH₂O)₅](Me)(HO)Si(CH₂)₃]—S_m—
[(CH₂)₃Si(OMe)(Me)[(OCH₂—CH₂)₃—OC₉H₁₉]],
[[C₉H₁₉O—(CH₂—CH₂O)₆](Me)(HO)Si(CH₂)₃]—S_m—
[(CH₂)₃Si(OMe)(Me)[(OCH₂—CH₂)₃—OC₉H₁₉]],
[[C₁₀H₂₁O—(CH₂—CH₂O)₂](Me)(HO)Si(CH₂)₃]-S_m—
[(CH₂)₃Si(OMe)(Me)[(OCH₂—CH₂)₃—OC₁₀H₂₁]],
[[C₁₀H₂₁O—(CH₂—CH₂O)₃](Me)(HO)Si(CH₂)₃]—S_m—
[(CH₂)₃Si(OMe)(Me)[(OCH₂—CH₂)₃—OC₁₀H₂₁]],
[[C₁₀H₂₁O—(CH₂—CH₂O)₄](Me)(HO)Si(CH₂)₃]—S_m—
[(CH₂)₃Si(OMe)(Me)[(OCH₂—CH₂)₃—OC₁₀H₂₁]],
[[C₁₀H₂₁O—(CH₂—CH₂O)₅](Me)(HO)Si(CH₂)₃]—S_m—
[(CH₂)₃Si(OMe)(Me)[(OCH₂—CH₂)₃—OC₁₀H₂₁]],
[[C₁₀H₂₁O—(CH₂—CH₂O)₆](Me)(HO)Si(CH₂)₃]—S_m—
[(CH₂)₃Si(OMe)(Me)[(OCH₂—CH₂)₃—OC₁₀H₂₁]],
[[C₁₁H₂₃O—(CH₂—CH₂O)₂](Me)(HO)Si(CH₂)₃]-S_m—
[(CH₂)₃Si(OMe)(Me)[(OCH₂—CH₂)₃—OC₁₁H₂₃]],
[[C₁₁H₂₃O—(CH₂—CH₂O)₃](Me)(HO)Si(CH₂)₃]—S_m—
[(CH₂)₃Si(OMe)(Me)[(OCH₂—CH₂)₃—OC₁₁H₂₃]],
[[C₁₁H₂₃O—(CH₂—CH₂O)₄](Me)(HO)Si(CH₂)₃]-S_m—
[(CH₂)₃Si(OMe)(Me)[(OCH₂—CH₂)₃—OC₁₁H₂₃]],
[[C₁₁H₂₃O—(CH₂—CH₂O)₅](Me)(HO)Si(CH₂)₃]—S_m—
[(CH₂)₃Si(OMe)(Me)[(OCH₂—CH₂)₃—OC₁₁H₂₃]],
[[C₁₁H₂₃O—(CH₂—CH₂O)₆](Me)(HO)Si(CH₂)₃]—S_m—
[(CH₂)₃Si(OMe)(Me)[(OCH₂—CH₂)₃—OC₁₁H₂₃]],
[[C₁₂H₂₅O—(CH₂—CH₂O)₂](Me)(HO)Si(CH₂)₃]—S_m—
[(CH₂)₃Si(OMe)(Me)[(OCH₂—CH₂)₃—OC₁₂H₂₅]],
[[C₁₂H₂₅O—(CH₂—CH₂O)₃](Me)(HO)Si(CH₂)₃]—S_m—
[(CH₂)₃Si(OMe)(Me)[(OCH₂—CH₂)₃—OC₁₂H₂₅]],
[[C₁₂H₂₅O—(CH₂—CH₂O)₄](Me)(HO)Si(CH₂)₃]—S_m—
[(CH₂)₃Si(OMe)(Me)[(OCH₂—CH₂)₃—OC₁₂H₂₅]],
[[C₁₂H₂₅O—(CH₂—CH₂O)₅](Me)(HO)Si(CH₂)₃]—S_m—
[(CH₂)₃Si(OMe)(Me)[(OCH₂—CH₂)₃—OC₁₂H₂₅]],
[[C₁₂H₂₅O—(CH₂—CH₂O)₆](Me)(HO)Si(CH₂)₃]-S_m—
[(CH₂)₃Si(OMe)(Me)[(OCH₂—CH₂)₃—OC₁₂H₂₅]],
[[C₁₃H₂₇O—(CH₂—CH₂O)₂](Me)(HO)Si(CH₂)₃]-S_m—
[(CH₂)₃Si(OMe)(Me)[(OCH₂—CH₂)₃—OC₁₃H₂₇]],
[[C₁₃H₂₇O—(CH₂—CH₂O)₃](Me)(HO)Si(CH₂)₃]—S_m—
[(CH₂)₃Si(OMe)(Me)[(OCH₂—CH₂)₃—OC₁₃H₂₇]],
[[C₁₃H₂₇O—(CH₂—CH₂O)₄](Me)(HO)Si(CH₂)₃]—S_m—
[(CH₂)₃Si(OMe)(Me)[(OCH₂—CH₂)₃—OC₁₃H₂₇]],
[[C₁₃H₂₇O—(CH₂—CH₂O)₅](Me)(HO)Si(CH₂)₃]—S_m—
[(CH₂)₃Si(OMe)(Me)[(OCH₂—CH₂)₃—OC₁₃H₂₇]],
[[C₁₃H₂₇O—(CH₂—CH₂O)₆](Me)(HO)Si(CH₂)₃]-S_m—
[(CH₂)₃Si(OMe)(Me)[(OCH₂—CH₂)₃—OC₁₃H₂₇]],
[[C₁₄H₂₉O—(CH₂—CH₂O)₂](Me)(HO)Si(CH₂)₃]—S_m—
[(CH₂)₃Si(OMe)(Me)[(OCH₂—CH₂)₃—OC₁₄H₂₉]],
[[C₁₄H₂₉O—(CH₂—CH₂O)₃](Me)(HO)Si(CH₂)₃]—S_m—
[(CH₂)₃Si(OMe)(Me)[(OCH₂—CH₂)₃OC₁₄H₂₉]],
[[C₁₄H₂₉O—(CH₂—CH₂O)₄](Me)(HO)Si(CH₂)₃]—S_m—
[(CH₂)₃Si(OMe)(Me)[(OCH₂—CH₂)₃OC₁₄H₂₉]],
[[C₁₄H₂₉O—(CH₂—CH₂O)₅](Me)(HO)Si(CH₂)₃]—S_m—
[(CH₂)₃Si(OMe)(Me)[(OCH₂—CH₂)₃—C₁₄H₂₉]],
[[C₁₄H₂₉O—(CH₂—CH₂O)₆](Me)(HO)Si(CH₂)₃]—S_m—
[(CH₂)₃Si(OMe)(Me)[(OCH₂—CH₂)₃—OC₁₄H₂₉]],
[[C₁₅H₃₁O—(CH₂—CH₂O)₂](Me)(HO)Si(CH₂)₃]—S_m—
[(CH₂)₃Si(OMe)(Me)[(OCH₂—CH₂)₃—OC₁₅H₃₁]],
[[C₁₅H₃₁O—(CH₂—CH₂O)₃](Me)(HO)Si(CH₂)₃]—S_m—
[(CH₂)₃Si(OMe)(Me)[(OCH₂—CH₂)₃—OC₁₅H₃₁]],
[[C₁₅H₃₁O—(CH₂—CH₂O)₄](Me)(HO)Si(CH₂)₃]—S_m—
[(CH₂)₃Si(OMe)(Me)[(OCH₂—CH₂)₃—OC₁₅H₃₁]],
[[C₁₅H₃₁O—(CH₂—CH₂O)₅](Me)(HO)Si(CH₂)₃]—S_m—
[(CH₂)₃Si(OMe)(Me)[(OCH₂—CH₂)₃—OC₁₅H₃₁]],
[[C₁₅H₃₁O—(CH₂—CH₂O)₆](Me)(HO)Si(CH₂)₃]-S_m—
[(CH₂)₃Si(OMe)(Me)[(OCH₂—CH₂)₃—OC₁₅H₃₁]],
[[C₁₆H₃₃O—(CH₂—CH₂O)₂](Me)(HO)Si(CH₂)₃]-S_m—
[(CH₂)₃Si(OMe)(Me)[(OCH₂—CH₂)₃—OC₁₆H₃₃]],
[[C₁₆H₃₃O—(CH₂—CH₂O)₃](Me)(HO)Si(CH₂)₃]—S_m—
[(CH₂)₃Si(OMe)(Me)[(OCH₂—CH₂)₃—OC₁₆H₃₃]],
[[C₁₆H₃₃O—(CH₂—CH₂O)₄](Me)(HO)Si(CH₂)₃]—S_m—
[(CH₂)₃Si(OMe)(Me)[(OCH₂—CH₂)₃—OC₁₆H₃₃]],
[[C₁₆H₃₃O—(CH₂—CH₂O)₅](Me)(HO)Si(CH₂)₃]-S_m—
[(CH₂)₃Si(OMe)(Me)[(OCH₂—CH₂)₃—OC₁₆H₃₃]],
[[C₁₆H₃₃O—(CH₂—CH₂O)₆](Me)(HO)Si(CH₂)₃]—S_m—
[(CH₂)₃Si(OMe)(Me)[(OCH₂—CH₂)₃—OC₁₆H₃₃]],
[[C₁₇H₃₅O—(CH₂—CH₂O)₂](Me)(HO)Si(CH₂)₃]—S_m—
[(CH₂)₃Si(OMe)(Me)[(OCH₂—CH₂)₃—OC₁₇H₃₅]],
[[C₁₇H₃₅O—(CH₂—CH₂O)₃](Me)(HO)Si(CH₂)₃]—S_m—
[(CH₂)₃Si(OMe)(Me)[(OCH₂—CH₂)₃—OC₁₇H₃₅]],
[[C₁₇H₃₅O—(CH₂—CH₂O)₄](Me)(HO)Si(CH₂)₃]—S_m—
[(CH₂)₃Si(OMe)(Me)[(OCH₂—CH₂)₃—OC₁₇H₃₅]],
[[C₁₇H₃₅O—(CH₂—CH₂O)₅](Me)(HO)Si(CH₂)₃]—S_m—
[(CH₂)₃Si(OMe)(Me)[(OCH₂—CH₂)₃—OC₁₇H₃₅]],
[[C₁₇H₃₅O—(CH₂—CH₂O)₆](Me)(HO)Si(CH₂)₃]—S_m—
[(CH₂)₃Si(OMe)(Me)[(OCH₂—CH₂)₃—OC₁₇H₃₅]],
[[C₁₈H₃₇O—(CH₂—CH₂O)₂](Me)(HO)Si(CH₂)₃]-S_m—
[(CH₂)₃Si(OMe)(Me)[(OCH₂—CH₂)₃—OC₁₈H₃₇]],
[[C₁₈H₃₇O—(CH₂—CH₂O)₃](Me)(HO)Si(CH₂)₃]-S_m—
[(CH₂)₃Si(OMe)(Me)[(OCH₂—CH₂)₃—OC₁₈H₃₇]],
[[C₁₈H₃₇O(CH₂—CH₂O)₄](Me)(HO)Si(CH₂)₃]-S_m—
[(CH₂)₃Si(OMe)(Me)[(OCH₂—CH₂)₃—OC₁₈H₃₇]],
[[C₁₈H₃₇O—(CH₂—CH₂O)₅](Me)(HO)Si(CH₂)₃]-S_m—
[(CH₂)₃Si(OMe)(Me)[(OCH₂—CH₂)₃—OC₁₈H₃₇]],
[[C₃H₇O—(CH₂—CH₂O)₂](MeO)(HO)Si(CH₂)₃]-S_m—
[(CH₂)₃Si(OMe)₂[(OCH₂—CH₂)₃—OC₃H₇]], [[C₃H₇O—(CH₂—CH₂O)₃](MeO)(HO)Si(CH₂)₃]—S_m— [(CH₂)₃Si(OMe)₂[(OCH₂—CH₂)₃—OC₃H₇]], [[C₃H₇O—(CH₂—CH₂O)₄](MeO)(HO)Si(CH₂)₃]—S_m— [(CH₂)₃Si(OMe)₂[(OCH₂—CH₂)₃—OC₃H₇]], [[C₃H₇O—(CH₂—CH₂O)₅](MeO)(HO)Si(CH₂)₃]—S_m— [(CH₂)₃Si(OMe)₂[(OCH₂—CH₂)₃—OC₃H₇]], [[C₃H₇O—(CH₂—CH₂O)₆](MeO)(HO)Si(CH₂)₃]—S_m— [(CH₂)₃Si(OMe)₂[(OCH₂—CH₂)₃—OC₃H₇]], [[C₄H₉O—(CH₂—CH₂O)₂](MeO)(HO)Si(CH₂)₃]—S_m— [(CH₂)₃Si(OMe)₂[(OCH₂—CH₂)₃—

$OC_4H_9]]$, $[[C_4H_9O—(CH_2—CH_2O)_3(MeO)(HO)Si(CH_2)_3]-S_m— [(CH_2)_3Si (OMe)_2[(OCH_2—CH_2)_3—OC_4H_9]]$, $[[C_4H_9O—(CH_2—CH_2O)_4(MeO)(HO)Si(CH_2)_3]—S_m— [(CH_2)_3Si (OMe)_2[(OCH_2—CH_2)_3—OC_4H_9]]$, $[[C_4H_9O—(CH_2—CH_2O)_5(MeO)(HO)Si(CH_2)_3]-S_m— [(CH_2)_3Si (OMe)_2[(OCH_2—CH_2)_3—OC_4H_9]]$, $[[C_4H_9O—(CH_2—CH_2O)_6(MeO)(HO)Si(CH_2)_3]-S_m— [(CH_2)_3Si (OMe)_2[(OCH_2—CH_2)_3—OC_4H_9]]$, $[[C_5H_{11}O—(CH_2—CH_2O)_2(MeO)(HO)Si(CH_2)_3]—S_m—[(CH_2)_3Si(OMe)_2[(OCH_2—CH_2)_3—OC_5H_{11}]]$, $[[C_5H_{11}O—(CH_2—CH_2O)_3(MeO)(HO)Si(CH_2)_3]-S_m—[(CH_2)_3Si (OMe)_2[(OCH_2—CH_2)_3—OC_5H_{11}]]$, $[[C_5H_{11}O—(CH_2—CH_2O)_4(MeO)(HO)Si(CH_2)_3]—S_m—[(CH_2)_3Si(OMe)_2[(OCH_2—CH_2)_3—OC_5H_{11}]]$, $[[C_5H_{11}O—(CH_2—CH_2O)_5(MeO)(HO)Si(CH_2)_3]—S_m—[(CH_2)_3Si (OMe)_2[(OCH_2—CH_2)_3—OC_5H_{11}]]$, $[[C_5H_{11}O—(CH_2—CH_2O)_6(MeO)(HO)Si(CH_2)_3]—S_m—[(CH_2)_3Si(OMe)_2[(OCH_2—CH_2)_3—OC_5H_{11}]]$, $[[C_6H_{13}O—(CH_2—CH_2O)_2(MeO)(HO)Si(CH_2)_3]—S_m—[(CH_2)_3Si (OMe)_2[(OCH_2—CH_2)_3—OC_6H_{13}]]$, $[[C_6H_{13}O—(CH_2—CH_2O)_3(MeO)(HO)Si(CH_2)_3]—S_m—[(CH_2)_3Si(OMe)_2[(OCH_2—CH_2)_3—OC_6H_{13}]]$, $[[C_6H_{13}O—(CH_2—CH_2O)_4(MeO)(HO)Si(CH_2)_3]—S_m—[(CH_2)_3Si (OMe)_2[(OCH_2—CH_2)_3—OC_6H_{13}]]$, $[[C_6H_{13}O—(CH_2—CH_2O)_5(MeO)(HO)Si(CH_2)_3]—S_m—[(CH_2)_3Si(OMe)_2[(OCH_2—CH_2)_3—OC_6H_{13}]]$, $[[C_6H_{13}O—(CH_2—CH_2O)_6(MeO)(HO)Si(CH_2)_3]—S_m—[(CH_2)_3Si (OMe)_2[(OCH_2—CH_2)_3—OC_6H_{13}]]$, $[[C_7H_{15}O—(CH_2—CH_2O)_2(MeO)(HO)Si(CH_2)_3]—S_m—[(CH_2)_3Si (OMe)_2[(OCH_2—CH_2)_3—OC_7H_{15}]]$, $[[C_7H_{15}O—(CH_2—CH_2O)_3(MeO)(HO)Si(CH_2)_3]-S_m—[(CH_2)_3Si(OMe)_2[(OCH_2—CH_2)_3—OC_7H_{15}]]$, $[[C_7H_{15}O—(CH_2—CH_2O)_4(MeO)(HO)Si(CH_2)_3]—S_m—[(CH_2)_3Si(OMe)_2[(OCH_2—CH_2)_3—OC_7H_{15}]]$, $[[C_7H_{15}O—(CH_2—CH_2O)_5(MeO)(HO)Si(CH_2)_3]—S_m—[(CH_2)_3Si(OMe)_2[(OCH_2—CH_2)_3—OC_7H_{15}]]$, $[[C_7H_{15}O(CH_2—CH_2O)_6(MeO)(HO)Si(CH_2)_3]—S_m— [(CH_2)_3Si(OMe)_2[(OCH_2—CH_2)_3—OC_7H_{15}]]$, $[[C_8H_{17}O—(CH_2—CH_2O)_2](MeO)(HO)Si(CH_2)_3]—S_m— [(CH_2)_3Si(OMe)_2[(OCH_2—CH_2)_3—OC_8H_{17}]]$, $[[C_8H_{17}O—(CH_2—CH_2O)_3](MeO)(HO)Si(CH_2)_3]—S_m— [(CH_2)_3Si(OMe)_2[(OCH_2—CH_2)_3—OC_8H_{17}]]$, $[[C_8H_{17}O—(CH_2—CH_2O)_4(MeO)(HO)Si(CH_2)_3]—S_m— [(CH_2)_3Si(OMe)_2[(OCH_2—CH_2)_3—OC_8H_{17}]]$, $[[C_8H_{17}O—(CH_2—CH_2O)_5(MeO)(HO)Si(CH_2)_3]—S_m— [(CH_2)_3Si(OMe)_2[(OCH_2—CH_2)_3—OC_8H_{17}]]$, $[[C_8H_{17}O—(CH_2—CH_2O)_6(MeO)(HO)Si(CH_2)_3]—S_m— [(CH_2)_3Si(OMe)_2[(OCH_2—CH_2)_3—OC_8H_{17}]]$, $[[C_9H_{19}O—(CH_2—CH_2O)_2(MeO)(HO)Si(CH_2)_3]-S_m— [(CH_2)_3Si(OMe)_2[(OCH_2—CH_2)_3—OC_9H_{19}]]$, $[[C_9H_{19}O—(CH_2—CH_2O)_3(MeO)(HO)Si(CH_2)_3]—S_m— [(CH_2)_3Si(OMe)_2[(OCH_2—CH_2)_3—OC_9H_{19}]]$, $[[C_9H_{19}O—(CH_2—CH_2O)_4(MeO)(HO)Si(CH_2)_3]-S_m— [(CH_2)_3Si(OMe)_2[(OCH_2—CH_2)_3—OC_9H_{19}]]$, $[[C_9H_{19}O—(CH_2—CH_2O)_5(MeO)(HO)Si(CH_2)_3]—S_m— [(CH_2)_3Si(OMe)_2[(OCH_2—CH_2)_3—OC_9H_{19}]]$, $[[C_9H_{19}O—(CH_2—CH_2O)_6(MeO)(HO)Si(CH_2)_3]—S_m— [(CH_2)_3Si(OMe)_2[(OCH_2—CH_2)_3—OC_9H_{19}]]$, $[[C_{10}H_{21}O—(CH_2—CH_2O)_2](MeO)(HO)Si(CH_2)_3]-S_m—[(CH_2)_3Si(OMe)_2[(OCH_2—CH_2)_3—OC_{10}H_{21}]]$, $[[C_{10}H_{21}O—(CH_2—CH_2O)_3](MeO)(HO)Si(CH_2)_3]-S_m—[(CH_2)_3Si(OMe)_2[(OCH_2—CH_2)_3—OC_{10}H_{21}]]$, $[[C_{10}H_{21}O—(CH_2—CH_2O)_4(MeO)(Ho)Si(CH_2)_3]—S_m—[(CH_2)_3Si(OMe)_2[(OCH_2—CH_2)_3—OC_{10}H_{21}]]$, $[[C_{10}H_{21}O—(CH_2—CH_2O)_5(MeO)(HO)Si(CH_2)_3]-S_m—[(CH_2)_3Si(OMe)_2[(OCH_2—CH_2)_3—OC_{10}H_{21}]]$, $[[C_{10}H_{21}O—(CH_2—CH_2O)_6(MeO)(HO)Si(CH_2)_3]-S_m—[(CH_2)_3Si(OMe)_2[(OCH_2—CH_2)_3—OC_{10}H_{21}]]$, $[[C_{11}H_{23}O—(CH_2—CH_2O)_2(MeO)(HO)Si(CH_2)_3]—S_m—[(CH_2)_3Si (OMe)_2[(OCH_2—CH_2)_3—OC_{11}H_{23}]]$, $[[C_{11}H_{23}O—(CH_2—CH_2O)_3(MeO)(HO)Si(CH_2)_3]—S_m—[(CH_2)_3Si (OMe)_2[(OCH_2—CH_2)_3—OC_{11}H_{23}]]$, $[[C_{11}H_{23}O—(CH_2—CH_2O)_4(MeO)(HO)Si(CH_2)_3]-S_m—[(CH_2)_3Si(OMe)_2[(OCH_2—CH_2)_3—OC_{11}H_{23}]]$, $[[C_{11}H_{23}O—(CH_2—CH_2O)_5(MeO)(HO)Si(CH_2)_3]—S_m—[(CH_2)_3Si(OMe)_2[(OCH_2—CH_2)_3—OC_{11}H_{23}]]$, $[[C_{11}H_{23}O—(CH_2—CH_2O)_6(MeO)(HO)Si(CH_2)_3]-S_m—[(CH_2)_3Si(OMe)_2[(OCH_2—CH_2)_3—OC_{11}H_{23}]]$, $[[C_{12}H_{25}O—(CH_2—CH_2O)_2(MeO)(HO)Si(CH_2)_3]—S_m—[(CH_2)_3Si(OMe)_2[(OCH_2—CH_2)_3—OC_{12}H_{25}]]$, $[[C_{12}H_{25}O—(CH_2—CH_2O)_3(MeO)(HO)Si(CH_2)_3]—S_m—[(CH_2)_3Si(OMe)_2[(OCH_2—CH_2)_3—OC_{12}H_{25}]]$, $[[C_{12}H_{25}O—(CH_2—CH_2O)_4(MeO)(HO)Si(CH_2)_3]-S_m—[(CH_2)_3Si(OMe)_2[(OCH_2—CH_2)_3—OC_{12}H_{25}]]$, $[[C_{12}H_{25}O—(CH_2—CH_2O)_5(MeO)(HO)Si(CH_2)_3]—S_m—[(CH_2)_3Si(OMe)_2[(OCH_2—CH_2)_3—OC_{12}H_{25}]]$, $[[C_{12}H_{25}O—(CH_2—CH_2O)_6(MeO)(HO)Si(CH_2)_3]—S_m—[(CH_2)_3Si(OMe)_2[(OCH_2—CH_2)_3—OC_{12}H_{25}]]$, $[[C_{13}H_{27}O—(CH_2—CH_2O)_2(MeO)(HO)Si(CH_2)_3]—S_m—[(CH_2)_3Si(OMe)_2[(OCH_2—CH_2)_3—OC_{13}H_{27}]]$, $[[C_{13}H_{27}O—(CH_2—CH_2O)_3(MeO)(HO)Si(CH_2)_3]—S_m—[(CH_2)_3Si(OMe)_2[(OCH_2—CH_2)_3—OC_{13}H_{27}]]$, $[[C_{13}H_{27}O—(CH_2—CH_2O)_4(MeO)(HO)Si(CH_2)_3]—S_m—[(CH_2)_3Si(OMe)_2[(OCH_2—CH_2)_3—OC_{13}H_{27}]]$, $[[C_{13}H_{27}O—(CH_2—CH_2O)_5(MeO)(HO)Si(CH_2)_3]—S_m—[(CH_2)_3Si(OMe)_2[(OCH_2—CH_2)_3—OC_{13}H_{27}]]$, $[[C_{13}H_{27}O—(CH_2—CH_2O)_6(MeO)(HO)Si(CH_2)_3]—S_m—[(CH_2)_3Si(OMe)_2[(OCH_2—CH_2)_3—OC_{13}H_{27}]]$, $[[C_{14}H_{29}O—(CH_2—CH_2O)_2(MeO)(HO)Si(CH_2)_3]—S_m—[(CH_2)_3Si(OMe)_2[(OCH_2—CH_2)_3—OC_{14}H_{29}]]$, $[[C_{14}H_{29}O—(CH_2—CH_2O)_3(MeO)(HO)Si(CH_2)_3]—S_m—[(CH_2)_3Si(OMe)_2[(OCH_2—CH_2)_3—OC_{14}H_{29}]]$, $[[C_{14}H_{29}O—(CH_2—CH_2O)_4(MeO)(HO)Si(CH_2)_3]—S_m—[(CH_2)_3Si(OMe)_2[(OCH_2—CH_2)_3—OC_{14}H_{29}]]$, $[[C_{14}H_{29}O—(CH_2—CH_2O)_5(MeO)(HO)Si(CH_2)_3]—S_m—[(CH_2)_3Si(OMe)_2[(OCH_2—CH_2)_3—OC_{14}H_{29}]]$, $[[C_{14}H_{29}O—(CH_2—CH_2O)_6(MeO)(HO)Si(CH_2)_3]—S_m—[(CH_2)_3Si(OMe)_2[(OCH_2—CH_2)_3—OC_{14}H_{29}]]$, $[[C_{15}H_{31}O—(CH_2—CH_2O)_2(MeO)(HO)Si(CH_2)_3]—S_m—[(CH_2)_3Si(OMe)_2[(OCH_2—CH_2)_2—OC_{15}H_{31}]]$, $[[C_{15}H_{31}O—(CH_2—CH_2O)_3(MeO)(HO)Si(CH_2)_3]—S_m—[(CH_2)_3Si(OMe)_2[(OCH_2—CH_2)_3—OC_{15}H_{31}]]$, $[[C_{15}H_{31}O—(CH_2—CH_2O)_4(MeO)(HO)Si(CH_2)_3]—S_m—[(CH_2)_3Si(OMe)_2[(OCH_2—CH_2)_4—OC_{15}H_{31}]]$, $[[C_{15}H_{31}O—(CH_2—CH_2O)_5(MeO)(HO)Si(CH_2)_3]-S_m—[(CH_2)_3Si(OMe)_2[(OCH_2—CH_2)_5—OC_{15}H_{31}]]$, $[[C_{15}H_{31}O—(CH_2—CH_2O)_6(MeO)(HO)Si(CH_2)_3]—S_m—[(CH_2)_3Si(OMe)_2[(OCH_2—CH_2)_6—OC_{15}H_{31}]]$, $[[C_{16}H_{33}O—(CH_2—CH_2O)_2(MeO)(HO)Si(CH_2)_3]-S_m—[(CH_2)_3Si(OMe)_2[(OCH_2—CH_2)_2—OC_{16}H_{33}]]$, $[[C_{16}H_{33}O—(CH_2—CH_2O)_3(MeO)(HO)Si(CH_2)_3]—S_m—[(CH_2)_3Si(OMe)_2[(OCH_2—CH_2)_3—OC_{16}H_{33}]]$, $[[C_{16}H_{33}O—(CH_2—CH_2O)_4(MeO)(HO)Si(CH_2)_3]—S_m—[(CH_2)_3Si(OMe)_2[(OCH_2—CH_2)_4—OC_{16}H_{33}]]$, $[[C_{16}H_{33}O—(CH_2—CH_2O)_5(MeO)(HO)Si(CH_2)_3]-S_m—[(CH_2)_3Si(OMe)_2[(OCH_2—CH_2)_5—OC_{16}H_{33}]]$, $[[C_{16}H_{33}O—(CH_2—CH_2O)_6(MeO)(HO)Si(CH_2)_3]—S_m—[(CH_2)_3Si(OMe)_2[(OCH_2—CH_2)_6—OC_{16}H_{33}]]$, $[[C_{17}H_{35}O—(CH_2—CH_2O)_2(MeO)(HO)Si(CH_2)_3]—S_m—[(CH_2)_3Si(OMe)_2[(OCH_2—CH_2)_2—OC_{17}H_{35}]]$, $[[C_{17}H_{35}O—(CH_2—CH_2O)_3(MeO)(HO)Si(CH_2)_3]—S_m—[(CH_2)_3Si(OMe)_2[(OCH_2—CH_2)_3—OC_{17}H_{35}]]$, $[[C_{17}H_{35}O—(CH_2—CH_2O)_4(MeO)(HO)Si(CH_2)_3]—S_m—$

[(CH$_2$)$_3$Si(OMe)$_2$[(OCH$_2$—CH$_2$)$_4$—OC$_{17}$H$_{35}$]],
[[C$_{17}$H$_{35}$O—(CH$_2$—CH$_2$O)$_5$](MeO)(HO)Si(CH$_2$)$_3$]-S$_m$— [(CH$_2$)$_3$Si(OMe)$_2$[(OCH$_2$—CH$_2$)$_5$—OC$_{17}$H$_{35}$]],
[[C$_{17}$H$_{35}$O—(CH$_2$—CH$_2$O)$_6$](MeO)(HO)Si(CH$_2$)$_3$]—S$_m$— [(CH$_2$)$_3$Si(OMe)$_2$[(OCH$_2$—CH$_2$)$_6$—OC$_{17}$H$_{35}$]],
[[C$_{18}$H$_{37}$O—(CH$_2$—CH$_2$O)$_2$](MeO)(HO)Si(CH$_2$)$_3$]—S$_m$— [(CH$_2$)$_3$Si(OMe)$_2$[(OCH$_2$—CH$_2$)$_2$—OC$_{18}$H$_{37}$]],
[[C$_{18}$H$_{37}$O—(CH$_2$—CH$_2$O)$_3$](MeO)(HO)Si(CH$_2$)$_3$]—S$_m$— [(CH$_2$)$_3$Si(OMe)$_2$[(OCH$_2$—CH$_2$)$_3$—OC$_{18}$H$_{37}$]],
[[C$_{18}$H$_{37}$O—(CH$_2$—CH$_2$O)$_4$](MeO)(HO)Si(CH$_2$)$_3$]—S$_m$— [(CH$_2$)$_3$Si(OMe)$_2$[(OCH$_2$—CH$_2$)$_4$—OC$_{18}$H$_{37}$]],
[[C$_{18}$H$_{37}$O—(CH$_2$—CH$_2$O)$_5$](MeO)(HO)Si(CH$_2$)$_3$]—S$_m$— [(CH$_2$)$_3$Si(OMe)$_2$[(OCH$_2$—CH$_2$)$_5$—OC$_{18}$H$_{37}$]],
[[C$_{18}$H$_{37}$O—(CH$_2$—CH$_2$O)$_6$](MeO)(HO)Si(CH$_2$)$_3$]—S$_m$— [(CH$_2$)$_3$Si(OMe)$_2$[(OCH$_2$—CH$_2$)$_6$—OC$_{18}$H$_{37}$]],
[[C$_3$H$_7$O—(CH$_2$—CH$_2$O)$_2$](EtO)(HO)Si(CH$_2$)$_3$]-S$_m$— [(CH$_2$)$_3$Si(OEt)$_2$[(OCH$_2$—CH$_2$)$_2$—OC$_3$H$_7$]], [[C$_3$H$_7$O—(CH$_2$—CH$_2$O)$_3$](EtO)(HO)Si(CH$_2$)$_3$]—S$_m$— [(CH$_2$)$_3$Si(OEt)$_2$[(OCH$_2$—CH$_2$)$_3$—OC$_3$H$_7$]], [[C$_3$H$_7$O—(CH$_2$—CH$_2$O)$_4$](EtO)(HO)Si(CH$_2$)$_3$]—S$_m$— [(CH$_2$)$_3$Si(OEt)$_2$[(OCH$_2$—CH$_2$)$_4$—OC$_3$H$_7$]], [[C$_3$H$_7$O—(CH$_2$—CH$_2$O)$_6$](EtO)(HO)Si(CH$_2$)$_3$]—S$_m$— [(CH$_2$)$_3$Si(OEt)$_2$[(OCH$_2$—CH$_2$)$_5$—OC$_3$H$_7$]], [[C$_3$H$_7$O—(CH$_2$—CH$_2$O)$_6$](EtO)(HO)Si(CH$_2$)$_3$]—S$_m$— [(CH$_2$)$_3$Si(OEt)$_2$[(OCH$_2$—CH$_2$)$_6$—OC$_3$H$_7$]],
[[C$_4$H$_9$O—(CH$_2$—CH$_2$O)$_2$](EtO)(HO)Si(CH$_2$)$_3$]-S$_m$— [(CH$_2$)$_3$Si(OEt)$_2$[(OCH$_2$—CH$_2$)$_2$—OC$_4$H$_9$]], [[C$_4$H$_9$O—(CH$_2$—CH$_2$O)$_3$](EtO)(HO)Si(CH$_2$)$_3$]—S$_m$— [(CH$_2$)$_3$Si(OEt)$_2$[(OCH$_2$—CH$_2$)$_3$—OC$_4$H$_9$]], [[C$_4$H$_9$O—(CH$_2$—CH$_2$O)$_4$](EtO)(HO)Si(CH$_2$)$_3$]-S$_m$— [(CH$_2$)$_3$Si(OEt)$_2$[(OCH$_2$—CH$_2$)$_4$OC$_4$H$_9$]], [[C$_4$H$_9$O—(CH$_2$—CH$_2$O)$_5$](EtO)(HO)Si(CH$_2$)$_3$]—S$_m$— [(CH$_2$)$_3$Si(OEt)$_2$[(OCH$_2$—CH$_2$)$_5$—OC$_4$H$_9$]], [[C$_4$H$_9$O—(CH$_2$—CH$_2$O)$_6$](EtO)(HO)Si(CH$_2$)$_3$]—S$_m$— [(CH$_2$)$_3$Si(OEt)$_2$[(OCH$_2$—CH$_2$)$_6$—OC$_4$H$_9$]],
[[C$_5$H$_{11}$O—(CH$_2$—CH$_2$O)$_2$](EtO)(HO)Si(CH$_2$)$_3$]—S$_m$— [(CH$_2$)$_3$Si(OEt)$_2$[(OCH$_2$—CH$_2$)$_2$OC$_5$H$_{11}$]], [[C$_5$H$_{11}$O—(CH$_2$—CH$_2$O)$_3$](EtO)(HO)Si(CH$_2$)$_3$]-S$_m$— [(CH$_2$)$_3$Si(OEt)$_2$[(OCH$_2$—CH$_2$)$_3$—OC$_5$H$_{11}$]], [[C$_5$H$_{11}$O—(CH$_2$—CH$_2$O)$_4$](EtO)(HO)Si(CH$_2$)$_3$]-S$_m$— [(CH$_2$)$_3$Si(OEt)$_2$[(OCH$_2$—CH$_2$)$_4$OC$_5$H$_{11}$]], [[C$_5$H$_{11}$O—(CH$_2$—CH$_2$O)$_5$](EtO)(HO)Si(CH$_2$)$_3$]—S$_m$— [(CH$_2$)$_3$Si(OEt)$_2$[(OCH$_2$—CH$_2$)$_5$OC$_5$H$_{11}$]], [[C$_5$H$_{11}$O—(CH$_2$—CH$_2$O)$_6$](EtO)(HO)Si(CH$_2$)$_3$]-S$_m$— [(CH$_2$)$_3$Si(OEt)$_2$[(OCH$_2$—CH$_2$)$_6$OC$_5$H$_{11}$]],
[[C$_6$H$_{13}$O—(CH$_2$—CH$_2$O)$_2$](EtO)(HO)Si(CH$_2$)$_3$]—S$_m$— [(CH$_2$)$_3$Si(OEt)$_2$[(OCH$_2$—CH$_2$)$_2$—OC$_6$H$_{13}$]], [[C$_6$H$_{13}$O—(CH$_2$—CH$_2$O)$_3$](EtO)(HO)Si(CH$_2$)$_3$]—S$_m$— [(CH$_2$)$_3$Si(OEt)$_2$[(OCH$_2$—CH$_2$)$_3$—OC$_6$H$_{13}$]], [[C$_6$H$_{13}$O—(CH$_2$—CH$_2$O)$_4$](EtO)(HO)Si(CH$_2$)$_3$]—S$_m$— [(CH$_2$)$_3$Si(OEt)$_2$[(OCH$_2$—CH$_2$)$_4$—OC$_6$H$_{13}$]], [[C$_6$H$_{13}$O—(CH$_2$—CH$_2$O)$_5$](EtO)(HO)Si(CH$_2$)$_3$]—S$_m$— [(CH$_2$)$_3$Si(OEt)$_2$[(OCH$_2$—CH$_2$)$_5$—OC$_6$H$_{13}$]], [[C$_6$H$_{13}$O—(CH$_2$—CH$_2$O)$_6$](EtO)(HO)Si(CH$_2$)$_3$]-S$_m$— [(CH$_2$)$_3$Si(OEt)$_2$[(OCH$_2$—CH$_2$)$_6$—OC$_6$H$_{13}$]],
[[C$_7$H$_{15}$O—(CH$_2$—CH$_2$O)$_2$](EtO)(HO)Si(CH$_2$)$_3$]—S$_m$— [(CH$_2$)$_3$Si(OEt)$_2$[(OCH$_2$—CH$_2$)$_2$—OC$_7$H$_{15}$]], [[C$_7$H$_{15}$O—(CH$_2$—CH$_2$O)$_3$](EtO)(HO)Si(CH$_2$)$_3$]-S$_m$— [(CH$_2$)$_3$Si(OEt)$_2$[(OCH$_2$—CH$_2$)$_3$—OC$_7$H$_{15}$]], [[C$_7$H$_{15}$O—(CH$_2$—CH$_2$O)$_4$](EtO)(HO)Si(CH$_2$)$_3$]—S$_m$— [(CH$_2$)$_3$Si(OEt)$_2$[(OCH$_2$—CH$_2$)$_4$OC$_7$H$_{15}$]], [[C$_7$H$_{15}$O—(CH$_2$—CH$_2$O)$_5$](EtO)(HO)Si(CH$_2$)$_3$]—S$_m$— [(CH$_2$)$_3$Si(OEt)$_2$[(OCH$_2$—CH$_2$)$_5$OC$_7$H$_{15}$]], [[C$_7$H$_{15}$O—(CH$_2$—CH$_2$O)$_6$](EtO)(HO)Si(CH$_2$)$_3$]-S$_m$— [(CH$_2$)$_3$Si(OEt)$_2$[(OCH$_2$—CH$_2$)$_6$OC$_7$H$_{15}$]],
[[C$_8$H$_{17}$O—(CH$_2$—CH$_2$O)$_2$](EtO)(HO)Si(CH$_2$)$_3$]—S$_m$— [(CH$_2$)$_3$Si(OEt)$_2$[(OCH$_2$—CH$_2$)$_2$OC$_8$H$_{17}$]], [[C$_8$H$_{17}$O—(CH$_2$—CH$_2$O)$_3$](EtO)(HO)Si(CH$_2$)$_3$]—S$_m$— [(CH$_2$)$_3$Si(OEt)$_2$[(OCH$_2$—CH$_2$)$_3$—OC$_8$H$_{17}$]], [[C$_8$H$_{17}$O—(CH$_2$—CH$_2$O)$_4$](EtO)(HO)Si(CH$_2$)$_3$]—S$_m$— [(CH$_2$)$_3$Si(OEt)$_2$[(OCH$_2$—CH$_2$)$_4$OC$_8$H$_{17}$]], [[C$_8$H$_{17}$O—(CH$_2$—CH$_2$O)$_5$](EtO)(HO)Si(CH$_2$)$_3$]—S$_m$— [(CH$_2$)$_3$Si(OEt)$_2$[(OCH$_2$—CH$_2$)$_5$—OC$_8$H$_{17}$]], [[C$_8$H$_{17}$O—(CH$_2$—CH$_2$O)$_6$](EtO)(HO)Si(CH$_2$)$_3$]—S$_m$— [(CH$_2$)$_3$Si(OEt)$_2$[(OCH$_2$—CH$_2$)$_6$—OC$_8$H$_{17}$]],
[[C$_9$H$_{19}$O—(CH$_2$—CH$_2$O)$_2$](EtO)(HO)Si(CH$_2$)$_3$]—S$_m$— [(CH$_2$)$_3$Si(OEt)$_2$[(OCH$_2$—CH$_2$)$_2$—OC$_9$H$_{19}$]], [[C$_9$H$_{19}$O—(CH$_2$—CH$_2$O)$_3$](EtO)(HO)Si(CH$_2$)$_3$]-S$_m$— [(CH$_2$)$_3$Si(OEt)$_2$[(OCH$_2$—CH$_2$)$_3$—OC$_9$H$_{19}$]], [[C$_9$H$_{19}$O—(CH$_2$—CH$_2$O)$_4$](EtO)(HO)Si(CH$_2$)$_3$]—S$_m$— [(CH$_2$)$_3$Si(OEt)$_2$[(OCH$_2$—CH$_2$)$_4$—OC$_9$H$_{19}$]], [[C$_9$H$_{19}$O—(CH$_2$—CH$_2$O)$_5$](EtO)(HO)Si(CH$_2$)$_3$]—S$_m$— [(CH$_2$)$_3$Si(OEt)$_2$[(OCH$_2$—CH$_2$)$_5$—OC$_9$H$_{19}$]], [[C$_9$H$_{19}$O—(CH$_2$—CH$_2$O)$_6$](EtO)(HO)Si(CH$_2$)$_3$]-S$_m$— [(CH$_2$)$_3$Si(OEt)$_2$[(OCH$_2$—CH$_2$)$_6$—OC$_9$H$_{19}$]],
[[C$_{10}$H$_{21}$O—(CH$_2$—CH$_2$O)$_2$](EtO)(HO)Si(CH$_2$)$_3$]-S$_m$— [(CH$_2$)$_3$Si(OEt)$_2$[(OCH$_2$—CH$_2$)$_2$—OC$_{10}$H$_{21}$]],
[[C$_{10}$H$_{21}$O—(CH$_2$—CH$_2$O)$_3$](EtO)(HO)Si(CH$_2$)$_3$]-S$_m$— [(CH$_2$)$_3$Si(OEt)$_2$[(OCH$_2$—CH$_2$)$_3$—OC$_{10}$H$_{21}$]],
[[C$_{10}$H$_{21}$O—(CH$_2$—CH$_2$O)$_4$](EtO)(HO)Si(CH$_2$)$_3$]—S$_m$— [(CH$_2$)$_3$Si(OEt)$_2$[(OCH$_2$—CH$_2$)$_4$—OC$_{10}$H$_{21}$]],
[[C$_{10}$H$_{21}$O—(CH$_2$—CH$_2$O)$_5$](EtO)(HO)Si(CH$_2$)$_3$]—S$_m$— [(CH$_2$)$_3$Si(OEt)$_2$[(OCH$_2$—CH$_2$)$_5$—OC$_{10}$H$_{21}$]],
[[C$_{10}$H$_{21}$O—(CH$_2$—CH$_2$O)$_6$](EtO)(HO)Si(CH$_2$)$_3$]—S$_m$— [(CH$_2$)$_3$Si(OEt)$_2$[(OCH$_2$—CH$_2$)$_6$—OC$_{10}$H$_{21}$]],
[[C$_{11}$H$_{23}$O—(CH$_2$—CH$_2$O)$_2$](EtO)(HO)Si(CH$_2$)$_3$]—S$_m$— [(CH$_2$)$_3$Si(OEt)$_2$[(OCH$_2$—CH$_2$)$_2$—OC$_{11}$H$_{23}$]],
[[C$_{11}$H$_{23}$O—(CH$_2$—CH$_2$O)$_3$](EtO)(HO)Si(CH$_2$)$_3$]—S$_m$— [(CH$_2$)$_3$Si(OEt)$_2$[(OCH$_2$—CH$_2$)$_3$—OC$_{11}$H$_{23}$]],
[[C$_{11}$H$_{23}$O—(CH$_2$—CH$_2$O)$_4$](EtO)(HO)Si(CH$_2$)$_3$]—S$_m$— [(CH$_2$)$_3$Si(OEt)$_2$[(OCH$_2$—CH$_2$)$_4$—OC$_{11}$H$_{23}$]],
[[C$_{11}$H$_{23}$O—(CH$_2$—CH$_2$O)$_5$](EtO)(HO)Si(CH$_2$)$_3$]—S$_m$— [(CH$_2$)$_3$Si(OEt)$_2$[(OCH$_2$—CH$_2$)$_5$—OC$_{11}$H$_{23}$]],
[[C$_{11}$H$_{23}$O—(CH$_2$—CH$_2$O)$_6$](EtO)(HO)Si(CH$_2$)$_3$]—S$_m$— [(CH$_2$)$_3$Si(OEt)$_2$[(OCH$_2$—CH$_2$)$_6$—OC$_{11}$H$_{23}$]],
[[C$_{12}$H$_{25}$O—(CH$_2$—CH$_2$O)$_2$](EtO)(HO)Si(CH$_2$)$_3$]—S$_m$— [(CH$_2$)$_3$Si(OEt)$_2$[OCH$_2$—CH$_2$)$_2$—OC$_{12}$H$_{25}$]],
[[C$_{12}$H$_{25}$O—(CH$_2$—CH$_2$O)$_3$](EtO)(HO)Si(CH$_2$)$_3$]—S$_m$— [(CH$_2$)$_3$Si(OEt)$_2$[(OCH$_2$—CH$_2$)$_3$—OC$_{12}$H$_{25}$]],
[[C$_{12}$H$_{25}$O—(CH$_2$—CH$_2$O)$_4$](EtO)(HO)Si(CH$_2$)$_3$]—S$_m$— [(CH$_2$)$_3$Si(OEt)$_2$[(OCH$_2$—CH$_2$)$_4$—OC$_{12}$H$_{25}$]],
[[C$_{12}$H$_{25}$O—(CH$_2$—CH$_2$O)$_5$](EtO)(HO)Si(CH$_2$)$_3$]—S$_m$— [(CH$_2$)$_3$Si(OEt)$_2$[(OCH$_2$—CH$_2$)$_5$—OC$_{12}$H$_{25}$]],
[[C$_{12}$H$_{25}$O—(CH$_2$—CH$_2$O)$_6$](EtO)(HO)Si(CH$_2$)$_3$]—S$_m$— [(CH$_2$)$_3$Si(OEt)$_2$[(OCH$_2$—CH$_2$)$_6$—OC$_{12}$H$_{25}$]],
[[C$_{13}$H$_{27}$O—(CH$_2$—CH$_2$O)$_2$](EtO)(HO)Si(CH$_2$)$_3$]—S$_m$— [(CH$_2$)$_3$Si(OEt)$_2$[(OCH$_2$—CH$_2$)$_2$—OC$_{13}$H$_{27}$]],
[[C$_{13}$H$_{27}$O—(CH$_2$—CH$_2$O)$_3$](EtO)(HO)Si(CH$_2$)$_3$]—S$_m$— [(CH$_2$)$_3$Si(OEt)$_2$[(OCH$_2$—CH$_2$)$_3$—OC$_{13}$H$_{27}$]],
[[C$_{13}$H$_{27}$O—(CH$_2$—CH$_2$O)$_4$](EtO)(HO)Si(CH$_2$)$_3$]—S$_m$— [(CH$_2$)$_3$Si(OEt)$_2$[(OCH$_2$—CH$_2$)$_4$—OC$_{13}$H$_{27}$]],
[[C$_{13}$H$_{27}$O—(CH$_2$—CH$_2$O)$_5$](EtO)(HO)Si(CH$_2$)$_3$]—S$_m$— [(CH$_2$)$_3$Si(OEt)$_2$[(OCH$_2$—CH$_2$)$_5$—OC$_{13}$H$_{27}$]],
[[C$_{13}$H$_{27}$O—(CH$_2$—CH$_2$O)$_6$](EtO)(HO)Si(CH$_2$)$_3$]—S$_m$— [(CH$_2$)$_3$Si(OEt)$_2$[(OCH$_2$—CH$_2$)$_6$—OC$_{13}$H$_{27}$]],
[[C$_{14}$H$_{29}$O—(CH$_2$—CH$_2$O)$_2$](EtO)(HO)Si(CH$_2$)$_3$]—S$_m$— [(CH$_2$)$_3$Si(OEt)$_2$[(OCH$_2$—CH$_2$)$_2$—OC$_{14}$H$_{29}$]],
[[C$_{14}$H$_{29}$O—(CH$_2$—CH$_2$O)$_3$](EtO)(HO)Si(CH$_2$)$_3$]—S$_m$— [(CH$_2$)$_3$Si(OEt)$_2$[(OCH$_2$—CH$_2$)$_3$—OC$_{14}$H$_{29}$]],
[[C$_{14}$H$_{29}$O—(CH$_2$—CH$_2$O)$_4$](EtO)(HO)Si(CH$_2$)$_3$]—S$_m$— [(CH$_2$)$_3$Si(OEt)$_2$[(OCH$_2$—CH$_2$)$_4$—OC$_{14}$H$_{29}$]],
[[C$_{14}$H$_{29}$O—(CH$_2$—CH$_2$O)$_5$](EtO)(HO)Si(CH$_2$)$_3$]—S$_m$— [(CH$_2$)$_3$Si(OEt)$_2$[(OCH$_2$—CH$_2$)$_5$—OC$_{14}$H$_{29}$]],
[[C$_{14}$H$_{29}$O—(CH$_2$—CH$_2$O)$_6$](EtO)(HO)Si(CH$_2$)$_3$]—S$_m$— [(CH$_2$)$_3$Si(OEt)$_2$[(OCH$_2$—CH$_2$)$_6$—OC$_{14}$H$_{29}$]],
[[C$_{15}$H$_{31}$O—(CH$_2$—CH$_2$O)$_2$](EtO)(HO)Si(CH$_2$)$_3$]-S$_m$— [(CH$_2$)$_3$Si(OEt)$_2$[(OCH$_2$—CH$_2$)$_2$—OC$_{15}$H$_{31}$]],
[[C$_{15}$H$_{31}$O—(CH$_2$—CH$_2$O)$_3$](EtO)(HO)Si(CH$_2$)$_3$]—S$_m$—

[(CH$_2$)$_3$Si(OEt)$_2$[(OCH$_2$—CH$_2$)$_3$—OC$_{15}$H$_{31}$]],
[[C$_{15}$H$_{31}$O—(CH$_2$—CH$_2$O)$_4$](EtO)(HO)Si(CH$_2$)$_3$]-S$_m$—[(CH$_2$)$_3$Si(OEt)$_2$[(OCH$_2$—CH$_2$)$_4$—OC$_{15}$H$_{31}$]],
[[C$_{15}$H$_{31}$O—(CH$_2$—CH$_2$O)$_5$](EtO)(HO)Si(CH$_2$)$_3$]-S$_m$—[(CH$_2$)$_3$Si(OEt)$_2$[(OCH$_2$—CH$_2$)$_5$—OC$_{15}$H$_{31}$]],
[[C$_{15}$H$_{31}$O—(CH$_2$—CH$_2$O)$_6$](EtO)(HO)Si(CH$_2$)$_3$]—S$_m$—[(CH$_2$)$_3$Si(OEt)$_2$[(OCH$_2$—CH$_2$)$_6$—OC$_{15}$H$_{31}$]],
[[C$_{16}$H$_{33}$O—(CH$_2$—CH$_2$O)$_2$](EtO)(HO)Si(CH$_2$)$_3$]-S$_m$—[(CH$_2$)$_3$Si(OEt)$_2$[(OCH$_2$—CH$_2$)$_2$—OC$_{16}$H$_{33}$]],
[[C$_{16}$H$_{33}$O—(CH$_2$—CH$_2$O)$_3$](EtO)(HO)Si(CH$_2$)$_3$]—S$_m$—[(CH$_2$)$_3$Si(OEt)$_2$[(OCH$_2$—CH$_2$)$_3$—OC$_{16}$H$_{33}$]],
[[C$_{16}$H$_{33}$O—(CH$_2$—CH$_2$O)$_4$](EtO)(HO)Si(CH$_2$)$_3$]-S$_m$—[(CH$_2$)$_3$Si(OEt)$_2$[(OCH$_2$—CH$_2$)$_4$—OC$_{16}$H$_{33}$]],
[[C$_{16}$H$_{33}$O—(CH$_2$—CH$_2$O)$_5$](EtO)(HO)Si(CH$_2$)$_3$]-S$_m$—[(CH$_2$)$_3$Si(OEt)$_2$[(OCH$_2$—CH$_2$)$_5$—OC$_{16}$H$_{33}$]],
[[C$_{16}$H$_{33}$O—(CH$_2$—CH$_2$O)$_6$](EtO)(HO)Si(CH$_2$)$_3$]—S$_m$—[(CH$_2$)$_3$Si(OEt)$_2$[(OCH$_2$—CH$_2$)$_6$—OC$_{16}$H$_{33}$]],
[[C$_{17}$H$_{35}$O—(CH$_2$—CH$_2$O)$_2$](EtO)(HO)Si(CH$_2$)$_3$]—S$_m$—[(CH$_2$)$_3$Si(OEt)$_2$[(OCH$_2$—CH$_2$)$_2$—OC$_{17}$H$_{35}$]],
[[C$_{17}$H$_{35}$O—(CH$_2$—CH$_2$O)$_3$](EtO)(HO)Si(CH$_2$)$_3$]—S$_m$—[(CH$_2$)$_3$Si(OEt)$_2$[(OCH$_2$—CH$_2$)$_3$—OC$_{17}$H$_{35}$]],
[[C$_{17}$H$_{35}$O—(CH$_2$—CH$_2$O)$_4$](EtO)(HO)Si(CH$_2$)$_3$]-S$_m$—[(CH$_2$)$_3$Si(OEt)$_2$[(OCH$_2$—CH$_2$)$_4$—OC$_{17}$H$_{35}$]],
[[C$_{17}$H$_{35}$O—(CH$_2$—CH$_2$O)$_5$](EtO)(HO)Si(CH$_2$)$_3$]—S$_m$—[(CH$_2$)$_3$Si(OEt)$_2$[(OCH$_2$—CH$_2$)$_5$—OC$_{17}$H$_{35}$]],
[[C$_{17}$H$_{35}$O—(CH$_2$—CH$_2$O)$_6$](EtO)(HO)Si(CH$_2$)$_3$]-S$_m$—[(CH$_2$)$_3$Si(OEt)$_2$[(OCH$_2$—CH$_2$)$_6$—OC$_{17}$H$_{35}$]],
[[C$_{18}$H$_{37}$O—(CH$_2$—CH$_2$O)$_2$](EtO)(HO)Si(CH$_2$)$_3$]-S$_m$—[(CH$_2$)$_3$Si(OEt)$_2$[(OCH$_2$—CH$_2$)$_2$—OC$_{18}$H$_{37}$]],
[[C$_{18}$H$_{37}$O—(CH$_2$—CH$_2$O)$_3$](EtO)(HO)Si(CH$_2$)$_3$]—S$_m$—[(CH$_2$)$_3$Si(OEt)$_2$[(OCH$_2$—CH$_2$)$_3$—OC$_{18}$H$_{37}$]],
[[C$_{18}$H$_{37}$O—(CH$_2$—CH$_2$O)$_4$](EtO)(HO)Si(CH$_2$)$_3$]—S$_m$—[(CH$_2$)$_3$Si(OEt)$_2$[(OCH$_2$—CH$_2$)$_4$—OC$_{18}$H$_{37}$]],
[[C$_{18}$H$_{37}$O—(CH$_2$—CH$_2$O)$_5$](EtO)(HO)Si(CH$_2$)$_3$]—S$_m$—[(CH$_2$)$_3$Si(OEt)$_2$[(OCH$_2$—CH$_2$)$_5$—OC$_{18}$H$_{37}$]], or
[[C$_{18}$H$_{37}$O—(CH$_2$—CH$_2$O)$_6$](EtO)(HO)Si(CH$_2$)$_3$]—S$_m$—[(CH$_2$)$_3$Si(OEt)$_2$[(OCH$_2$—CH$_2$)$_6$—OC$_{18}$H$_{37}$]],
[[C$_3$H$_7$O—(CH$_2$—CH$_2$O)$_2$]$_2$(HO)Si(CH$_2$)$_3$]—S$_m$—[(CH$_2$)$_3$Si(OEt)[(OCH$_2$—CH$_2$)$_2$—OC$_3$H$_7$]$_2$], [[C$_3$H$_7$O—(CH$_2$—CH$_2$O)$_3$]$_2$(HO)Si(CH$_2$)$_3$]—S$_m$—[(CH$_2$)$_3$Si(OEt)[(OCH$_2$—CH$_2$)$_3$—OC$_3$H$_7$]$_2$], [[C$_3$H$_7$O—(CH$_2$—CH$_2$O)$_4$]$_2$(HO)Si(CH$_2$)$_3$]—S$_m$—[(CH$_2$)$_3$Si(OEt)[(OCH$_2$—CH$_2$)$_4$—OC$_3$H$_7$]$_2$], [[C$_3$H$_7$O—(CH$_2$—CH$_2$O)$_5$]$_2$(HO)Si(CH$_2$)$_3$]—S$_m$—[(CH$_2$)$_3$Si(OEt)[(OCH$_2$—CH$_2$)$_5$—OC$_3$H$_7$]$_2$],
[[C$_3$H$_7$O—(CH$_2$—CH$_2$O)$_6$]$_2$(HO)Si(CH$_2$)$_3$]—S$_m$—[(CH$_2$)$_3$Si(OEt)[(OCH$_2$—CH$_2$)$_6$—OC$_3$H$_7$]$_2$], [[C$_4$H$_9$O—(CH$_2$—CH$_2$O)$_2$]$_2$(HO)Si(CH$_2$)$_3$]—S$_m$—[(CH$_2$)$_3$Si(OEt)[(OCH$_2$—CH$_2$)$_2$—OC$_4$H$_9$]$_2$], [[C$_4$H$_9$O—(CH$_2$—CH$_2$O)$_3$]$_2$(HO)Si(CH$_2$)$_3$]—S$_m$—[(CH$_2$)$_3$Si(OEt)[(OCH$_2$—CH$_2$)$_3$—OC$_4$H$_9$]$_2$], [[C$_4$H$_9$O—(CH$_2$—CH$_2$O)$_4$]$_2$(HO)Si(CH$_2$)$_3$]—S$_m$—[(CH$_2$)$_3$Si(OEt)[(OCH$_2$—CH$_2$)$_4$—OC$_4$H$_9$]$_2$], [[C$_4$H$_9$O—(CH$_2$—CH$_2$O)$_5$]$_2$(HO)Si(CH$_2$)$_3$]—S$_m$—[(CH$_2$)$_3$Si(OEt)[(OCH$_2$—CH$_2$)$_5$—OC$_4$H$_9$]$_2$], [[C$_4$H$_9$O—(CH$_2$—CH$_2$O)$_6$]$_2$(HO)Si(CH$_2$)$_3$]—S$_m$—[(CH$_2$)$_3$Si(OEt)[(OCH$_2$—CH$_2$)$_6$—OC$_4$H$_9$]$_2$],
[[C$_5$H$_{11}$O—(CH$_2$—CH$_2$O)$_2$]$_2$(HO)Si(CH$_2$)$_3$]—S$_m$—[(CH$_2$)$_3$Si(OEt)[(OCH$_2$—CH$_2$)$_2$—OC$_5$H$_{11}$]$_2$], [[C$_5$H$_{11}$O—(CH$_2$—CH$_2$O)$_3$]$_2$(HO)Si(CH$_2$)$_3$]—S$_m$—[(CH$_2$)$_3$Si(OEt)[(OCH$_2$—CH$_2$)$_3$—OC$_5$H$_{13}$]$_2$], [[C$_5$H$_{11}$O—(CH$_2$—CH$_2$O)$_4$]$_2$(HO)Si(CH$_2$)$_3$]—S$_m$[(CH$_2$)$_3$Si(OEt)[(OCH$_2$—CH$_2$)$_4$—C$_5$H$_{11}$]$_2$], [[C$_5$H$_{11}$O—(CH$_2$—CH$_2$O)$_5$]$_2$(HO)Si(CH$_2$)$_3$]-S$_m$—[(CH$_2$)$_3$Si(OEt)[(OCH$_2$—CH$_2$)$_5$OC$_5$H$_{11}$]$_2$], [[C$_5$H$_{11}$O—(CH$_2$—CH$_2$O)$_6$]$_2$(HO)Si(CH$_2$)$_3$]-S$_m$— [(CH$_2$)$_3$Si(OEt)[(OCH$_2$—CH$_2$)$_6$—OC$_5$H$_{11}$]$_2$],
[[C$_6$H$_{13}$O—(CH$_2$—CH$_2$O)$_2$]$_2$(HO)Si(CH$_2$)$_3$]—S$_m$—[(CH$_2$)$_3$Si(OEt)[(OCH$_2$—CH$_2$)$_2$—OC$_6$H$_{13}$]$_2$], [[C$_6$H$_{13}$O—(CH$_2$—CH$_2$O)$_3$]$_2$(HO)Si(CH$_2$)$_3$]—S$_m$—[(CH$_2$)$_3$Si(OEt)[(OCH$_2$—CH$_2$)$_3$—OC$_6$H$_{13}$]$_2$], [[C$_6$H$_{13}$O—(CH$_2$—CH$_2$O)$_4$]$_2$(HO)Si(CH$_2$)$_3$]—S$_m$—[(CH$_2$)$_3$Si(OEt)[(OCH$_2$—CH$_2$)$_4$—OC$_6$H$_{13}$]$_2$], [[C$_6$H$_{13}$O—(CH$_2$—CH$_2$O)$_5$]$_2$(HO)Si(CH$_2$)$_3$]-S$_m$—[(CH$_2$)$_3$Si(OEt)[(OCH$_2$—CH$_2$)$_5$—OC$_6$H$_{13}$]$_2$], [[C$_6$H$_{13}$O—(CH$_2$—CH$_2$O)$_6$]$_2$(HO)Si(CH$_2$)$_3$]-S$_m$—[(CH$_2$)$_3$Si(OEt)[(OCH$_2$—CH$_2$)$_6$—OC$_6$H$_{13}$]$_2$],
[[C$_7$H$_{15}$O—(CH$_2$—CH$_2$O)$_2$]$_2$(HO)Si(CH$_2$)$_3$]—S$_m$—[(CH$_2$)$_3$Si(OEt)[(OCH$_2$—CH$_2$)$_2$—OC$_7$H$_{15}$]$_2$], [[C$_7$H$_{15}$O—(CH$_2$—CH$_2$O)$_3$]$_2$(HO)Si(CH$_2$)$_3$]-S$_m$—[(CH$_2$)$_3$Si(OEt)[(OCH$_2$—CH$_2$)$_3$—OC$_7$H$_{15}$]$_2$], [[C$_7$H$_{15}$O—(CH$_2$—CH$_2$O)$_4$]$_2$(HO)Si(CH$_2$)$_3$]—S$_m$—[(CH$_2$)$_3$Si(OEt)[(OCH$_2$—CH$_2$)$_4$—OC$_7$H$_{15}$]$_2$], [[C$_7$H$_{15}$O—(CH$_2$—CH$_2$O)$_5$]$_2$(HO)Si(CH$_2$)$_3$]-S$_m$—[(CH$_2$)$_3$Si(OEt)[(OCH$_2$—CH$_2$)$_5$—OC$_7$H$_{15}$]$_2$], [[C$_7$H$_{15}$O—(CH$_2$—CH$_2$O)$_6$]$_2$(HO)Si(CH$_2$)$_3$]—S$_m$—[(CH$_2$)$_3$Si(OEt)[(OCH$_2$—CH$_2$)$_6$—OC$_7$H$_{15}$]$_2$],
[[C$_8$H$_{17}$O—(CH$_2$—CH$_2$O)$_2$]$_2$(HO)Si(CH$_2$)$_3$]—S$_m$—[(CH$_2$)$_3$Si(OEt)[(OCH$_2$—CH$_2$)$_2$—OC$_8$H$_{17}$]$_2$], [[C$_8$H$_{17}$O—(CH$_2$—CH$_2$O)$_3$]$_2$(HO)Si(CH$_2$)$_3$]—S$_m$—[(CH$_2$)$_3$Si(OEt)[(OCH$_2$—CH$_2$)$_3$—OC$_8$H$_{17}$]$_2$], [[C$_8$H$_{17}$O—(CH$_2$—CH$_2$O)$_4$]$_2$(HO)Si(CH$_2$)$_3$]—S$_m$[(CH$_2$)$_3$Si(OEt)[(OCH$_2$—CH$_2$)$_4$—OC$_8$H$_{17}$]$_2$], [[C$_8$H$_{17}$O—(CH$_2$—CH$_2$O)$_5$]$_2$(HO)Si(CH$_2$)$_3$]-S$_m$—[(CH$_2$)$_3$Si(OEt)[(OCH$_2$—CH$_2$)$_5$—OC$_8$H$_{17}$]$_2$], [[C$_8$H$_{17}$O—(CH$_2$—CH$_2$O)$_6$]$_2$(HO)Si(CH$_2$)$_3$]—S$_m$—[(CH$_2$)$_3$Si(OEt)[(OCH$_2$—CH$_2$)$_6$OC$_8$H$_{17}$]$_2$],
[[C$_9$H$_{19}$O—(CH$_2$—CH$_2$O)$_2$]$_2$(HO)Si(CH$_2$)$_3$]-S$_m$—[(CH$_2$)$_3$Si(OEt)[(OCH$_2$—CH$_2$)$_2$—OC$_9$H$_{19}$]$_2$], [[C$_9$H$_{19}$O—(CH$_2$—CH$_2$O)$_3$]$_2$(HO)Si(CH$_2$)$_3$]—S$_m$—[(CH$_2$)$_3$Si(OEt)[(OCH$_2$—CH$_2$)$_3$—OC$_9$H$_{19}$]$_2$], [[C$_9$H$_{19}$O—(CH$_2$—CH$_2$O)$_4$]$_2$(HO)Si(CH$_2$)$_3$]-S$_m$—[(CH$_2$)$_3$Si(OEt)[(OCH$_2$—CH$_2$)$_4$—OC$_9$H$_{19}$]$_2$], [[C$_9$H$_{19}$O—(CH$_2$—CH$_2$O)$_5$]$_2$(HO)Si(CH$_2$)$_3$]-S$_m$—[(CH$_2$)$_3$Si(OEt)[(OCH$_2$—CH$_2$)$_5$—OC$_9$H$_{19}$]$_2$], [[C$_9$H$_{19}$O—(CH$_2$—CH$_2$O)$_6$]$_2$(HO)Si(CH$_2$)$_3$]—S$_m$—[(CH$_2$)$_3$Si(OEt)[(OCH$_2$—CH$_2$)$_6$—OC$_9$H$_{19}$]$_2$],
[[C$_{10}$H$_{21}$O—(CH$_2$—CH$_2$O)$_2$]$_2$(HO)Si(CH$_2$)$_3$]-S$_m$—(CH$_2$)$_3$Si(OEt)[(OCH$_2$—CH$_2$)$_2$—OC$_{10}$H$_{21}$]$_2$], [[C$_{10}$H$_{21}$O—(CH$_2$—CH$_2$O)$_3$]$_2$(HO)Si(CH$_2$)$_3$]-S$_m$—(CH$_2$)$_3$Si(OEt)[(OCH$_2$—CH$_2$)$_3$—OC$_{10}$H$_{21}$]$_2$], [[C$_{10}$H$_{21}$O—(CH$_2$—CH$_2$O)$_4$]$_2$(HO)Si(CH$_2$)$_3$]—S$_m$—[(CH$_2$)$_3$Si(OEt)[(OCH$_2$—CH$_2$)$_4$—OC$_{10}$H$_{21}$]$_2$], [[C$_{10}$H$_{21}$O—(CH$_2$—CH$_2$O)$_5$]$_2$(HO)Si(CH$_2$)$_3$]-S$_m$—[(CH$_2$)$_3$Si[(OCH$_2$—CH$_2$)$_5$—OC$_{10}$H$_{21}$]$_2$], [[C$_{10}$H$_{21}$O—(CH$_2$—CH$_2$O)$_6$]$_2$(HO)Si(CH$_2$)$_3$]-S$_m$— [(CH$_2$)$_3$Si(OEt)[(OCH$_2$—CH$_2$)$_6$—OC$_{10}$H$_{21}$]$_2$],
[[C$_{11}$H$_{23}$O—(CH$_2$—CH$_2$O)$_2$]$_2$(HO)Si(CH$_2$)$_3$]-S$_m$—(CH$_2$)$_3$Si(OEt)[(OCH$_2$—CH$_2$)$_2$—OC$_{11}$H$_{23}$]$_2$], [[C$_{11}$H$_{23}$O—(CH$_2$—CH$_2$O)$_3$]$_2$(HO)Si(CH$_2$)$_3$]-S$_m$—(CH$_2$)$_3$Si(OEt)[(OCH$_2$—CH$_2$)$_3$—OC$_{11}$H$_{23}$]$_2$], [[C$_{11}$H$_{23}$O—(CH$_2$—CH$_2$O)$_4$]$_2$(HO)Si(CH$_2$)$_3$]—S$_m$—[(CH$_2$)$_3$Si(OEt)[(OCH$_2$—CH$_2$)$_4$—OC$_{11}$H$_{23}$]$_2$], [[C$_{11}$H$_{23}$O—(CH$_2$—CH$_2$O)$_5$]$_2$(HO)Si(CH$_2$)$_3$]—S$_m$—[(CH$_2$)$_3$Si(OEt)[(OCH$_2$—CH$_2$)$_5$—OC$_{11}$H$_{23}$]$_2$], [[C$_{11}$H$_{23}$O—(CH$_2$—CH$_2$O)$_6$]$_2$(HO)Si(CH$_2$)$_3$]-S$_m$—[(CH$_2$)$_3$Si(OEt)[(OCH$_2$—CH$_2$)$_6$—OC$_{11}$H$_{23}$]$_2$],
[[C$_{12}$H$_{25}$O—(CH$_2$—CH$_2$O)$_2$]$_2$(HO)Si(CH$_2$)$_3$]—S$_m$—[(CH$_2$)$_3$Si(OEt)[(OCH$_2$—CH$_2$)$_2$—OC$_{12}$H$_{25}$]$_2$], [[C$_{12}$H$_{25}$O—(CH$_2$—CH$_2$O)$_3$]$_2$(HO)Si(CH$_2$)$_3$]—S$_m$—[(CH$_2$)$_3$Si(OEt)[(OCH$_2$—CH$_2$)$_3$—OC$_{12}$H$_{25}$]$_2$], [[C$_{12}$H$_{25}$O—(CH$_2$—CH$_2$O)$_4$]$_2$(HO)Si(CH$_2$)$_3$]—S$_m$—[(CH$_2$)$_3$Si(OEt)[(OCH$_2$—CH$_2$)$_4$—OC$_{12}$H$_{25}$]$_2$], [[C$_{12}$H$_{25}$O—(CH$_2$—CH$_2$O)$_5$]$_2$(HO)Si(CH$_2$)$_3$]—S$_m$—[(CH$_2$)$_3$Si(OEt)[(OCH$_2$—CH$_2$)$_5$—OC$_{12}$H$_{25}$]$_2$], [[C$_{12}$H$_{25}$O—(CH$_2$—CH$_2$O)$_6$]$_2$(HO)Si(CH$_2$)$_3$]—S$_m$—[(CH$_2$)$_3$Si(OEt)[(OCH$_2$—CH$_2$)$_6$—OC$_{12}$H$_{25}$]$_2$],
[[C$_{13}$H$_{27}$O—(CH$_2$—CH$_2$O)$_2$]$_2$(HO)Si(CH$_2$)$_3$]—S$_m$—[(CH$_2$)$_3$Si(OEt)[(OCH$_2$—CH$_2$)$_2$—OC$_{13}$H$_{27}$]$_2$], [[C$_{13}$H$_{27}$O—(CH$_2$—CH$_2$O)$_3$]$_2$(HO)Si(CH$_2$)$_3$]—S$_m$—[(CH$_2$)$_3$Si(OEt)[(OCH$_2$—CH$_2$)$_3$—OC$_{13}$H$_{27}$]$_2$], [[C$_{13}$H$_{27}$O—(CH$_2$—CH$_2$O)$_4$]$_2$(HO)Si(CH$_2$)$_3$]—S$_m$—[(CH$_2$)$_3$Si(OEt)[(OCH$_2$—CH$_2$)$_4$—OC$_{13}$H$_{27}$]$_2$],

[[C$_{13}$H$_{27}$O—(CH$_2$—CH$_2$O)$_5$]$_2$(HO)Si(CH$_2$)$_3$]-S$_m$—[(CH$_2$)$_3$ Si(OEt)[(OCH$_2$—CH$_2$)$_5$—OC$_{13}$H$_{27}$]$_2$],
[[C$_{13}$H$_{27}$O—(CH$_2$—CH$_2$O)$_6$]$_2$(HO)Si(CH$_2$)$_3$]—S$_m$—[(CH$_2$)$_3$Si(OEt)[(OCH$_2$—CH$_2$)$_6$—OC$_{13}$H$_{27}$]$_2$],
[[C$_{14}$H$_{29}$O—(CH$_2$—CH$_2$O)$_2$]$_2$(HO)Si(CH$_2$)$_3$]—S$_m$—[(CH$_2$)$_3$Si(OEt)[(OCH$_2$—CH$_2$)$_2$—OC$_{14}$H$_{29}$]$_2$],
[[C$_{14}$H$_{29}$O—(CH$_2$—CH$_2$O)$_3$]$_2$(HO)Si(CH$_2$)$_3$]—S$_m$—[(CH$_2$)$_3$Si(OEt)[(OCH$_2$—CH$_2$)$_3$—OC$_{14}$H$_{29}$]$_2$],
[[C$_{14}$H$_{29}$O—(CH$_2$—CH$_2$O)$_4$]$_2$(HO)Si(CH$_2$)$_3$]—S$_m$—[(CH$_2$)$_3$Si(OEt)[(OCH$_2$—CH$_2$)$_4$—OC$_{14}$H$_{29}$]$_2$],
[[C$_{14}$H$_{29}$O—(CH$_2$—CH$_2$O)$_5$]$_2$(HO)Si(CH$_2$)$_3$]—S$_m$—[(CH$_2$)$_3$Si(OEt)[(OCH$_2$—CH$_2$)$_5$—OC$_{14}$H$_{29}$]$_2$],
[[C$_{14}$H$_{29}$O—(CH$_2$—CH$_2$O)$_6$]$_2$(HO)Si(CH$_2$)$_3$]—S$_m$—[(CH$_2$)$_3$Si(OEt)[(OCH$_2$—CH$_2$)$_6$—OC$_{14}$H$_{29}$]$_2$],
[[C$_{15}$H$_{31}$O—(CH$_2$—CH$_2$O)$_2$]$_2$(HO)Si(CH$_2$)$_3$]—S$_m$—[(CH$_2$)$_3$Si(OEt)[(OCH$_2$—CH$_2$)$_2$—OC$_{15}$H$_{31}$]$_2$],
[[C$_{15}$H$_{31}$O—(CH$_2$—CH$_2$O)$_3$]$_2$(HO)Si(CH$_2$)$_3$]—S$_m$—[(CH$_2$)$_3$Si(OEt)[(OCH$_2$—CH$_2$)$_3$—OC$_{15}$H$_{31}$]$_2$],
[[C$_{15}$H$_{31}$O—(CH$_2$—CH$_2$O)$_4$]$_2$(HO)Si(CH$_2$)$_3$]—S$_m$—[(CH$_2$)$_3$Si(OEt)[(OCH$_2$—CH$_2$)$_4$—OC$_{15}$H$_{31}$]$_2$],
[[C$_{15}$H$_{31}$O—(CH$_2$—CH$_2$O)$_5$]$_2$(HO)Si(CH$_2$)$_3$]—S$_m$—[(CH$_2$)$_3$Si(OEt)[(OCH$_2$—CH$_2$)$_5$—OC$_{15}$H$_{31}$]$_2$],
[[C$_{16}$H$_{31}$O—(CH$_2$—CH$_2$O)$_6$]$_2$(HO)Si(CH$_2$)$_3$]—S$_m$—[(CH$_2$)$_3$Si(OEt)[(OCH$_2$—CH$_2$)$_6$—OC$_{16}$H$_{31}$]$_2$],
[[C$_{16}$H$_{33}$O—(CH$_2$—CH$_2$O)$_2$]$_2$(HO)Si(CH$_2$)$_3$)—]S$_m$—[(CH$_2$)$_3$Si(OEt)[(OCH$_2$—CH$_2$)$_2$—OC$_{16}$H$_{33}$]$_2$],
[[C$_{16}$H$_{33}$O—(CH$_2$—CH$_2$O)$_3$]$_2$(HO)Si(CH$_2$)$_3$]—S$_m$—[(CH$_2$)$_3$Si (OEt)[(OCH$_2$—CH$_2$)$_3$—OC$_{16}$H$_{33}$]$_2$],
[[C$_{16}$H$_{33}$O—(CH$_2$—CH$_2$O)$_4$]$_2$(HO)Si(CH$_2$)$_3$]-S$_m$—[(CH$_2$)$_3$ Si(OEt)[(OCH$_2$—CH$_2$)$_4$—OC$_{16}$H$_{33}$]$_2$],
[[C$_{16}$H$_{33}$O—(CH$_2$—CH$_2$O)$_5$]$_2$(HO)Si(CH$_2$)$_3$]-S$_m$—[(CH$_2$)$_3$ Si(OEt)[(OCH$_2$—CH$_2$)$_5$—OC$_{16}$H$_{33}$]$_2$)],
[[C$_{16}$H$_{33}$O—(CH$_2$—CH$_2$O)$_6$]$_2$(HO)Si(CH$_2$)$_3$]—S$_m$—[(CH$_2$)$_3$Si(OEt)[(OCH$_2$—CH$_2$)$_6$—OC$_{16}$H$_{33}$]$_2$],
[[C$_{17}$H$_{35}$O—(CH$_2$—CH$_2$O)$_2$]$_2$(HO)Si(CH$_2$)$_3$]-S$_m$—[(CH$_2$)$_3$ Si(OEt)[(OCH$_2$—CH$_2$)$_2$—OC$_{17}$H$_{36}$]$_2$],
[[C$_{17}$H$_{35}$O—(CH$_2$—CH$_2$O)$_3$]$_2$(HO)Si(CH$_2$)$_3$]-S$_m$—[(CH$_2$)$_3$ Si(OEt)[(OCH$_2$—CH$_2$)$_3$—OC$_{17}$H$_{35}$]$_2$],
[[C$_{17}$H$_{36}$O—(CH$_2$—CH$_2$O)$_4$]$_2$(HO)Si(CH$_2$)$_3$]-S$_m$—[(CH$_2$)$_3$ Si(OEt)[(OCH$_2$—CH$_2$)$_4$—OC$_{17}$H$_{36}$]$_2$],
[[C$_{17}$H$_{36}$O—(CH$_2$—CH$_2$O)$_5$]$_2$(HO)Si(CH$_2$)$_3$]-S$_m$—[(CH$_2$)$_3$ Si(OEt)[(OCH$_2$—CH$_2$)$_5$—OC$_{17}$H$_{35}$]$_2$],
[[C$_{17}$H$_{35}$O—(CH$_2$—CH$_2$O)$_6$]$_2$(HO)Si(CH$_2$)$_3$]—S$_m$—[(CH$_2$)$_3$Si(OEt)[(OCH$_2$—CH$_2$)$_6$—OC$_{17}$H$_{36}$]$_2$],
[[C$_{18}$H$_{37}$O—(CH$_2$—CH$_2$O)$_2$]$_2$(HO)Si(CH$_2$)$_3$]-S$_m$—[(CH$_2$)$_3$ Si(OEt)[(OCH$_2$—CH$_2$)$_2$—OC$_{18}$H$_{37}$]$_2$],
[[C$_{18}$H$_{37}$O—(CH$_2$—CH$_2$O)$_3$]$_2$(HO)Si(CH$_2$)$_3$]-S$_m$—[(CH$_2$)$_3$ Si(OEt)[(OCH$_2$—CH$_2$)$_3$—OC$_{18}$H$_{37}$]$_2$],
[[C$_{18}$H$_{37}$O—(CH$_2$—CH$_2$O)$_4$]$_2$(HO)Si(CH$_2$)$_3$]-S$_m$—[(CH$_2$)$_3$ Si(OEt)[(OCH$_2$—CH$_2$)$_4$—OC$_{18}$H$_{37}$]$_2$],
[[C$_{18}$H$_{37}$O—(CH$_2$—CH$_2$O)$_5$]$_2$(HO)Si(CH$_2$)$_3$]-S$_m$—[(CH$_2$)$_3$ Si(OEt)[(OCH$_2$—CH$_2$)$_5$—OC$_{18}$H$_{37}$]$_2$], or
[[C$_{18}$H$_{37}$O—(CH$_2$—CH$_2$O)$_6$]$_2$(HO)Si(CH$_2$)$_3$]—S$_m$—[(CH$_2$)$_3$Si(OEt)[(OCH$_2$—CH$_2$)$_6$—OC$_{18}$H$_{37}$]$_2$], where the alkyl moieties can be unbranched or branched.

Preferred compounds of the general formula IV can be:
[[C$_3$H$_7$O—(CH$_2$—CH$_2$O)$_2$](Me)(MeO)Si(CH$_2$)$_3$]$_2$S$_m$,
[[C$_3$H$_7$O—(CH$_2$—CH$_2$O)$_3$](Me)(MeO)Si(CH$_2$)$_3$]$_2$S$_m$,
[[C$_3$H$_7$O—(CH$_2$—CH$_2$O)$_4$](Me)(MeO)Si(CH$_2$)$_3$]$_2$S$_m$,
[[C$_3$H$_7$O—(CH$_2$—CH$_2$O)$_5$](Me)(MeO)Si(CH$_2$)$_3$]$_2$S$_m$,
[[C$_3$H$_7$O—(CH$_2$—CH$_2$O)$_6$](Me)(MeO)Si(CH$_2$)$_3$]$_2$S$_m$,
[[C$_4$H$_9$O—(CH$_2$—CH$_2$O)$_2$](Me)(MeO)Si(CH$_2$)$_3$]$_2$S$_m$,
[[C$_4$H$_9$O—(CH$_2$—CH$_2$O)$_3$](Me)(MeO)Si(CH$_2$)$_3$]$_2$S$_m$,
[[C$_4$H$_9$O—(CH$_2$—CH$_2$O)$_4$](Me)(MeO)Si(CH$_2$)$_3$]$_2$S$_m$,
[[C$_4$H$_9$O—(CH$_2$—CH$_2$O)$_5$](Me)(MeO)Si(CH$_2$)$_3$]$_2$S$_m$,
[[C$_4$H$_9$O—(CH$_2$—CH$_2$O)$_6$](Me)(MeO)Si(CH$_2$)$_3$]$_2$S$_m$,
[[C$_5$H$_{11}$O—(CH$_2$—CH$_2$O)$_2$](Me)(MeO)Si(CH$_2$)$_3$]$_2$S$_m$,
[[C$_5$H$_{11}$O—(CH$_2$—CH$_2$O)$_3$](Me)(MeO)Si(CH$_2$)$_3$]$_2$S$_m$,
[[C$_5$H$_{11}$O—(CH$_2$—CH$_2$O)$_4$](Me)(MeO)Si(CH$_2$)$_3$]$_2$S$_m$,
[[C$_5$H$_{11}$O—(CH$_2$—CH$_2$O)$_5$](Me)(MeO)Si(CH$_2$)$_3$]$_2$S$_m$,
[[C$_5$H$_{11}$—(CH$_2$—CH$_2$O)$_6$](Me)(MeO)Si(CH$_2$)$_3$]$_2$S$_m$,
[[C$_6$H$_{13}$O—(CH$_2$—CH$_2$O)$_2$](Me)(MeO)Si(CH$_2$)$_3$]$_2$S$_m$,
[[C$_6$H$_{13}$O—(CH$_2$—CH$_2$O)$_3$](Me)(MeO)Si(CH$_2$)$_3$]$_2$S$_m$,
[[C$_6$H$_{13}$O—(CH$_2$—CH$_2$O)$_4$](Me)(MeO)Si(CH$_2$)$_3$]$_2$S$_m$,
[[C$_6$H$_{13}$—(CH$_2$—CH$_2$O)$_5$](Me)(MeO)Si(CH$_2$)$_3$]$_2$S$_m$,
[[C$_6$H$_{13}$O—(CH$_2$, —CH$_2$O)$_6$](Me)(MeO)Si(CH$_2$)$_3$]$_2$S$_m$,
[[C$_7$H$_5$O—(CH$_2$—CH$_2$O)$_2$](Me)(MeO)Si(CH$_2$)$_3$]$_2$S$_m$,
[[C$_7$H$_{15}$O—(CH$_2$—CH$_2$O)$_3$](Me)(MeO)Si(CH$_2$)$_3$]$_2$S$_m$,
[[C$_7$H$_{15}$O—(CH$_2$—CH$_2$O)$_4$](Me)(MeO)Si(CH$_2$)$_3$]$_2$S$_m$,
[[C$_7$H$_{15}$O—(CH$_2$—CH$_2$O)$_5$](Me)(MeO)Si(CH$_2$)$_3$]$_2$S$_m$,
[[C$_7$H$_{15}$O—(CH$_2$—CH$_2$O)$_6$](Me)(MeO)Si(CH$_2$)$_3$]$_2$S$_m$,
[[C$_8$H$_{17}$O—(CH$_2$—CH$_2$O)$_2$](Me)(MeO)Si(CH$_2$)$_3$]$_2$S$_m$,
[[C$_8$H$_{17}$O—(CH$_2$—CH$_2$O)$_3$](Me)(MeO)Si(CH$_2$)$_3$]$_2$S$_m$,
[[C$_8$H$_{17}$O—(CH$_2$—CH$_2$O)$_4$](Me)(MeO)Si(CH$_2$)$_3$]$_2$S$_m$,
[[C$_8$H$_{17}$O—(CH$_2$—CH$_2$O)$_5$](Me)(MeO)Si(CH$_2$)$_3$]$_2$S$_m$,
[[C$_8$H$_{17}$O—(CH$_2$—CH$_2$O)$_6$](Me)(MeO)Si(CH$_2$)$_3$]$_2$S$_m$,
[[C$_9$H$_{19}$O—(CH$_2$—CH$_2$O)$_2$](Me)(MeO)Si(CH$_2$)$_3$]$_2$S$_m$,
[[C$_9$H$_{19}$O—(CH$_2$—CH$_2$O)$_3$](Me)(MeO)Si(CH$_2$)$_3$]$_2$S$_m$,
[[C$_9$H$_{19}$O—(CH$_2$—CH$_2$O)$_4$](Me)(MeO)Si(CH$_2$)$_3$]$_2$S$_m$,
[[C$_9$H$_{19}$O—(CH$_2$—CH$_2$O)$_5$](Me)(MeO)Si(CH$_2$)$_3$]$_2$S$_m$,
[[C$_9$H$_{19}$O—(CH$_2$—CH$_2$O)$_6$](Me)(MeO)Si(CH$_2$)$_3$]$_2$S$_m$,
[[C$_{10}$H$_{21}$O—(CH$_2$—CH$_2$O)$_2$](Me)(MeO)Si(CH$_2$)$_3$]$_2$S$_m$,
[[C$_{10}$H$_{21}$O—(CH$_2$—CH$_2$O)$_3$](Me)(MeO)Si(CH$_2$)$_3$]$_2$S$_m$,
[[C$_{10}$H$_{21}$O—(CH$_2$—CH$_2$O)$_4$](Me)(MeO)Si(CH$_2$)$_3$]$_2$S$_m$,
[[C$_{10}$H$_{21}$O—(CH$_2$—CH$_2$O)$_5$](Me)(MeO)Si(CH$_2$)$_3$]$_2$S$_m$,
[[C$_{10}$H$_{21}$O—(CH$_2$—CH$_2$O)$_6$](Me)(MeO)Si(CH$_2$)$_3$]$_2$S$_m$,
[[C$_{11}$H$_{23}$O—(CH$_2$—CH$_2$O)$_2$](Me)(MeO)Si(CH$_2$)$_3$]$_2$S$_m$,
[[C$_{11}$H$_{23}$O—(CH$_2$—CH$_2$O)$_3$](Me)(MeO)Si(CH$_2$)$_3$]$_2$S$_m$,
[[C$_{11}$H$_{23}$O—(CH$_2$—CH$_2$O)$_4$](Me)(MeO)Si(CH$_2$)$_3$]$_2$S$_m$,
[[C$_{11}$H$_{23}$O—(CH$_2$—CH$_2$O)$_5$](Me)(MeO)Si(CH$_2$)$_3$]$_2$S$_m$,
[[C$_{11}$H$_{23}$O—(CH$_2$—CH$_2$O)$_6$](Me)(MeO)Si(CH$_2$)$_3$]$_2$S$_m$,
[[C$_{12}$H$_{25}$O—(CH$_2$—CH$_2$O)$_2$](Me)(MeO)Si(CH$_2$)$_3$]$_2$S$_m$,
[[C$_{12}$H$_{25}$O—(CH$_2$—CH$_2$O)$_3$](Me)(MeO)Si(CH$_2$)$_3$]$_2$S$_m$,
[[C$_{12}$H$_{25}$O—(CH$_2$—CH$_2$O)$_4$](Me)(MeO)Si(CH$_2$)$_3$]$_2$S$_m$,
[[C$_{12}$H$_{25}$O—(CH$_2$—CH$_2$O)$_5$](Me)(MeO)Si(CH$_2$)$_3$]$_2$S$_m$,
[[C$_{12}$H$_{25}$O—(CH$_2$—CH$_2$O)$_6$](Me)(MeO)Si(CH$_2$)$_3$]$_2$S$_m$,
[[C$_{13}$H$_{27}$O—(CH$_2$—CH$_2$O)$_2$](Me)(MeO)Si(CH$_2$)$_3$]$_2$S$_m$,
[[C$_{13}$H$_{27}$O—(CH$_2$—CH$_2$O)$_3$](Me)(MeO)Si(CH$_2$)$_3$]$_2$S$_m$,
[[C$_{13}$H$_{27}$O—(CH$_2$—CH$_2$O)$_4$](Me)(MeO)Si(CH$_2$)$_3$]$_2$S$_m$,
[[C$_{13}$H$_{27}$O—(CH$_2$—CH$_2$O)$_5$](Me)(MeO)Si(CH$_2$)$_3$]$_2$S$_m$,
[[C$_{13}$H$_{27}$O—(CH$_2$—CH$_2$O)$_6$](Me)(MeO)Si(CH$_2$)$_3$]$_2$S$_m$,
[[C$_{14}$H$_{29}$O—(CH$_2$—CH$_2$O)$_2$](Me)(MeO)Si(CH$_2$)$_3$]$_2$S$_m$,
[[C$_{14}$H$_{29}$O—(CH$_2$—CH$_2$O)$_3$](Me)(MeO)Si(CH$_2$)$_3$]$_2$S$_m$,
[[C$_{14}$H$_{29}$O—(CH$_2$—CH$_2$O)$_4$](Me)(MeO)Si(CH$_2$)$_3$]$_2$S$_m$,
[[C$_{14}$H$_{29}$O—(CH$_2$—CH$_2$O)$_5$](Me)(MeO)Si(CH$_2$)$_3$]$_2$S$_m$,
[[C$_{14}$H$_{29}$O—(CH$_2$—CH$_2$O)$_6$](Me)(MeO)Si(CH$_2$)$_3$]$_2$S$_m$,
[[C$_{15}$H$_{31}$O—(CH$_2$—CH$_2$O)$_2$](Me)(MeO)Si(CH$_2$)$_3$]$_2$S$_m$,
[[C$_{15}$H$_{31}$O—(CH$_2$—CH$_2$O)$_3$](Me)(MeO)Si(CH$_2$)$_3$]$_2$S$_m$,
[[C$_{15}$H$_{31}$O—(CH$_2$—CH$_2$O)$_4$](Me)(MeO)Si(CH$_2$)$_3$]$_2$S$_m$,
[[C$_{15}$H$_{31}$O—(CH$_2$—CH$_2$O)$_5$](Me)(MeO)Si(CH$_2$)$_3$]$_2$S$_m$,
[[C$_{15}$H$_{31}$O—(CH$_2$—CH$_2$O)$_6$](Me)(MeO)Si(CH$_2$)$_3$]$_2$S$_m$,
[[C$_{16}$H$_{33}$O—(CH$_2$—CH$_2$O)$_2$](Me)(MeO)Si(CH$_2$)$_3$]$_2$S$_m$,
[[C$_{16}$H$_{33}$O—(CH$_2$—CH$_2$O)$_3$](Me)(MeO)Si(CH$_2$)$_3$]$_2$S$_m$,
[[C$_{16}$H$_{33}$O—(CH$_2$—CH$_2$O)$_4$](Me)(MeO)Si(CH$_2$)$_3$]$_2$S$_m$,
[[C$_{16}$H$_{33}$O—(CH$_2$—CH$_2$O)$_5$](Me)(MeO)Si(CH$_2$)$_3$]$_2$S$_m$,
[[C$_{16}$H$_{33}$O—(CH$_2$—CH$_2$O)$_6$](Me)(MeO)Si(CH$_2$)$_3$]$_2$S$_m$,
[[C$_{17}$H$_{35}$O—(CH$_2$—CH$_2$O)$_2$](Me)(MeO)Si(CH$_2$)$_3$]$_2$S$_m$,
[[C$_{17}$H$_{35}$O—(CH$_2$—CH$_2$O)$_3$](Me)(MeO)Si(CH$_2$)$_3$]$_2$S$_m$,
[[C$_{17}$H$_{35}$O—(CH$_2$—CH$_2$O)$_4$](Me)(MeO)Si(CH$_2$)$_3$]$_2$S$_m$,
[[C$_{17}$H$_{35}$O—(CH$_2$—CH$_2$O)$_5$](Me)(MeO)Si(CH$_2$)$_3$]$_2$S$_m$,
[[C$_{17}$H$_{35}$O—(CH$_2$—CH$_2$O)$_6$](Me)(MeO)Si(CH$_2$)$_3$]$_2$S$_m$,
[[C$_{18}$H$_{37}$O—(CH$_2$—CH$_2$O)$_2$](Me)(MeO)Si(CH$_2$)$_3$]$_2$S$_m$,
[[C$_{18}$H$_{37}$O—(CH$_2$—CH$_2$O)$_3$](Me)(MeO)Si(CH$_2$)$_3$]$_2$S$_m$,
[[C$_{18}$H$_{37}$O—(CH$_2$—CH$_2$O)$_4$](Me)(MeO)Si(CH$_2$)$_3$]$_2$S$_m$,
[[C$_{18}$H$_{37}$O—(CH$_2$—CH$_2$O)$_5$](Me)(MeO)Si(CH$_2$)$_3$]$_2$S$_m$,

[[C₃H₇O—(CH₂—CH₂O)₂](Me)(EtO)Si(CH₂)₃]₂Sₘ,
[[C₃H₇O—(CH₂—CH₂O)₃](Me)(EtO)Si(CH₂)₃]₂Sₘ,
[[C₃H₇O—(CH₂—CH₂O)₄](Me)(EtO)Si(CH₂)₃]₂Sₘ,
[[C₃H₇O—(CH₂—CH₂O)₅](Me)(EtO)Si(CH₂)₃]₂Sₘ,
[[C₃H₇O—(CH₂—CH₂O)₆](Me)(EtO)Si(CH₂)₃]₂Sₘ,
[[C₄H₉O—(CH₂—CH₂O)₂](Me)(EtO)Si(CH₂)₃]₂Sₘ,
[[C₄H₉O—(CH₂—CH₂O)₃](Me)(EtO)Si(CH₂)₃]₂Sₘ,
[[C₄H₉O—(CH₂—CH₂O)₄](Me)(EtO)Si(CH₂)₃]₂Sₘ,
[[C₄H₉O—(CH₂—CH₂O)₅](Me)(EtO)Si(CH₂)₃]₂Sₘ,
[[C₄H₉O—(CH₂—CH₂O)₆](Me)(EtO)Si(CH₂)₃]₂Sₘ,
[[C₅H₁₁O—(CH₂—CH₂O)₂](Me)(EtO)Si(CH₂)₃]₂Sₘ,
[[C₅H₁₁O—(CH₂—CH₂O)₃](Me)(EtO)Si(CH₂)₃]₂Sₘ,
[[C₅H₁₁O—(CH₂—CH₂O)₄](Me)(EtO)Si(CH₂)₃]₂Sₘ,
[[C₅H₁₁O—(CH₂—CH₂O)₅](Me)(EtO)Si(CH₂)₃]₂Sₘ,
[[C₅H₁₁O—(CH₂—CH₂O)₆](Me)(EtO)Si(CH₂)₃]₂Sₘ,
[[C₆H₁₃O—(CH₂—CH₂O)₂](Me)(EtO)Si(CH₂)₃]₂Sₘ,
[[C₆H₁₃O—(CH₂—CH₂O)₃](Me)(EtO)Si(CH₂)₃]₂Sₘ,
[[C₆H₁₃O—(CH₂—CH₂O)₄](Me)(EtO)Si(CH₂)₃]₂Sₘ,
[[C₆H₁₃O—(CH₂—CH₂O)₅](Me)(EtO)Si(CH₂)₃]₂Sₘ,
[[C₆H₁₃O—(CH₂—CH₂O)₆](Me)(EtO)Si(CH₂)₃]₂Sₘ,
[[C₇H₁₅O—(CH₂—CH₂O)₂](Me)(EtO)Si(CH₂)₃]₂Sₘ,
[[C₇H₁₅O—(CH₂—CH₂O)₃](Me)(EtO)Si(CH₂)₃]₂Sₘ,
[[C₇H₁₅O—(CH₂—CH₂O)₄](Me)(EtO)Si(CH₂)₃]₂Sₘ,
[[C₇H₁₅O—(CH₂—CH₂O)₅](Me)(EtO)Si(CH₂)₃]₂Sₘ,
[[C₇H₅O—(CH₂—CH₂O)₆](Me)(EtO)Si(CH₂)₃]₂Sₘ,
[[C₈H₁₇O—(CH₂—CH₂O)₂](Me)(EtO)Si(CH₂)₃]₂Sₘ,
[[C₈H₁₇O—(CH₂—CH₂O)₃](Me)(EtO)Si(CH₂)₃]₂Sₘ,
[[C₈H₁₇O—(CH₂—CH₂O)₄](Me)(EtO)Si(CH₂)₃]₂Sₘ,
[[C₈H₁₇O—(CH₂—CH₂O)₅](Me)(EtO)Si(CH₂)₃]₂Sₘ,
[[C₈H₁₇O—(CH₂—CH₂O)₆](Me)(EtO)Si(CH₂)₃]₂Sₘ
[[C₉H₁₉O—(CH₂—CH₂O)₂](Me)(EtO)Si(CH₂)₃]₂Sₘ,
[[C₉H₁₉O—(CH₂—CH₂O)₃](Me)(EtO)Si(CH₂)₃]₂Sₘ,
[[C₉H₁₉O—(CH₂—CH₂O)₄](Me)(EtO)Si(CH₂)₃]₂Sₘ,
[[C₉H₁₉O—(CH₂—CH₂O)₅](Me)(EtO)Si(CH₂)₃]₂Sₘ,
[[C₉H₁₉O—(CH₂—CH₂O)₆](Me)(EtO)Si(CH₂)₃]₂Sₘ,
[[C₁₀H₂₁O—(CH₂—CH₂O)₂](Me)(EtO)Si(CH₂)₃]₂Sₘ,
[[C₁₀H₂₁O—(CH₂—CH₂O)₃](Me)(EtO)Si(CH₂)₃]₂Sₘ,
[[C₁₀H₂₁O—(CH₂—CH₂O)₄](Me)(EtO)Si(CH₂)₃]₂Sₘ,
[[C₁₀H₂₁O—(CH₂—CH₂O)₅](Me)(EtO)Si(CH₂)₃]₂Sₘ,
[[C₁₀H₂₁O—(CH₂—CH₂O)₆](Me)(EtO)Si(CH₂)₃]₂Sₘ,
[[C₁₁H₂₃O—(CH₂—CH₂O)₂](Me)(EtO)Si(CH₂)₃]₂Sₘ,
[[C₁₁H₂₃O—(CH₂—CH₂O)₃](Me)(EtO)Si(CH₂)₃]₂Sₘ,
[[C₁₁H₂₃O—(CH₂—CH₂O)₄](Me)(EtO)Si(CH₂)₃]₂Sₘ,
[[C₁₁H₂₃O—(CH₂—CH₂O)₅](Me)(EtO)Si(CH₂)₃]₂Sₘ,
[[C₁₁H₂₃O—(CH₂—CH₂O)₆](Me)(EtO)Si(CH₂)₃]₂Sₘ,
[[C₁₂H₂₅O—(CH₂—CH₂O)₂](Me)(EtO)Si(CH₂)₃]₂Sₘ,
[[C₁₂H₂₅O—(CH₂—CH₂O)₃](Me)(EtO)Si(CH₂)₃]₂Sₘ,
[[C₁₂H₂₅O—(CH₂—CH₂O)₄](Me)(EtO)Si(CH₂)₃]₂Sₘ,
[[C₁₂H₂₅O—(CH₂—CH₂O)₅](Me)(EtO)Si(CH₂)₃]₂Sₘ,
[[C₁₂H₂₅O—(CH₂—CH₂O)₆](Me)(EtO)Si(CH₂)₃]₂Sₘ,
[[C₁₃H₂₇O—(CH₂—CH₂O)₂](Me)(EtO)Si(CH₂)₃]₂Sₘ,
[[C₁₃H₂₇O—(CH₂—CH₂O)₃](Me)(EtO)Si(CH₂)₃]₂Sₘ,
[[C₁₃H₂₇O—(CH₂—CH₂O)₄](Me)(EtO)Si(CH₂)₃]₂Sₘ,
[[C₁₃H₂₇O—(CH₂—CH₂O)₅](Me)(EtO)Si(CH₂)₃]₂Sₘ,
[[C₁₃H₂₇O—(CH₂—CH₂O)₆](Me)(EtO)Si(CH₂)₃]₂Sₘ,
[[C₁₄H₂₉O—(CH₂—CH₂O)₂](Me)(EtO)Si(CH₂)₃]₂Sₘ,
[[C₁₄H₂₉O—(CH₂—CH₂O)₃](Me)(EtO)Si(CH₂)₃]₂Sₘ,
[[C₁₄H₂₉O—(CH₂—CH₂O)₄](Me)(EtO)Si(CH₂)₃]₂Sₘ,
[[C₁₄H₂₉O—(CH₂—CH₂O)₅](Me)(EtO)Si(CH₂)₃]₂Sₘ,
[[C₁₄H₂₉O—(CH₂—CH₂O)₆](Me)(EtO)Si(CH₂)₃]₂Sₘ,
[[C₁₅H₃₁O—(CH₂—CH₂O)₂](Me)(EtO)Si(CH₂)₃]₂Sₘ,
[[C₁₅H₃₁O—(CH₂—CH₂O)₃](Me)(EtO)Si(CH₂)₃]₂Sₘ,
[[C₁₅H₃₁O—(CH₂—CH₂O)₄](Me)(EtO)Si(CH₂)₃]₂Sₘ,
[[C₁₅H₃₁O—(CH₂—CH₂O)₅](Me)(EtO)Si(CH₂)₃]₂Sₘ,
[[C₁₅H₃₁O—(CH₂—CH₂O)₆](Me)(EtO)Si(CH₂)₃]₂Sₘ,
[[C₁₆H₃₃O—(CH₂—CH₂O)₂](Me)(EtO)Si(CH₂)₃]₂Sₘ,
[[C₁₆H₃₃O—(CH₂—CH₂O)₃](Me)(EtO)Si(CH₂)₃]₂Sₘ,
[[C₁₆H₃₃O—(CH₂—CH₂O)₄](Me)(EtO)Si(CH₂)₃]₂Sₘ,
[[C₁₆H₃₃O—(CH₂—CH₂O)₅](Me)(EtO)Si(CH₂)₃]₂Sₘ,
[[C₁₆H₃₃O—(CH₂—CH₂O)₆](Me)(EtO)Si(CH₂)₃]₂Sₘ,
[[C₁₇H₃₅O—(CH₂—CH₂O)₂](Me)(EtO)Si(CH₂)₃]₂Sₘ,
[[C₁₇H₃₅O—(CH₂—CH₂O)₃](Me)(EtO)Si(CH₂)₃]₂Sₘ,
[[C₁₇H₃₅O—(CH₂—CH₂O)₄](Me)(EtO)Si(CH₂)₃]₂Sₘ,
[[C₁₇H₃₅O—(CH₂—CH₂O)₅](Me)(EtO)Si(CH₂)₃]₂Sₘ,
[[C₁₇H₃₆O—(CH₂—CH₂O)₆](Me)(EtO)Si(CH₂)₃]₂Sₘ,
[[C₁₈H₃₇O—(CH₂—CH₂O)₂](Me)(EtO)Si(CH₂)₃]₂Sₘ,
[[C₁₈H₃₇O—(CH₂—CH₂O)₃](Me)(EtO)Si(CH₂)₃]₂Sₘ,
[[C₁₈H₃₇O—(CH₂—CH₂O)₄](Me)(EtO)Si(CH₂)₃]₂Sₘ,
[[C₁₈H₃₇O—(CH₂—CH₂O)₅](Me)(EtO)Si(CH₂)₃]₂Sₘ,
[[C₁₈H₃₇O—(CH₂—CH₂O)₆](Me)(EtO)Si(CH₂)₃]₂Sₘ,
[[C₃H₇O—(CH₂—CH₂O)₂](MeO)₂Si(CH₂)₃]₂Sₘ,
[[C₃H₇O—(CH₂—CH₂O)₃](MeO)₂Si(CH₂)₃]₂Sₘ,
[[C₃H₇O—(CH₂—CH₂O)₄](MeO)₂Si(CH₂)₃]₂Sₘ,
[[C₃H₇O—(CH₂—CH₂O)₅](MeO)₂Si(CH₂)₃]₂Sₘ,
[[C₃H₇O—(CH₂—CH₂O)₆](MeO)₂Si(CH₂)₃]₂Sₘ,
[[C₄H₉O—(CH₂—CH₂O)₂](MeO)₂Si(CH₂)₃]₂Sₘ,
[[C₄H₉O—(CH₂—CH₂O)₃](MeO)₂Si(CH₂)₃]₂Sₘ,
[[C₄H₉O—(CH₂—CH₂O)₄](MeO)₂Si(CH₂)₃]₂Sₘ,
[[C₄H₉O—(CH₂—CH₂O)₅](MeO)₂Si(CH₂)₃]₂Sₘ,
[[C₄H₉O—(CH₂—CH₂O)₆](MeO)₂Si(CH₂)₃]₂Sₘ,
[[C₅H₁₁O—(CH₂—CH₂O)₂](MeO)₂Si(CH₂)₃]₂Sₘ,
[[C₅H₁₁O—(CH₂—CH₂O)₃](MeO)₂Si(CH₂)₃]₂Sₘ,
[[C₅H₁₁O—(CH₂—CH₂O)₄](MeO)₂Si(CH₂)₃]₂Sₘ,
[[C₅H₁₁—(CH₂—CH₂O)₅](MeO)₂Si(CH₂)₃]₂Sₘ,
[[C₅H₁₁O—(CH₂—CH₂O)₆](MeO)₂Si(CH₂)₃]₂Sₘ,
[[C₆H₁₃O—(CH₂—CH₂O)₂](MeO)₂Si(CH₂)₃]₂Sₘ,
[[C₆H₁₃O—(CH₂—CH₂O)₃](MeO)₂Si(CH₂)₃]₂Sₘ,
[[C₆H₁₃O—(CH₂—CH₂O)₄](MeO)₂Si(CH₂)₃]₂Sₘ,
[[C₆H₁₃O—(CH₂—CH₂O)₅](MeO)₂Si(CH₂)₃]₂Sₘ,
[[C₆H₁₃O—(CH₂—CH₂O)₆](MeO)₂Si(CH₂)₃]₂Sₘ,
[[C₇H₁₅O—(CH₂—CH₂O)₂](MeO)₂Si(CH₂)₃]₂Sₘ,
[[C₇H₆O—(CH₂—CH₂O)₃](MeO)₂Si(CH₂)₃]₂Sₘ,
[[C₇H₁₅O—(CH₂—CH₂O)₄](MeO)₂Si(CH₂)₃]₂Sₘ,
[[C₇H₁₅O—(CH₂—CH₂O)₅](MeO)₂S(CH₂)₃]₂Sₘ,
[[C₇H₁₅O—(CH₂—CH₂O)₆](MeO)₂Si(CH₂)₃]₂Sₘ,
[[C₈H₁₇O—(CH₂—CH₂O)₂](MeO)₂Si(CH₂)₃]₂Sₘ,
[[C₈H₁₇O—(CH₂—CH₂O)₃](MeO)₂Si(CH₂)₃]₂Sₘ,
[[C₈H₁₇O—(CH₂—CH₂O)₄](MeO)₂Si(CH₂)₃]₂Sₘ,
[[C₈H₁₇O—(CH₂—CH₂O)₅](MeO)₂Si(CH₂)₃]₂Sₘ,
[[C₈H₁₇O—(CH₂—CH₂O)₆](MeO)₂Si(CH₂)₃]₂Sₘ,
[[C₉H₁₉O—(CH₂—CH₂O)₂](MeO)₂Si(CH₂)₃]₂Sₘ,
[[C₉H₁₉O—(CH₂—CH₂O)₃](MeO)₂Si(CH₂)₃]₂Sₘ,
[[C₉H₁₉O—(CH₂—CH₂O)₄](MeO)₂Si(CH₂)₃]₂Sₘ,
[[C₉H₁₉—(CH₂—CH₂O)₅](MeO)₂Si(CH₂)₃]₂Sₘ,
[[C₉H₁₉O—(CH₂—CH₂O)₆](MeO)₂Si(CH₂)₃]₂Sₘ,
[[C₁₀H₂₁O—(CH₂—CH₂O)₂](MeO)₂Si(CH₂)₃]₂Sₘ,
[[C₁₀H₂₁O—(CH₂—CH₂O)₃](MeO)₂Si(CH₂)₃]₂Sₘ,
[[C₁₀H₂₁O—(CH₂—CH₂O)₄](MeO)₂Si(CH₂)₃]₂Sₘ,
[[C₁₀H₂₁O—(CH₂—CH₂O)₅](MeO)₂Si(CH₂)₃]₂Sₘ,
[[C₁₀H₂₁O—(CH₂—CH₂O)₆](MeO)₂Si(CH₂)₃]₂Sₘ,
[[C₁₁H₂₃O—(CH₂—CH₂O)₂](MeO)₂Si(CH₂)₃]₂Sₘ,
[[C₁₁H₂₃O—(CH₂—CH₂O)₃](MeO)₂Si(CH₂)₃]₂Sₘ,
[[C₁₁H₂₃O—(CH₂—CH₂O)₄](MeO)₂Si(CH₂)₃]₂Sₘ,
[[C₁₁H₂₃O—(CH₂—CH₂O)₅](MeO)₂Si(CH₂)₃]₂Sₘ,
[[C₁₁H₂₃O—(CH₂—CH₂O)₆](MeO)₂Si(CH₂)₃]₂Sₘ,
[[C₁₂H₂₅O—(CH₂—CH₂O)₂](MeO)₂Si(CH₂)₃]₂Sₘ,
[[C₁₂H₂₅O—(CH₂—CH₂O)₃](MeO)₂Si(CH₂)₃]₂Sₘ,
[[C₁₂H₂₅O—(CH₂—CH₂O)₄](MeO)₂Si(CH₂)₃]₂Sₘ,
[[C₁₂H₂₅O—(CH₂—CH₂O)₅](MeO)₂Si(CH₂)₃]₂Sₘ,
[[C₁₂H₂₅O—(CH₂—CH₂O)₆](MeO)₂Si(CH₂)₃]₂Sₘ,
[[C₁₃H₂₇O—(CH₂—CH₂O)₂](MeO)₂Si(CH₂)₃]₂Sₘ,
[[C₁₃H₂₇O—(CH₂—CH₂O)₃](MeO)₂Si(CH₂)₃]₂Sₘ,
[[C₁₃H₂₇O—(CH₂—CH₂O)₄](MeO)₂Si(CH₂)₃]₂Sₘ,

[[C₁₃H₂₇O—(CH₂—CH₂O)₅](MeO)₂Si(CH₂)₃]₂S_m,
[[C₁₃H₂₇O—(CH₂—CH₂O)₆](MeO)₂Si(CH₂)₃]₂S_m,
[[C₁₄H₂₉O—(CH₂—CH₂O)₂](MeO)₂Si(CH₂)₃]₂S_m,
[[C₁₄H₂₉O—(CH₂—CH₂O)₃](MeO)₂Si(CH₂)₃]₂S_m,
[[C₁₄H₂₉O—(CH₂—CH₂O)₄](MeO)₂Si(CH₂)₃]₂S_m,
[[C₁₄H₂₉O—(CH₂—CH₂O)₅](MeO)₂Si(CH₂)₃]₂S_m,
[[C₁₄H₂₉O—(CH₂—CH₂O)₆](MeO)₂Si(CH₂)₃]₂S_m,
[[C₁₆H₃₃O—(CH₂—CH₂O)₂](MeO)₂Si(CH₂)₃]₂S_m,
[[C₁₆H₃₃O—(CH₂—CH₂O)₃](MeO)₂Si(CH₂)₃]₂S_m,
[[C₁₆H₃₃O—(CH₂—CH₂O)₄](MeO)₂Si(CH₂)₃]₂S_m,
[[C₁₆H₃₃O—(CH₂—CH₂O)₅](MeO)₂Si(CH₂)₃]₂S_m,
[[C₁₆H₃₃O—(CH₂—CH₂O)₆](MeO)₂Si(CH₂)₃]₂S_m,
[[C₁₈H₃₇O—(CH₂—CH₂O)₂](MeO)₂Si(CH₂)₃]₂S_m,
[[C₁₈H₃₇O—(CH₂—CH₂O)₃](MeO)₂Si(CH₂)₃]₂S_m,
[[C₁₈H₃₇O—(CH₂—CH₂O)₄](MeO)₂Si(CH₂)₃]₂S_m,
[[C₁₈H₃₇O—(CH₂—CH₂O)₅](MeO)₂Si(CH₂)₃]₂S_m,
[[C₁₈H₃₇O—(CH₂—CH₂O)₆](MeO)₂Si(CH₂)₃]₂S_m,
[[C₃H₇O—(CH₂—CH₂O)₂]₂(MeO)Si(CH₂)₃]₂S_m,
[[C₃H₇O—(CH₂—CH₂O)₃]₂(MeO)Si(CH₂)₃]₂S_m,
[[C₃H₇O—(CH₂—CH₂O)₄]₂(MeO)Si(CH₂)₃]₂S_m,
[[C₃H₇O—(CH₂—CH₂O)₅]₂(MeO)Si(CH₂)₃]₂S_m,
[[C₃H₇O—(CH₂—CH₂O)₆]₂(MeO)Si(CH₂)₃]₂S_m,
[[C₄H₉O—(CH₂—CH₂O)₂]₂(MeO)Si(CH₂)₃]₂S_m,
[[C₄H₉O—(CH₂—CH₂O)₃]₂(MeO)Si(CH₂)₃]₂S_m,
[[C₄H₉O—(CH₂—CH₂O)₄]₂(MeO)Si(CH₂)₃]₂S_m,
[[C₄H₉O—(CH₂—CH₂O)₅]₂(MeO)Si(CH₂)₃]₂S_m,
[[C₄H₉O—(CH₂—CH₂O)₆]₂(MeO)Si(CH₂)₃]₂S_m,
[[C₅H₁₁O—(CH₂—CH₂O)₂]₂(MeO)Si(CH₂)₃]₂S_m,
[[C₅H₁₁O—(CH₂—CH₂O)₃]₂(MeO)Si(CH₂)₃]₂S_m,
[[C₅H₁₁O—(CH₂—CH₂O)₄]₂(MeO)Si(CH₂)₃]₂S_m,
[[C₅H₁₁O—(CH₂—CH₂O)₅]₂(MeO)Si(CH₂)₃]₂S_m,
[[C₅H₁₁—(CH₂—CH₂O)₆]₂(MeO)Si(CH₂)₃]₂S_m,
[[C₆H₁₃O—(CH₂—CH₂O)₂]₂(MeO)Si(CH₂)₃]₂S_m,
[[C₆H₁₃O—(CH₂—CH₂O)₃]₂(MeO)Si(CH₂)₃]₂S_m,
[[C₆H₁₃O—(CH₂—CH₂O)₄]₂(MeO)Si(CH₂)₃]₂S_m,
[[C₆H₁₃O—(CH₂—CH₂O)₅]₂(MeO)Si(CH₂)₃]₂S_m,
[[C₆H₁₃O—(CH₂—CH₂O)₆]₂(MeO)Si(CH₂)₃]₂S_m,
[[C₇H₁₅O—(CH₂—CH₂O)₂]₂(MeO) Si (CH₂)₃]₂S_m,
[[C₇H₁₅O—(CH₂—CH₂O)₃]₂ (MeO)Si(CH₂)₃]₂S_m,
[[C₇H₁₅O—(CH₂—CH₂O)₄]₂(MeO)Si(CH₂)₃]₂S_m,
[[C₇H₁₅O—(CH₂—CH₂O)₅]₂(MeO)Si(CH₂)₃]₂S_m,
[[C₇H₁₅—(CH₂—CH₂O)₆]₂(MeO)Si(CH₂)₃]₂S_m,
[[C₈H₁₇O—(CH₂—CH₂O)₂]₂(MeO)Si(CH₂)₃]₂S_m,
[[C₈H₁₇O—(CH₂—CH₂O)₃]₂(MeO)Si(CH₂)₃]₂S_m,
[[C₈H₁₇O—(CH₂—CH₂O)₄]₂(MeO)Si(CH₂)₃]₂S_m,
[[C₈H₁₇O—(CH₂—CH₂O)₅]₂(MeO)Si(CH₂)₃]₂S_m,
[[C₈H₁₇O—(CH₂—CH₂O)₆]₂(MeO)Si(CH₂)₃]₂S_m,
[[C₉H₁₉O—(CH₂—CH₂O)₂]₂(MeO)Si(CH₂)₃]₂S_m,
[[C₉H₁₉O—(CH₂—CH₂O)₃]₂(MeO)Si(CH₂)₃]₂S_m,
[[C₉H₁₉O—(CH₂—CH₂O)₄]₂(MeO)Si(CH₂)₃]₂S_m,
[[C₉H₁₉O—(CH₂—CH₂O)₅]₂(MeO)Si(CH₂)₃]₂S_m,
[[C₉H₁₉O—(CH₂—CH₂O)₆]₂(MeO)Si(CH₂)₃]₂S_m,
[[C₁₀H₂₁O—(CH₂—CH₂O)₂]₂ (MeO)Si(CH₂)₃]₂S_m,
[[C₁₀H₂₁—(CH₂—CH₂O)₃]₂(MeO)Si(CH₂)₃]₂S_m,
[[C₁₀H₂₁O—(CH₂—CH₂O)₄]₂ (MeO)Si(CH₂)₃]₂S_m,
[[C₁₀H₂₁O—(CH₂—CH₂O)₅]₂(MeO)Si(CH₂)₃]₂S_m,
[[C₁₀H₂₁O—(CH₂—CH₂O)₆]₂(MeO)Si(CH₂)₃]₂S_m,
[[C₁₁H₂₃—(CH₂—CH₂O)₂]₂(MeO)Si(CH₂)₃]₂S_m,
[[C₁₁H₂₃O—(CH₂—CH₂O)₃]₂(MeO)Si(CH₂)₃]₂S_m,
[[C₁₁H₂₃O—(CH₂—CH₂O)₄]₂ (MeO)Si(CH₂)₃]₂S_m,
[[C₁₁H₂₃O—(CH₂—CH₂O)₅]₂(MeO)Si(CH₂)₃]₂S_m,
[[C₁₁H₂₃O—(CH₂—CH₂O)₆]₂ (MeO)Si(CH₂)₃]₂S_m,
[[C₁₂H₂₅O—(CH₂—CH₂O)₂]₂(MeO)Si(CH₂)₃]₂S_m,
[[C₁₂H₂₅O—(CH₂—CH₂O)₃]₂(MeO)Si(CH₂)₃]₂S_m,
[[C₁₂H₂₅O—(CH₂—CH₂O)₄]₂(MeO)Si(CH₂)₃]₂S_m,
[[C₁₂H₂₅O—(CH₂—CH₂O)₅]₂(MeO)Si(CH₂)₃]₂S_m,
[[C₁₂H₂₅O—(CH₂—CH₂O)₆]₂(MeO)Si(CH₂)₃]₂S_m,

[[C₁₃H₂₇O—(CH₂—CH₂O)₂]₂(MeO)Si(CH₂)₃]₂S_m,
[[C₁₃H₂₇O—(CH₂—CH₂O)₃]₂(MeO)Si(CH₂)₃]₂S_m,
[[C₁₃H₂₇O—(CH₂—CH₂O)₄]₂(MeO)Si(CH₂)₃]₂S_m,
[[C₁₃H₂₇O—(CH₂—CH₂O)₅]₂ (MeO)Si(CH₂)₃]₂S_m,
[[C₁₃H₂₇O—(CH₂—CH₂O)₆]₂(MeO)Si(CH₂)₃]₂S_m,
[[C₁₄H₂₉O—(CH₂—CH₂O)₂]₂(MeO)Si(CH₂)₃]₂S_m,
[[C₁₄H₂₉O—(CH₂—CH₂O)₃]₂(MeO)Si(CH₂)₃]₂S_m,
[[C₁₄H₂₉O—(CH₂—CH₂O)₄]₂(MeO)Si(CH₂)₃]₂S_m,
[[C₁₄H₂₉O—(CH₂—CH₂O)₅]₂(MeO)Si(CH₂)₃]₂S_m,
[[C₁₄H₂₉O—(CH₂—CH₂O)₆]₂(MeO)Si(CH₂)₃]₂S_m,
[[C₁₆H₃₃O—(CH₂—CH₂O)₂]₂(MeO)Si(CH₂)₃]₂S_m,
[[C₁₆H₃₃O—(CH₂—CH₂O)₃]₂(MeO)Si(CH₂)₃]₂S_m,
[[C₁₆H₃₃O—(CH₂—CH₂O)₄]₂(MeO)Si(CH₂)₃]₂S_m,
[[C₁₆H₃₃O—(CH₂—CH₂O)₅]₂(MeO)Si(CH₂)₃]₂S_m,
[[C₁₆H₃₃O—(CH₂—CH₂O)₆]₂(MeO)Si(CH₂)₃]₂S_m,
[[C₁₈H₃₇O—(CH₂—CH₂O)₂]₂(MeO)Si(CH₂)₃]₂S_m,
[[C₁₈H₃₇O—(CH₂—CH₂O)₃]₂(MeO)Si(CH₂)₃]₂S_m,
[[C₁₈H₃₇—(CH₂—CH₂O)₄]₂(MeO)Si(CH₂)₃]₂S_m,
[[C₁₈H₃₇O—(CH₂—CH₂O)₅]₂(MeO)Si(CH₂)₃]₂S_m,
[[C₁₈H₃₇O—(CH₂—CH₂O)₆]₂(MeO)Si(CH₂)₃]₂S_m,
[[C₁₀H₂₁O—(CH₂—CH₂O)₂](EtO₂Si(CH₂)₃]₂S_m,
[[C₁₀H₂₁O—(CH₂—CH₂O)₃](EtO₂Si(CH₂)₃]₂S_m,
[[C₁₀H₂₁O—(CH₂—CH₂O)₄](EtO₂Si(CH₂)₃]₂S_m,
[[C₁₀H₂₁O—(CH₂—CH₂O)₅](EtO₂Si(CH₂)₃]₂S_m,
[[C₁₀H₂₁O—(CH₂—CH₂O)₆](EtO₂Si(CH₂)₃]₂S_m,
[[C₁₁H₂₃O—(CH₂—CH₂O)₂](EtO)₂Si(CH₂)₃]₂S_m,
[[C₁₁H₂₃O—(CH₂—CH₂O)₃](EtO)₂Si(CH₂)₃]₂S_m,
[[C₁₁H₂₃O—(CH₂—CH₂O)₄](EtO)₂Si(CH₂)₃]₂S_m,
[[C₁₁H₂₃O—(CH₂—CH₂O)₅](EtO)₂Si(CH₂)₃]₂S_m,
[[C₁₁H₂₃O—(CH₂—CH₂O)₄](EtO)₂Si(CH₂)₃]₂S_m,
[[C₁₂H₂₅O—(CH₂—CH₂O)₂](EtO)₂Si(CH₂)₃]₂S_m,
[[C₁₂H₂₅O—(CH₂—CH₂O)₃](EtO)₂Si(CH₂)₃]₂S_m,
[[C₁₂H₂₅O—(CH₂—CH₂O)₄](EtO)₂Si(CH₂)₃]₂S_m,
[[C₁₂H₂₅O—(CH₂—CH₂O)₅](EtO)₂Si(CH₂)₃]₂S_m,
[[C₁₂H₂₅O—(CH₂—CH₂O)₆](EtO)₂Si(CH₂)₃]₂S_m,
[[C₁₃H₂₇O—(CH₂—CH₂O)₂](EtO)₂Si(CH₂)₃]₂S_m,
[[C₁₃H₂₇O—(CH₂—CH₂O)₃](EtO)₂Si(CH₂)₃]₂S_m,
[[C₁₃H₂₇O—(CH₂—CH₂O)₄](EtO)₂Si(CH₂)₃]₂S_m,
[[C₁₃H₂₇O—(CH₂—CH₂O)₅](EtO)₂Si(CH₂)₃]₂S_m,
[[C₁₃H₂₇O—(CH₂—CH₂O)₆](EtO)₂Si(CH₂)₃]₂S_m,
[[C₁₄H₂₉O—(CH₂—CH₂O)₂](EtO₂Si(CH₂)₃]₂S_m,
[[C₁₄H₂₉O—(CH₂—CH₂O)₃](EtO)₂Si(CH₂)₃]₂S_m,
[[C₁₄H₂₉O—(CH₂—CH₂O)₄](EtO)₂Si(CH₂)₃]₂S_m,
[[C₁₄H₂₉O—(CH₂—CH₂O)₅](EtO)₂Si(CH₂)₃]₂S_m,
[[C₁₄H₂₉O—(CH₂—CH₂O)₆](EtO)₂Si(CH₂)₃]₂S_m,
[[C₁₆H₃₃O—(CH₂—CH₂O)₂](EtO)₂Si(CH₂)₃]₂S_m,
[[C₁₆H₃₃O—(CH₂—CH₂O)₃](EtO)₂Si(CH₂)₃]₂S_m,
[[C₁₆H₃₃O—(CH₂—CH₂O)₄](EtO)₂Si(CH₂)₃]₂S_m,
[[C₁₆H₃₃O—(CH₂—CH₂O)₅](EtO)₂Si(CH₂)₃]₂S_m,
[[C₁₆H₃₃O—(CH₂—CH₂O)₆](EtO)₂Si(CH₂)₃]₂S_m,
[[C₁₇H₃₅O—(CH₂—CH₂O)₂](EtO)₂Si(CH₂)₃]₂S_m,
[[C₁₇H₃₅O—(CH₂—CH₂O)₃](EtO)₂Si(CH₂)₃]₂S_m,
[[C₁₇H₃₅O—(CH₂—CH₂O)₄](EtO)₂Si(CH₂)₃]₂S_m,
[[C₁₇H₃₅O—(CH₂—CH₂O)₅](EtO)₂Si(CH₂)₃]₂S_m,
[[C₁₇H₃₅O—(CH₂—CH₂O)₆](EtO)₂Si(CH₂)₃]₂S_m,
[[C₁₈H₃₇O—(CH₂—CH₂O)₂](EtO)₂Si(CH₂)₃]₂S_m,
[[C₁₈H₃₇O—(CH₂—CH₂O)₃](EtO)₂Si(CH₂)₃]₂S_m,
[[C₁₈H₃₇O—(CH₂—CH₂O)₄](EtO)₂Si(CH₂)₃]₂S_m,
[[C₁₈H₃₇O—(CH₂—CH₂O)₅](EtO)₂Si(CH₂)₃]₂S_m,
[[C₁₈H₃₇O—(CH₂—CH₂O)₆](EtO)₂Si(CH₂)₃]₂S_m,
[[C₁₂H₂₅O—(CH₂—CH₂O)₂]₂(Et-O) Si (CH₂)₃]₂S_m,
[[C₁₂H₂₅O—(CH₂—CH₂O)₃]₂(EtO)Si(CH₂)₃]₂S_m,
[[C₁₂H₂₅O—(CH₂—CH₂O)₄]₂(EtO)Si(CH₂)₃]₂S_m,
[[C₁₂H₂₅O—(CH₂—CH₂O)₅]₂(EtO)Si(CH₂)₃]₂S_m,
[[C₁₂H₂₅O—(CH₂—CH₂O)₆]₂(EtO)Si(CH₂)₃]₂S_m,
[[C₁₃H₂₇O—(CH₂—CH₂O)₂]₂(EtO)Si(CH₂)₃]₂S_m,
[[C₁₃H₂₇O—(CH₂—CH₂O)₃]₂(EtO)Si(CH₂)₃]₂S_m,

[[C$_{13}$H$_{27}$O—(CH$_2$—CH$_2$O)$_4$]$_2$(EtO)Si(CH$_2$)$_3$]$_2$S$_m$,
[[C$_{13}$H$_{27}$—(CH$_2$—CH$_2$O)$_5$]$_2$ (EtO)Si(CH$_2$)$_3$]$_2$S$_m$,
[[C$_{13}$H$_{27}$O—(CH$_2$—CH$_2$O)$_6$]$_2$(EtO)Si(CH$_2$)$_3$]$_2$S$_m$,
[[C$_{14}$H$_{29}$O—(CH$_2$—CH$_2$O)$_2$]$_2$ (EtO)Si(CH$_2$)$_3$]$_2$S$_m$,
[[C$_{14}$H$_{29}$O—(CH$_2$—CH$_2$O)$_3$]$_2$(EtO)Si(CH$_2$)$_3$]$_2$S$_m$,
[[C$_{14}$H$_{29}$O—(CH$_2$—CH$_2$O)$_4$]$_2$(EtO)Si(CH$_2$)$_3$]$_2$S$_m$,
[[C$_{14}$H$_{29}$O—(CH$_2$—CH$_2$O)$_5$]$_2$(EtO)Si(CH$_2$)$_3$]$_2$S$_m$,
[[C$_{14}$H$_{29}$O—(CH$_2$—CH$_2$O)$_6$]$_2$(EtO)Si(CH$_2$)$_3$]$_2$S$_m$,
[[C$_{16}$H$_{33}$O—(CH$_2$—CH$_2$O)$_2$]$_2$(EtO)Si(CH$_2$)$_3$]$_2$S$_m$,
[[C$_{16}$H$_{33}$O—(CH$_2$—CH$_2$O)$_3$]$_2$(EtO)Si(CH$_2$)$_3$]$_2$S$_m$,
[[C$_{16}$H$_{33}$O—(CH$_2$—CH$_2$O)$_4$]$_2$(EtO)Si(CH$_2$)$_3$]$_2$S$_m$,
[[C$_{16}$H$_{33}$O—(CH$_2$—CH$_2$O)$_5$]$_2$(EtO)Si(CH$_2$)$_3$]$_2$S$_m$,
[[C$_{16}$H$_{33}$O—(CH$_2$—CH$_2$O)$_6$]$_2$(EtO)Si(CH$_2$)$_3$]$_2$S$_m$,
[[C$_{17}$H$_{35}$O—(CH$_2$—CH$_2$O)$_2$]$_2$(EtO)Si(CH$_2$)$_3$]$_2$S$_m$,
[[C$_{17}$H$_{35}$O—(CH$_2$—CH$_2$O)$_3$]$_2$(EtO)Si(CH$_2$)$_3$]$_2$S$_m$,
[[C$_{17}$H$_{35}$O—(CH$_2$—CH$_2$O)$_4$]$_2$(EtO)Si(CH$_2$)$_3$]$_2$S$_m$,
[[C$_{17}$H$_{35}$O—(CH$_2$—CH$_2$O)$_5$]$_2$(EtO)Si(CH$_2$)$_3$]$_2$S$_m$,
[[C$_{17}$H$_{35}$O—(CH$_2$—CH$_2$O)$_6$]$_2$ (EtO)Si(CH$_2$)$_3$]$_2$S$_m$,
[[C$_{18}$H$_{37}$O—(CH$_2$—CH$_2$O)$_2$]$_2$(EtO)Si(CH$_2$)$_3$]$_2$S$_m$,
[[C$_{18}$H$_{37}$O—(CH$_2$—CH$_2$O)$_3$]$_2$(EtO)Si(CH$_2$)$_3$]$_2$S$_m$,
[[C$_{18}$H$_{37}$O—(CH$_2$—CH$_2$O)$_4$]$_2$(EtO)Si(CH$_2$)$_3$]$_2$S$_m$,
[[C$_{18}$H$_{37}$O—(CH$_2$—CH$_2$O)$_5$]$_2$(EtO)Si(CH$_2$)$_3$]$_2$S$_m$,
[[C$_{18}$H$_{37}$O—(CH$_2$—CH$_2$O)$_6$]$_2$(EtO)Si(CH$_2$)$_3$]$_2$S$_m$,
[[C$_{10}$H$_{21}$O—(CH$_2$—CH$_2$O)$_2$]$_3$Si(CH$_2$)$_3$]$_2$S$_m$, [[C$_{10}$H$_{21}$O—(CH$_2$—CH$_2$O)$_3$]$_3$Si(CH$_2$)$_3$]$_2$S$_m$,
[[C$_{10}$H$_{21}$O—(CH$_2$—CH$_2$O)$_4$]$_3$Si(CH$_2$)$_3$]$_2$S$_m$, [[C$_{10}$H$_{21}$O—(CH$_2$—CH$_2$O)$_5$]$_3$Si(CH$_2$)$_3$]$_2$S$_m$, [[C$_{10}$H$_{21}$O—(CH$_2$—CH$_2$O)$_6$]$_3$Si(CH$_2$)$_3$]$_2$S$_m$,
[[C$_{12}$H$_{25}$O—(CH$_2$—CH$_2$O)$_2$]$_3$Si(CH$_2$)$_3$]$_2$S$_m$, [[C$_{12}$H$_{25}$O—(CH$_2$—CH$_2$O)$_3$]$_3$Si(CH$_2$)$_3$]$_2$S$_m$, [[C$_{12}$H$_{25}$O—(CH$_2$—CH$_2$O)$_4$]$_3$Si(CH$_2$)$_3$]$_2$S$_m$, [[C$_{12}$H$_{25}$O—(CH$_2$—CH$_2$O)$_5$]$_3$Si(CH$_2$)$_3$]$_2$S$_m$,
[[C$_{12}$H$_{25}$O—(CH$_2$—CH$_2$O)$_6$]$_3$Si(CH$_2$)$_3$]$_2$S$_m$,
[[C$_{13}$H$_{27}$O—(CH$_2$—CH$_2$O)$_2$]$_3$Si(CH$_2$)$_3$]$_2$S$_m$, [[C$_{13}$H$_{27}$O—(CH$_2$—CH$_2$O)$_3$]$_3$Si(CH$_2$)$_3$]$_2$S$_m$, [[C$_{13}$H$_{27}$O—(CH$_2$—CH$_2$O)$_4$]$_3$Si(CH$_2$)$_3$]$_2$S$_m$, [[C$_{13}$H$_{27}$O—(CH$_2$—CH$_2$O)$_5$]$_3$Si(CH$_2$)$_3$]$_2$S$_m$, [[C$_{13}$H$_{27}$O—(CH$_2$—CH$_2$O)$_6$]$_3$Si(CH$_2$)$_3$]$_2$S$_m$,
[[C$_{14}$H$_{29}$O—(CH$_2$—CH$_2$O)$_2$]$_3$Si(CH$_2$)$_3$]$_2$S$_m$, [[C$_{14}$H$_{29}$O—(CH$_2$—CH$_2$O)$_3$]$_3$Si(CH$_2$)$_3$]$_2$S$_m$, [[C$_{14}$H$_{29}$O—(CH$_2$—CH$_2$O)$_4$]$_3$Si(CH$_2$)$_3$]$_2$S$_m$, [[C$_{14}$H$_{29}$O—(CH$_2$—CH$_2$O)$_5$]$_3$Si(CH$_2$)$_3$]$_2$S$_m$, [[C$_{14}$H$_{29}$O—(CH$_2$—CH$_2$O)$_6$]$_3$Si(CH$_2$)$_3$]$_2$S$_m$;
[[C$_{15}$H$_{31}$O—(CH$_2$—CH$_2$O)$_2$]$_3$Si(CH$_2$)$_3$]$_2$S$_m$, [[C$_{15}$H$_{31}$O—(CH$_2$—CH$_2$O)$_3$]$_3$Si(CH$_2$)$_3$]$_2$S$_m$, [[C$_{15}$H$_{31}$O—(CH$_2$—CH$_2$O)$_4$]$_3$Si(CH$_2$)$_3$]$_2$S$_m$, [[C$_{15}$H$_{31}$O—(CH$_2$—CH$_2$O)$_5$]$_3$Si(CH$_2$)$_3$]$_2$S$_m$, [[C$_{15}$H$_{31}$O—(CH$_2$—CH$_2$O)$_6$]$_3$Si(CH$_2$)$_3$]$_2$S$_m$,
[[C$_{16}$H$_{33}$O—(CH$_2$—CH$_2$O)$_2$]$_3$Si(CH$_2$)$_3$]$_2$S$_m$, [[C$_{16}$H$_{33}$O—(CH$_2$—CH$_2$O)$_3$]$_3$Si(CH$_2$)$_3$]$_2$S$_m$, [[C$_{16}$H$_{33}$O—(CH$_2$—CH$_2$O)$_4$]$_3$Si(CH$_2$)$_3$]$_2$S$_m$, [[C$_{16}$H$_{33}$O—(CH$_2$—CH$_2$O)$_5$]$_3$Si(CH$_2$)$_3$]$_2$S$_m$, [[C$_{16}$H$_{33}$O—(CH$_2$—CH$_2$O)$_6$]$_3$Si(CH$_2$)$_3$]$_2$S$_m$,
[[C$_{18}$H$_{37}$O—(CH$_2$—CH$_2$O)$_2$]$_3$Si(CH$_2$)$_3$]$_2$S$_m$, [[C$_{18}$H$_{37}$O—(CH$_2$—CH$_2$O)$_3$]$_3$Si(CH$_2$)$_3$]$_2$S$_m$, [[C$_{18}$H$_{37}$O—(CH$_2$—CH$_2$O)$_4$]$_3$Si(CH$_2$)$_3$]$_2$S$_m$, [[C$_{18}$H$_{37}$O—(CH$_2$—CH$_2$O)$_5$]$_3$Si(CH$_2$)$_3$]$_2$S$_m$, or [[C$_{18}$H$_{37}$O—(CH$_2$—CH$_2$O)$_6$]$_3$Si(CH$_2$)$_3$]$_2$S$_m$, where the alkyl moieties can be unbranched or branched.

Compounds of the formula IV, where Alk =C$_3$H$_7$, C$_4$H$_9$, C$_5$H$_{11}$, C$_6$H$_{13}$, C$_7$H$_{15}$, C$_8$H$_{17}$, C$_9$H$_{19}$, C$_{10}$H$_{21}$, C$_{11}$H$_{23}$, C$_{12}$H$_{25}$, C$_{13}$H$_{27}$, C$_{14}$H$_{29}$, C$_{15}$H$_{31}$, C$_{16}$H$_{33}$, C$_{17}$H$_{35}$, or C$_{19}$H$_{37}$ can be:

[[Alk-O—(CH$_2$—CH(CH$_3$)O—)$_2$](MeO)$_2$Si(CH$_2$)$_3$]$_2$S$_m$,
[[Alk-O—(CH$_2$—CH(CH$_3$)O—)$_3$](MeO)$_2$Si(CH$_2$)$_3$]$_2$S$_m$,
[[Alk-O—(CH$_2$—CH(CH$_3$)O—)$_4$](MeO)$_2$Si(CH$_2$)$_3$]$_2$S$_m$,
[[Alk-O—(CH$_2$—CH(CH$_3$)O—)$_5$](MeO)$_2$Si(CH$_2$)$_3$]$_2$S$_m$,
[[Alk-O—(CH$_2$—CH(CH$_3$)O—)$_6$](MeO)$_2$Si(CH$_2$)$_3$]$_2$S$_m$,
[[Alk-O—(CH$_2$—CH(CH$_3$)O—)$_2$]$_2$(MeO)$_2$Si(CH$_2$)$_3$]$_2$S$_m$,
[[Alk-O—(CH$_2$—CH(CH$_3$)O—)$_3$]$_2$ (MeO)Si(CH$_2$)$_3$]$_2$S$_m$,
[[Alk-O—(CH$_2$—CH(CH$_3$)O—)$_4$]$_2$(MeO)Si(CH$_2$)$_3$]$_2$S$_m$,
[[Alk-O—(CH$_2$—CH(CH$_3$)O—)$_5$]$_2$(MeO)Si(CH$_2$)$_3$]$_2$S$_m$,
[[Alk-O—(CH$_2$—CH(CH$_3$)O—)$_6$]$_2$(MeO)Si(CH$_2$)$_3$]$_2$S$_m$,
[[Alk-O—(CH$_2$—CH(CH$_3$)O—)$_2$](Me)(MeO)Si(CH$_2$)$_3$]$_2$S$_m$, [[Alk-O—(CH$_2$—CH(CH$_3$)O—)$_3$](Me)(MeO)Si (CH$_2$)$_3$]$_2$S$_m$, [[Alk-O—(CH$_2$—CH(CH$_3$)O—)$_4$](Me)(MeO) Si(CH$_2$)$_3$]$_2$S$_m$, [[Alk-O—(CH$_2$—CH(CH$_3$)O—)$_5$](Me) (MeO)Si(CH$_2$)$_3$]$_2$S$_m$, [[Alk-O—(CH$_2$—CH(CH$_3$)O—)$_6$] (Me)(MeO)Si(CH$_2$)$_3$]$_2$S$_m$,
[[Alk-O—(CH$_2$—CH(CH$_3$)$_2$](EtO)$_2$Si (CH$_2$)$_3$]$_2$S$_m$, [[Alk-O—(CH$_2$—CH(CH$_3$)O—)$_3$](EtO)$_2$Si(CH$_2$)$_3$]$_2$S$_m$, [[Alk-O—(CH$_2$—CH(CH$_3$)O—)$_4$](EtO)$_2$Si(CH$_2$)$_3$]$_2$S$_m$, [[Alk-O—(CH$_2$—CH(CH$_3$)O—)$_5$](EtO)$_2$Si (CH$_2$)$_3$]$_2$S$_m$, [[Alk-O—(CH$_2$—CH(CH$_3$)O—)$_6$](EtO)$_2$Si(CH$_2$)$_3$]$_2$S$_m$,
[[Alk-O—(CH$_2$—CH(CH$_3$)O—)$_2$]$_2$(EtO)Si(CH$_2$)$_3$]$_2$S$_m$,
[[Alk-O—(CH$_2$—CH(CH$_3$)O—)$_3$]$_2$(EtO)Si(CH$_2$)$_3$]$_2$S$_m$,
[[Alk-O—(CH$_2$—CH(CH$_3$)O—)$_4$]$_2$(EtO)Si(CH$_2$)$_3$]$_2$S$_m$,
[[Alk-O—(CH$_2$—CH(CH$_3$)O—)$_5$]$_2$(EtO)Si(CH$_2$)$_3$]$_2$S$_m$,
[[Alk-O—(CH$_2$—CH(CH$_3$)O—)$_6$]$_2$(EtO)Si(CH$_2$)$_3$]$_2$S$_m$,
[[Alk-O—(CH$_2$—CH(CH$_3$)O—)$_2$](Me)(EtO)Si(CH$_2$)$_3$]$_2$S$_m$,
[[Alk-O—(CH$_2$—CH(CH$_3$)O—)$_3$](Me)(EtO)Si(CH$_2$)$_3$]$_2$S$_m$,
[[Alk-O—(CH$_2$—CH(CH$_3$)O—)$_4$](Me)(EtO)Si(CH$_2$)$_3$]$_2$S$_m$,
[[Alk-O—(CH$_2$—CH(CH$_3$)O—)$_5$](Me)(EtO)Si(CH$_2$)$_3$]$_2$S$_m$,
[[Alk-O—(CH$_2$—CH(CH$_3$)O—)$_6$](Me)(EtO)Si(CH$_2$)$_3$]$_2$S$_m$,
[[Alk-O—(CH$_2$—CH(CH$_3$)O—)$_2$]$_2$(Me)Si(CH$_2$)$_3$]$_2$S$_m$,
[[Alk-O—(CH$_2$—CH(CH$_3$)O—)$_3$]$_2$(Me)Si(CH$_2$)$_3$]$_2$S$_m$,
[[Alk-O—(CH$_2$—CH(CH$_3$)O—)$_4$]$_2$(Me)Si(CH$_2$)$_3$]$_2$S$_m$,
[[Alk-O—(CH$_2$—CH(CH$_3$)O—)$_5$]$_2$(Me)Si(CH$_2$)$_3$]$_2$S$_m$,
[[Alk-O—(CH$_2$—CH(CH$_3$)O—)$_6$]$_2$(Me)Si(CH$_2$)$_3$]$_2$S$_m$,
[[Alk-O—(CH$_2$—CH(CH$_3$)O—)$_2$](Me)$_2$Si(CH$_2$)$_3$]$_2$S$_m$,
[[Alk-O—(CH$_2$—CH(CH$_3$)O—)$_3$](Me)$_2$Si(CH$_2$)$_3$]$_2$S$_m$,
[[Alk-O—(CH$_2$—CH(CH$_3$)O—)$_4$](Me)$_2$Si(CH$_2$)$_3$]$_2$S$_m$,
[[Alk-O—(CH$_2$—CH(CH$_3$)O—)$_5$](Me)$_2$Si(CH$_2$)$_3$]$_2$S$_m$, or
[[Alk-O—(CH$_2$—CH(CH$_3$)O—)$_6$](Me)$_2$Si(CH$_2$)$_3$]$_2$S$_m$,
where the Alk groups can be unbranched or branched.

Alkylpolyether alcohols of the formula V can be used either in the form of a mixture of various alcohols or else in the form of pure substances. Examples of alkylpolyether alcohols HO—((CR$^H_2$)$_w$—O—)$_v$Alk that can be used are branched or linear alcohols that have been ethoxylated/propoxylated or, respectively, that contain ethylene oxide units and/or propylene oxide units.

The alkylpolyether alcohols used can be hydrocarbon-terminated polyethylene glycol, Alk'-O—(CH$_2$—CH$_2$—O)$_{yI}$—H or alk'-(CH$_2$—CH$_2$—O)$_{yI}$-Alk',
hydrocarbon-terminated polypropylene glycol Alk'-O—(CH$_2$—CH(CH$_3$)—O)$_{yI}$—H or Alk'-O—(CH$_2$—CH(CH$_3$)—O)$_{yI}$-Alk',
hydrocarbon-terminated polybutylene glycol Alk'-O—(CH$_2$—CH$_2$—CH$_2$—CH$_2$—O)$_{yI}$—H, Alk'-O—(CH$_2$—CH(CH$_3$)—CH$_2$—O)$_{yI}$—H, Alk'-O—(CH$_2$—CH$_2$—CH$_2$—CH$_2$—O)$_{yI}$-Alk', or Alk'-O—(CH$_2$—CH(CH$_3$)—CH$_2$—O)$_{yI}$-Alk',
where the average of y$^I$ is from 2 to 25, preferably from 2 to 15, particularly preferably from 3 to 8 and from 10 to 14, very particularly preferably from 3 to 6 and from 10 to 13, and Alk' is a branched or unbranched, saturated or unsaturated, substituted or unsubstituted, aliphatic, aromatic, or mixed aliphatic/aromatic monovalent C$_1$-C$_{35}$—, preferably C$_2$-C$_{22}$—, particularly preferably C$_3$-C$_{18}$—, very particularly preferably C$_4$-C$_{13}$—, extremely preferably C$_6$-C$_{10}$—, hydrocarbon group.

The unit O—(CR$^H_2$—CR$^H_2$—O)$_{yI}$ present in the alkylpolyether alcohols of the type HO—(CR$^H_2$—CR$^H_2$—O)$_{yI}$-Alk' can preferably be:
O—(—CH$_2$—CH$_2$—O—)$_a$,
O—(—CH(CH$_3$)—CH$_2$—O—)$_a$,
O—(—CH$_2$—CH(CH$_3$)—O—)$_a$, O—(—CH$_2$—CH$_2$—O—)$_a$(—CH(CH$_3$)—CH$_2$—O—),
O—(—CH$_2$—CH$_2$—O—)(—CH(CH$_3$)—CH$_2$—O—)$_a$,
O—(—CH$_2$—CH$_2$—O—)$_a$(—CH$_2$—CH(CH$_3$)—O—),
O—(—CH$_2$—CH$_2$—O—)(—CH$_2$—CH(CH$_3$)—O—)$_a$,
O—(—CH(CH$_3$)—CH$_2$—O—)$_a$(—CH$_2$—CH(CH$_3$)—O—),
O—(—CH(CH$_3$)—CH$_2$—O—)(—CH$_2$—CH(CH$_3$)—O—)$_a$,
O—(—CH$_2$—CH$_2$—O—)$_a$(—CH(CH$_3$)—CH$_2$—O—)$_b$(—CH$_2$—CH(CH$_3$)—O—)$_c$, or a mutual combination, where a+b+c=y$^l$.

The indices a, b, and c are whole numbers, and designate the number of repeat units.

The alkylpolyether alcohols of the general formula V can preferably be:
HO—(CH$_2$—CH$_2$O)$_2$—C$_3$H$_7$, HO—(CH$_2$—CH$_2$O)$_3$—C$_3$H$_7$, HO—(CH$_2$—CH$_2$O)$_4$—C$_3$H$_7$, HO—(CH$_2$—CH$_2$O)$_5$—C$_3$H$_7$, HO—(CH$_2$—CH$_2$O)$_6$—C$_3$H$_7$, HO—(CH$_2$—CH$_2$O)$_7$—C$_3$H$_7$, HO—(CH(CH$_3$)—CH$_2$O)$_2$—C$_3$H$_7$, HO—(CH(CH$_3$)—CH$_2$O)$_3$—C$_3$H$_7$, HO—(CH(CH$_3$)—CH$_2$O)$_4$—C$_3$H$_7$, HO—(CH(CH$_3$)—CH$_2$O)$_5$—C$_3$H$_7$, HO—(CH(CH$_3$)—CH$_2$O)$_6$—C$_3$H$_7$, HO—(CH(CH$_3$)—CH$_2$O)$_7$—C$_3$H$_7$,
HO—(CH$_2$—CH$_2$O)$_2$—C$_4$H$_9$, HO—(CH$_2$—CH$_2$O)$_3$—C$_4$H$_9$, HO—(CH$_2$—CH$_2$O)$_4$—C$_4$H$_9$, HO—(CH$_2$—CH$_2$O)$_5$—C$_4$H$_9$, HO—(CH$_2$—CH$_2$O)$_6$—C$_4$H$_9$, HO—(CH$_2$—CH$_2$O)$_7$—C$_4$H$_9$, HO—(CH(CH$_3$)—CH$_2$O)$_2$—C$_4$H$_9$, HO—(CH(CH$_3$)—CH$_2$O)$_3$—C$_4$H$_9$, HO—(CH(CH$_3$)—CH$_2$O)$_4$—C$_4$H$_9$, HO—(CH(CH$_3$)—CH$_2$O)$_5$—C$_4$H$_9$, HO—(CH(CH$_3$)—CH$_2$O)$_6$—C$_4$H$_9$, HO—(CH(CH$_3$)—CH$_2$O)$_7$—C$_4$H$_9$,
HO—(CH$_2$—CH$_2$O)$_2$C$_5$H$_{11}$, HO—(CH$_2$—CH$_2$O)$_3$—C$_5$H$_{11}$, HO—(CH$_2$—CH$_2$O)$_4$—C$_5$H$_{11}$, HO—(CH$_2$—CH$_2$O)$_5$C$_5$H$_{11}$, HO—(CH$_2$—CH$_2$O)$_6$C$_5$H$_{11}$, HO—(CH$_2$—CH$_2$O)$_7$—C$_5$H$_{11}$, HO—(CH(CH$_3$)—CH$_2$O)$_2$—C$_5$H$_{11}$, HO—(CH(CH$_3$)—CH$_2$O)$_3$—C$_5$H$_{11}$, HO—(CH(CH$_3$)—CH$_2$O)$_4$—C$_5$H$_{11}$, HO—(CH(CH$_3$)—CH$_2$O)$_5$—C$_5$H$_{11}$, HO—(CH(CH$_3$)—CH$_2$O)$_6$—C$_5$H$_{11}$, HO—(CH(CH$_3$)—CH$_2$O)$_7$—C$_5$H$_{11}$,
HO—(CH$_2$—CH$_2$O)$_2$—C$_6$H$_{13}$, HO—(CH$_2$—CH$_2$O)$_3$—C$_6$H$_{13}$, HO—(CH$_2$—CH$_2$O)$_4$—C$_6$H$_{13}$, HO—(CH$_2$—CH$_2$O)$_5$—C$_6$H$_{13}$, HO—(CH$_2$—CH$_2$O)$_6$—C$_6$H$_{13}$, HO—(CH$_2$—CH$_2$O)$_7$—C$_6$H$_{13}$, HO—(CH(CH$_3$)—CH$_2$O)$_2$—C$_6$H$_{13}$, HO—(CH(CH$_3$)—CH$_2$O)$_3$—C$_6$H$_{13}$, HO—(CH(CH$_3$)—CH$_2$O)$_4$—C$_6$H$_{13}$, HO—(CH(CH$_3$)—CH$_2$O)$_5$—C$_6$H$_{13}$, HO—(CH(CH$_3$)—CH$_2$O)$_6$—C$_6$H$_{13}$, HO—(CH(CH$_3$)—CH$_2$O)$_7$—C$_6$H$_{13}$,
HO—(CH$_2$—CH$_2$O)$_2$—C$_7$H$_{15}$, HO—(CH$_2$—CH$_2$O)$_3$—C$_7$H$_{15}$, HO—(CH$_2$—CH$_2$O)$_4$—C$_7$H$_{15}$, HO—(CH$_2$—CH$_2$O)$_5$—C$_7$H$_{15}$, HO—(CH$_2$—CH$_2$O)$_6$—C$_7$H$_{15}$, HO—(CH$_2$—CH$_2$O)—C$_7$H$_{15}$, HO—(CH(CH$_3$)—CH$_2$O)$_2$—C$_7$H$_{15}$, HO—(CH(CH$_3$)—CH$_2$O)$_3$—C$_7$H$_{15}$, HO—(CH(CH$_3$)—CH$_2$O)$_4$—C$_7$H$_{15}$, HO—(CH(CH$_3$)—CH$_2$O)$_5$—C$_7$H$_{15}$, HO—(CH(CH$_3$)—CH$_2$O)$_6$—C$_7$H$_{15}$, HO—(CH(CH$_3$)—CH$_2$O)$_7$—C$_7$H$_{15}$,
HO—(CH$_2$—CH$_2$O)$_2$—C$_8$H$_{17}$, HO—(CH$_2$—CH$_2$O)$_3$—C$_8$H$_{17}$, HO—(CH$_2$—CH$_2$O)$_4$—C$_8$H$_{17}$, HO—(CH$_2$—CH$_2$O)$_5$—C$_8$H$_{17}$, HO—(CH$_2$—CH$_2$O)$_6$—C$_8$H$_{17}$, HO—(CH$_2$—CH$_2$O)$_7$—C$_8$H$_{17}$, HO—(CH(CH$_3$)—CH$_2$O)$_2$—C$_8$H$_{17}$, HO—(CH(CH$_3$)—CH$_2$O)$_3$—C$_8$H$_{17}$, HO—(CH(CH$_3$)—CH$_2$O)$_4$—C$_8$H$_{17}$, HO—(CH(CH$_3$)—CH$_2$O)$_5$—C$_8$H$_{17}$, HO—(CH(CH$_3$)—CH$_2$O)$_6$—C$_8$H$_{17}$, HO—(CH(CH$_3$)—CH$_2$O)$_7$—C$_8$H$_{17}$,
HO—(CH$_2$—CH$_2$O)$_2$—C$_9$H$_{19}$, HO—(CH$_2$—CH$_2$O)$_3$—C$_9$H$_{19}$, HO—(CH$_2$—CH$_2$O)$_4$—C$_9$H$_{19}$, HO—(CH$_2$—CH$_2$O)$_5$—C$_9$H$_{19}$, HO—(CH$_2$—CH$_2$O)$_6$—C$_9$H$_{19}$, HO—(CH$_2$—CH$_2$O)$_7$—C$_9$H$_{19}$, HO—(CH(CH$_3$)—CH$_2$O)$_2$—C$_9$H$_{19}$, HO—(CH(CH$_3$)—CH$_2$O)$_3$—C$_9$H$_{19}$, HO—(CH(CH$_3$)—CH$_2$O)$_4$—C$_9$H$_{19}$, HO—(CH(CH$_3$)—CH$_2$O)$_5$—C$_9$H$_{19}$, HO—(CH(CH$_3$)—CH$_2$O)$_6$—C$_9$H$_{19}$, HO—(CH(CH$_3$)—CH$_2$O)$_7$—C$_9$H$_{19}$,
HO—(CH$_2$—CH$_2$O)$_2$—C$_{10}$H$_{21}$, HO—(CH$_2$—CH$_2$O)$_3$—C$_{10}$H$_{21}$, HO—(CH$_2$—CH$_2$O)$_4$—C$_{10}$H$_{21}$, HO—(CH$_2$—CH$_2$O)$_5$—C$_{10}$H$_{21}$, HO—(CH$_2$—CH$_2$O)$_6$—C$_{10}$H$_{21}$, HO—(CH$_2$CH$_2$O)$_7$—C$_{10}$H$_{21}$,
HO—(CH(CH$_3$)—CH$_2$O)$_2$—C$_{10}$H$_{21}$, HO—(CH(CH$_3$)—CH$_2$O)$_3$—C$_{10}$H$_{21}$, HO—(CH(CH$_3$)—CH$_2$O)$_4$—C$_{10}$H$_{21}$, HO—(CH(CH$_3$)—CH$_2$O)$_5$—C$_{10}$H$_{21}$, HO—(CH(CH$_3$)—CH$_2$O)$_6$—C$_{10}$H$_{21}$, HO—(CH(CH$_3$)—CH$_2$O)$_7$—C$_{10}$H$_{21}$,
HO—(CH$_2$—CH$_2$O)$_2$—C$_{11}$H$_{23}$, HO—(CH$_2$—CH$_2$O)$_3$—C$_{11}$H$_{23}$, HO—(CH$_2$—CH$_2$O)$_4$—C$_{11}$H$_{23}$, HO—(CH$_2$—CH$_2$O)$_5$—C$_{11}$H$_{23}$, HO—(CH$_2$—CH$_2$O)$_6$—C$_{11}$H$_{23}$, HO—(CH$_2$—CH$_2$O)$_7$—C$_{11}$H$_{23}$,
HO—(CH(CH$_3$)—CH$_2$O)$_2$—C$_{11}$H$_{23}$, HO—(CH(CH$_3$)—CH$_2$O)$_3$—C$_{11}$H$_{23}$, HO—(CH(CH$_3$)—CH$_2$O)$_4$—C$_{11}$H$_{23}$, HO—(CH(CH$_3$)—CH$_2$O)$_5$—C$_{11}$H$_{23}$, HO—(CH(CH$_3$)—CH$_2$O)$_6$—C$_{11}$H$_{23}$, HO—(CH(CH$_3$)—CH$_2$O)$_7$—C$_{11}$H$_{23}$,
HO—(CH$_2$—CH$_2$O)$_2$—C$_{12}$H$_{25}$, HO—(CH$_2$—CH$_2$O)$_3$—C$_{12}$H$_{25}$, HO—(CH$_2$—CH$_2$O)$_4$—C$_{12}$H$_{25}$, HO—(CH$_2$—CH$_2$O)$_5$—C$_{12}$H$_{25}$, HO—(CH$_2$—CH$_2$O)$_6$—C$_{12}$H$_{25}$, HO—(CH$_2$—CH$_2$O)$_7$—C$_{12}$H$_{25}$,
HO—(CH(CH$_3$)—CH$_2$O)$_2$—C$_{12}$H$_{25}$, HO—(CH(CH$_3$)—CH$_2$O)$_3$—C$_{12}$H$_{25}$, HO—(CH(CH$_3$)—CH$_2$O)$_4$—C$_{12}$H$_{25}$, HO—(CH(CH$_3$)—CH$_2$O)$_5$—C$_{12}$H$_{25}$, HO—(CH(CH$_3$)—CH$_2$O)$_6$—C$_{12}$H$_{25}$, HO—(CH(CH$_3$)—CH$_2$O)$_7$—C$_{12}$H$_{25}$,
HO—(CH$_2$—CH$_2$O)$_2$—C$_{13}$H$_{27}$, HO—(CH$_2$—CH$_2$O)$_3$—C$_{13}$H$_{27}$, HO—(CH$_2$—CH$_2$O)$_4$—C$_{13}$H$_{27}$, HO—(CH$_2$—CH$_2$O)$_5$—C$_{13}$H$_{27}$, HO—(CH$_2$—CH$_2$O)$_6$—C$_{13}$H$_{27}$, HO—(CH$_2$—CH$_2$O)$_7$—C$_{13}$H$_{27}$,
HO—(CH(CH$_3$)—CH$_2$O)$_2$—C$_{13}$H$_{27}$, HO—(CH(CH$_3$)—CH$_2$O)$_3$—C$_{13}$H$_{27}$, HO—(CH(CH$_3$)—CH$_2$O)$_4$—C$_{13}$H$_{27}$, HO—(CH(CH$_3$)—CH$_2$O)$_5$—C$_{13}$H$_{27}$, HO—(CH(CH$_3$)—CH$_2$O)$_6$—C$_{13}$H$_{27}$, HO—(CH(CH$_3$)—CH$_2$O)$_7$—C$_{13}$H$_{27}$,
HO—(CH$_2$—CH$_2$O)$_2$—C$_{14}$H$_{29}$, HO—(CH$_2$—CH$_2$O)$_3$—C$_{14}$H$_{29}$, HO—(CH$_2$—CH$_2$O)$_4$—C$_{14}$H$_{29}$, HO—(CH$_2$—CH$_2$O)$_5$—C$_{14}$H$_{29}$, HO—(CH$_2$—CH$_2$O)$_6$—C$_{14}$H$_{29}$, HO—(CH$_2$—CH$_2$O)$_7$—C$_{14}$H$_{29}$,
HO—(CH(CH$_3$)—CH$_2$O)$_2$—C$_{14}$H$_{29}$, HO—(CH(CH$_3$)—CH$_2$O)$_3$—C$_{14}$H$_{29}$, HO—(CH(CH$_3$)—CH$_2$O)$_4$—C$_{14}$H$_{29}$, HO—(CH(CH$_3$)—CH$_2$O)$_5$—C$_{14}$H$_{29}$, HO—(CH(CH$_3$)—CH$_2$O)$_6$—C$_{14}$H$_{29}$, HO—(CH(CH$_3$)—CH$_2$O)$_7$—C$_{14}$H$_{29}$,
HO—(CH$_2$—CH$_2$O)$_2$—C$_{15}$H$_{31}$, HO—(CH$_2$—CH$_2$O)$_3$—C$_{15}$H$_{31}$, HO—(CH$_2$—CH$_2$O)$_4$—C$_{15}$H$_{31}$, HO—(CH$_2$—CH$_2$O)$_5$—C$_{15}$H$_{31}$, HO—(CH$_2$—CH$_2$O)$_6$—C$_{15}$H$_{31}$, HO—(CH$_2$—CH$_2$O)$_7$—C$_{15}$H$_{31}$,
HO—(CH(CH$_3$)—CH$_2$O)$_2$—C$_{15}$H$_{31}$, HO—(CH(CH$_3$)—CH$_2$O)$_3$—C$_{15}$H$_{31}$, HO—(CH(CH$_3$)—CH$_2$O)$_4$—C$_{15}$H$_{31}$, HO—(CH(CH$_3$)—CH$_2$O)$_5$—C$_{15}$H$_{31}$, HO—(CH(CH$_3$)—CH$_2$O)$_6$—C$_{15}$H$_{31}$, HO—(CH(CH$_3$)—CH$_2$O)$_7$—C$_{15}$H$_{31}$,
HO—(CH$_2$—CH$_2$O)$_2$—C$_{16}$H$_{33}$, HO—(CH$_2$—CH$_2$O)$_3$—C$_{16}$H$_{33}$, HO—(CH$_2$—CH$_2$O)$_4$—C$_{16}$H$_{33}$, HO—(CH$_2$—CH$_2$O)$_5$—C$_{16}$H$_{33}$, HO—(CH$_2$—CH$_2$O)$_6$—C$_{16}$H$_{33}$, HO—(CH(CH$_3$)—CH$_2$O)$_2$—C$_{16}$H$_{33}$, HO—(CH(CH$_3$)—CH$_2$O)$_3$—C$_{16}$H$_{33}$, HO—(CH(CH$_3$)—CH$_2$O)$_4$—C$_{16}$H$_{33}$, HO—(CH(CH$_3$)—CH$_2$O)$_5$—C$_{16}$H$_{33}$, HO—(CH(CH$_3$)—CH$_2$O)$_6$—C$_{16}$H$_{33}$,
HO—(CH$_2$—CH$_2$O)$_2$—C$_{17}$H$_{35}$, HO—(CH$_2$—CH$_2$O)$_3$—C$_{17}$H$_{35}$, HO—(CH$_2$—CH$_2$O)$_4$—C$_{17}$H$_{35}$, HO—(CH$_2$—CH$_2$O)$_5$—C$_{17}$H$_{35}$ f HO—(CH$_2$—CH$_2$O)$_6$—C$_{17}$H$_{35}$, HO—(CH$_2$—CH$_2$O)$_7$—C$_{17}$H$_{35}$,
HO—(CH(CH$_3$)—CH$_2$O)$_2$—C$_{17}$H$_{35}$, HO—(CH(CH$_3$)—CH$_2$O)$_3$—C$_{17}$H$_{35}$, HO—(CH(CH$_3$)—CH$_2$O)$_4$—C$_{17}$H$_{35}$, HO—(CH(CH$_3$)—CH$_2$O)$_5$—C$_{17}$H$_{35}$, HO—(CH(CH$_3$)—CH$_2$O)$_6$—C$_{17}$H$_{35}$, HO—(CH(CH$_3$)—CH$_2$O)$_7$—C$_{17}$H$_{35}$, HO—(CH$_2$—CH$_2$O)$_2$—C$_{18}$H$_{37}$, HO—(CH$_2$—CH$_2$O)$_3$—C$_{18}$H$_{37}$, HO—(CH$_2$—CH$_2$O)$_4$—C$_{18}$H$_{37}$, HO—(CH$_2$—CH$_2$O)$_5$—C$_{18}$H$_{37}$,
HO—(CH(CH$_3$)—CH$_2$O)$_2$—C$_{18}$H$_{37}$, HO—(CH(CH$_3$)—CH$_2$O)$_3$—C$_{18}$H$_{37}$, HO—(CH(CH$_3$)—CH$_2$O)$_4$—C$_{18}$H$_{37}$, HO—(CH(CH$_3$)—CH$_2$O)$_5$—C$_{18}$H$_{37}$, HO—(CH(CH$_3$)—CH$_2$O)$_6$—C$_{18}$H$_{37}$, HO—(CH(CH$_3$)—CH$_2$O)$_7$—C$_{18}$H$_{37}$,
HO—(CH$_2$—CH$_2$O)$_2$—C$_6$H$_4$—C$_9$H$_{19}$, HO—(CH$_2$—CH$_2$O)$_3$—C$_6$H$_4$—C$_9$H$_{19}$, HO—(CH$_2$—CH$_2$O)$_4$—C$_6$H$_4$—C$_9$H$_{19}$, HO—(CH$_2$—CH$_2$O)$_5$—C$_6$H$_4$—C$_9$H$_{19}$, HO—(CH$_2$—CH$_2$O)$_6$—C$_6$H$_4$—C$_9$H$_{19}$, HO—(CH$_2$—CH$_2$O)$_7$—C$_6$H$_4$—C$_9$H$_{19}$,
HO—(CH(CH$_3$)—CH$_2$O)$_2$—C$_6$H$_4$—C$_9$H$_{19}$, HO—(CH(CH$_3$)—CH$_2$O)$_3$—C$_6$H$_4$—C$_9$H$_{19}$, HO—(CH(CH$_3$)—CH$_2$O)$_4$—C$_6$H$_4$—C$_9$H$_{19}$, HO—(CH(CH$_3$)—CH$_2$O)$_5$—C$_6$H$_4$—C$_9$H$_{19}$, HO—(CH(CH$_3$)—CH$_2$O)$_6$—C$_6$H$_4$—C$_9$H$_{19}$, or HO—(CH(CH$_3$)—CH$_2$O)$_7$—C$_6$H$_4$—C$_9$H$_{19}$.

The polysulfidic organo(alkylpolyethersilanes) of the general formula III and IV can be mixtures composed of polysulfidic organo(alkylpolyethersilanes) of the general formula III and IV.

The polysulfidic organo(alkylpolyethersilanes) of the general formulae III and IV can be mixtures composed of polysulfidic organo(alkylpolyethersilanes) of the general formulae III and IV, which have different X, if appropriate having different v and/or w.

The polysulfidic organo(alkylpolyethersilanes) of the general formulae IV can be a mixture composed of polysulfidic organo(alkylpolyethersilanes) of the general formulae IV in which Alk has a different number of carbon atoms and/or has branching.

The polysulfidic organo(alkylpolyethersilanes) of the general formula IV can be a mixture composed of polysulfidic organo(alkylpolyethersilanes) of the general formula IV where the mixture comprises more than 50 mol %, preferably more than 70 mol %, particularly preferably more than 85 mol %, very particularly preferably more than 95 mol %, of compounds having S$_2$.

The amount present of the polysulfidic organo(alkylpolyethersilanes) having S$_1$ can be from 0.01 to 20 mol %, preferably from 0.1 to 15 mol %, particularly preferably from 0.1 to 10 mol %, very particularly preferably from 2 to 8 mol %, based on the polysulfidic organo(alkylpolyethersilanes) of the general formulae III and IV present in the mixture of the invention.

The mixtures of the invention, composed of silicon-containing coupling reagents comprising (mercaptoorganyl)alkylpolyethersilanes containing silanol groups and (mercaptoorganyl)alkylpolyethersilanes free from silanol groups in ratios by weight of from 5:95 to 95:5 can readily be used to form condensation products, i.e. oligo- and polysiloxanes, by water addition and, if appropriate, additive addition, with hydrolysis or water cleavage.

These oligomeric or polymeric siloxanes derived from the mixtures of the invention composed of silicon-containing coupling reagents can be used as coupling reagents for applications identical with those for the uncondensed mixtures of the invention, composed of silicon-containing coupling reagents.

The mixtures of the invention, composed of silicon-containing coupling reagents, can be separated by means of HPLC techniques and/or GPC techniques.

The mixtures of the invention, composed of silicon-containing coupling reagents, can be described analytically by means of high-resolution $^1$H NMR, $^{29}$Si NMR, $^{13}$C NMR, HPLC, GPC, and/or high-resolution mass spectrometry, in the form of a mixture or after separation into individual fractions or constituents.

The mixtures of the invention, composed of silicon-containing coupling reagents, can preferably be described analytically by means of high-resolution $^{13}$C NMR, in the form of a mixture or after separation into individual fractions or constituents.

The mixtures of the invention, composed of silicon-containing coupling reagents, can be separated by HPLC into their individual constituents and analyzed.

The mixtures of the invention, composed of silicon-containing coupling reagents, can be separated into individual fractions or constituents by GPC, and then described analytically.

The mixtures of the invention, composed of silicon-containing coupling reagents, can be analyzed with respect to their individual constituents by high-resolution mass spectrometry.

The overall composition of the mixtures of the invention, composed of silicon-containing coupling reagents, can be determined by means of $^{13}$C and $^{29}$Si nuclear resonance spectroscopy, by virtue of the relative distribution of the alkoxy substituents with respect to one another.

The composition of the resultant substance mixtures in relation to the relative distribution of the alkoxy substituents with respect to one another can be determined by total hydrolysis of the alkoxysilanes and subsequent chromatographic analysis.

The mixtures of the invention, composed of silicon-containing coupling reagents, can be obtainable as follows:

(1) Physical mixing of the individual constituents or of groups of the constituents to give the mixture of the invention, composed of silicon-containing coupling reagents.

(2) Esterification of a mixture composed of mercaptoorganyl (alkoxysilanes) and, if appropriate, bis(alkoxysilylorganyl) polysulfides with alkylpolyether alcohols of the general formula V in the presence of water. The hydrolyzed or transesterified alkoxy groups of the alkoxysilanes are removed by distillation in the form of alcohol, preferably methanol or ethanol.

(3) Hydrolysis of alkoxy groups in silicon-containing coupling reagents of the general formula (Alkyl-O)$_{3-h}$(Alkyl)$_h$Si—R$^I$—SH or in mixtures composed of silicon-containing coupling reagents of the general formula (Alkyl-O)$_{3-h}$(Alkyl)$_h$ Si—R$^I$—SH and [(Alkyl-O)$_{3-h}$(Alkyl)$_h$Si—R$^I$-]$_2$S$_m$, with h=0 or 1, e.g. by water and/or additive addition. This is followed by transesterification or esterification of the resultant silanol groups or residual alkoxy functions with alkylpolyether alcohols to give the mixtures of the invention, of silicon-containing coupling reagents, optionally with distillative removal of the volatile alcohols liberated, preferably methanol and ethanol, or, respectively, of water.

(4) Hydrolysis of alkoxy groups or alkylpolyether groups in silicon-containing coupling reagents of the general formula II, or in mixtures composed of silicon-containing coupling reagents of the general formula II and IV, to give the mixtures of the invention, of silicon-containing coupling reagents. The hydrolysis takes place by way of example using water, and optionally the addition of additives, and distillative removal of the volatile alcohols released, preferably methanol and ethanol.

(5) Sulfurization of a compound of the general formula (X)(X''')(X''')Si—R$^I$-halogen, by analogy with the process claimed in EP 06110685.2, to give the mixture of the invention, composed of silicon-containing coupling reagents, if appropriate with addition of alkylpolyether alcohols of the general formula V. The sulfurization can, for example, use phase-transfer catalysis in an aqueous environment. The sulfurization can take place by analogy with U.S. Pat. No. 5,840,952 by using hydrogen sulfide and sodium sulfide if appropriate with exclusion of air and/or under pressure.

The substances needed for the physical mixing of the individual constituents or of groups of the constituents to give the mixture of the invention, composed of silicon-containing coupling reagents, can by way of example be synthesized by analogy with EP 1672017, DE 10137809, DE 3426987, DE 102005032658.7, DE 102005052233; DE 102005060122.7, or are commercially available products.

The invention further provides a process for the production of the mixtures of the invention, composed of silicon-containing coupling reagents, characterized in that mercaptoorganyl(alkoxysilanes) are transesterified and hydrolyzed using alkylpolyether alcohols of the general formula V in the presence of water.

The invention further provides a process for the production of the mixtures of the invention, composed of silicon-containing coupling reagents, characterized in that mercaptoorganyl(alkoxysilanes) or a mixture of mercaptoorganyl(alkoxysilanes) is/are partially hydrolyzed by water and/or additive addition, and then, or during the hydrolysis, alkylpolyether alcohols of the general formula V are added, and the substances are reacted to give the mixtures of the invention, of silicon-containing coupling reagents.

The invention further provides a process for the production of the mixtures of the invention, composed of silicon-containing coupling reagents, characterized in that silicon-containing coupling reagents of the general formula II are reacted by water addition and/or additive addition to give the mixtures of the invention, of silicon-containing coupling reagents.

In one specific embodiment, the mixture of the invention can be produced by mixing mercaptoorganyl(alkoxysilanes) with bis(alkoxysilylorganyl) polysulfides and reacting with alkylpolyether alcohols of the general formula V in the presence of water.

The reaction can be carried out in the presence of a catalyst.

The compounds used as catalysts can be metal-containing or free from metal. The compounds that can be used as catalysts can be the catalysts described in EP 1285926 A1.

In one particular embodiment of the reaction, alcoholates of transition group IV of the Periodic Table of the Elements, in particular alcoholates of titanium, e.g. tetra-n-butyl orthotitanate, are used.

Amounts that can be used of these catalysts are from 0.01 to 5% by weight, preferably from 0.01 to 1% by weight, particularly preferably from 0.01 to 0.5% by weight, based on silicon-containing compounds used.

Alkylpolyether alcohols of the general formula V, to which from 0 to 10% by weight of water (based on the amount of silicon-containing compounds used) is added in advance, can be admixed with the reaction mixture at temperatures of from 20 to 150° C., preferably from 50 to 120° C., particularly preferably from 60 to 100° C., and the materials can be reacted at temperatures of from 20 to 200° C., preferably from 50 to 160° C., particularly preferably from 80 to 140° C.

The reaction can be carried out at atmospheric pressure or at reduced pressure.

Alcohols liberated can be removed by distillation after the reaction, or can be removed continuously or batchwise during the course of the reaction.

The conversion in the reaction can be followed via the amount of alcohol removed by distillation. In cases where conversion remains incomplete even after prolonged heating and evacuation, it can be advisable to add another amount of from 0 to 5% by weight of the catalyst (based on the amount of silicon-containing compounds used).

The synthesis of the mixtures of the invention can moreover take place via hydrolysis of the alkoxy groups of a mixture of compounds of the general formula II or of a mixture of silicon-containing coupling reagents of the general formula II and IV. For this, a proportion of from 0 to 10% by weight of water (based on the silicon-containing species used) is admixed with the mixture mentioned and if appropriate a catalyst is added. Catalysts can be the compounds described above, these being metal-containing or free from metal. Catalysts can be compounds of the general formulae $NH_4(OH)$, or $N(Alkyl)H_3(OH)$, $N(Alkyl)_2H_2(OH)$, $N(Alkyl)_3 H(OH)$, or $N(Alkyl)_4(OH)$. Amounts that can be used of these catalysts are from 0 to 5% by weight, preferably from 0.01 to 1% by weight, particularly preferably from 0.01 to 0.5% by weight, based on silicon-containing compounds used.

The reaction mixture can be reacted at temperatures of from 20 to 150° C., preferably from 50 to 120° C., particularly preferably from 60 to 100° C.

The reaction can be carried out at atmospheric pressure or at reduced pressures.

Alcohols liberated can be removed by distillation after the reaction, or can be removed by distillation continuously or batchwise during the course of the reaction.

The invention further provides rubber mixtures, characterized in that they comprise rubber, filler, for example precipitated silica, if appropriate further rubber auxiliaries, and also the mixture of the invention, composed of silicon-containing coupling reagents.

The mixture of the invention, composed of silicon-containing coupling reagents, can be used as coupling agent between inorganic materials (e.g. glass beads, glass fragments, glass surfaces, glass fibers, metals, oxidic fillers, silicas) and organic polymers (e.g. thermosets, thermoplastics, elastomers) or, respectively, as crosslinking agent and surface modifier for oxidic surfaces. The mixture of the invention, composed of silicon-containing coupling reagents, can be used as coupling reagents in filled rubber mixtures, for example for tire treads.

Amounts that can be used of the mixture of the invention, composed of silicon-containing coupling reagents, are from 0.1 to 70% by weight, preferably from 0.1 to 40% by weight, particularly preferably from 1 to 30% by weight, very particularly preferably from 1 to 20% by weight, based on the amount of the rubber used.

The form in which the mixture of the invention, composed of silicon-containing coupling reagents, is added to the mixing process can either be pure form or else a form absorbed onto an inert organic or inorganic carrier, or else a form prereacted with an organic or inorganic carrier. Preferred carrier materials can be precipitated or fumed silicas, waxes, thermoplastics, natural or synthetic silicates, natural or synthetic oxides, preferably aluminum oxide, or carbon blacks. Another form in which the mixture of the invention, composed of silicon-containing coupling reagents, can be added to the mixing process is a form prereacted with the filler to be used.

A form in which the mixture of the invention, composed of silicon-containing coupling reagents, can be added to the mixing process is a form physically mixed with an organic substance or with an organic substance mixture. The organic substance or the organic substance mixture can comprise polymers or oligomers. The polymers or oligomers can be heteroatom-containing polymers or oligomers, e.g. ethylene-vinyl alcohol, ethylene-vinyl acetate, polyvinyl acetate, and/or polyvinyl alcohols. Polymers or oligomers can be saturated or unsaturated elastomers, preferably emulsion SBR or/and solution SBR. The melting point of the blend of the mixture of the invention, composed of silicon-containing coupling reagents, and of organic substance or of an organic substance mixture can be from 50 to 200° C., preferably from 70 to 180° C., particularly preferably from 70 to 150° C., very particularly preferably from 70 to 130° C., extremely preferably from 90 to 110° C. The organic substance or the organic substance mixture can comprise at least one olefinic waxs and/or long-chain carboxylic acid.

The rubber mixture of the invention can also comprise further rubbers, such as natural rubber and/or synthetic rubbers. Preferred synthetic rubbers are described by way of example in W. Hofmann, Kautschuktechnologie [Rubber Technology], Genter Verlag, Stuttgart 1980. Synthetic rubbers that can be used are, inter alia, polybutadiene (BR);
polyisoprene (IR);
styrene-butadiene copolymers (SBR), such as emulsion SBR (E-SBR) or solution SBR (S-SBR). The styrene-butadiene copolymers can have styrene content of from 1 to 60% by weight, preferably from 2 to 50% by weight, particularly preferably from 10 to 40% by weight, very particularly preferably from 15 to 35% by weight;
chloroprene (CR);
isobutylene-isoprene copolymers (IIR);
butadiene-acrylonitrile copolymers whose acrylonitrile contents are from 5 to 60% by weight, preferably from 10 to 50% by weight (NBR), particularly preferably from 10 to 45% by weight (NBR), very particularly preferably from 19 to 45% by weight (NBR);
partially hydrogenated or fully hydrogenated NBR rubber (HNBR);
ethylene-propylene-diene copolymers (EPDM);
abovementioned rubbers which also have functional groups, e.g. carboxy groups, silanol groups or epoxy groups, e.g. epoxidized NR, carboxy-functionalized NBR or silanol- (—SiOH) or silylalkoxy-functionalized (—Si—OR) SBR;

or a mixture of these rubbers.

In one preferred embodiment, the rubbers can be sulfur-vulcanizable.

For the production of car tire treads, it is in particular possible to use anionically polymerized S-SBR rubbers (solution SBR) whose glass transition temperature is above –50° C., or else a mixture of these with diene rubbers. It is particularly preferably possible to use S-SBR rubbers whose butadiene portion has more than 20% by weight vinyl fraction. It is very particularly preferably possible to use S-SBR rubbers whose butadiene portion has more than 50% vinyl fraction.

It is preferably possible to use mixtures of the abovementioned rubbers whose S-SBR fraction is more than 50% by weight, particularly preferably more than 60% by weight.

The following fillers can be used for the rubber mixtures of the invention:

Carbon blacks: The carbon blacks to be used here can be flame blacks, furnace blacks, gas blacks, or thermal blacks. The BET surface areas of the carbon blacks can be from 20 to 200 m$^2$/g. The carbon blacks can also, if appropriate, contain heteroatoms, e.g. Si.

Amorphous silicas, prepared by way of example via precipitation of solutions of silicates (precipitated silicas) or flame hydrolysis of silicon halides (fumed silicas). The specific surface areas of the silicas can be from 5 to 1000 m$^2$/g, preferably from 20 to 400 m$^2$/g (BET surface area) and their primary particle sizes can be from 10 to 400 nm. The silicas can, if appropriate, also take the form of mixed oxides with other metal oxides, such as Al oxides, Mg oxides, Ca oxides, Ba oxides, Zn oxides and titanium oxides.

Synthetic silicates, such as aluminum silicate or alkaline earth metal silicates, such as magnesium silicate or calcium silicate. The BET surface areas of the synthetic silicates can be from 20 to 400 m$^2$/g and their primary particle diameters can be from 10 to 400 nm.

Synthetic or natural aluminum oxides and synthetic or natural aluminum hydroxides.

Natural silicates, such as kaolin and other naturally occurring silicas.

Glass fiber and glass fiber products (mats, strands) or glass microbeads.

Mixtures of these fillers can be used for the rubber mixtures of the invention.

It is preferably possible to use amorphous silicas prepared by precipitation of solutions of silicates (precipitated silicas) with BET surface areas of from 20 to 400 m$^2$/g, particularly preferably 100 m$^2$/g to 250 m$^2$/g. The amounts that can be used of the amorphous silicas are from 5 to 150 parts by weight, based in each case on 100 parts of rubber.

The fillers mentioned can be used alone or in a mixture.

In one particularly preferred embodiment, the rubber mixtures can comprise from 10 to 150 parts by weight of pale-colored fillers, such as silicas if appropriate together with from 0 to 100 parts by weight of carbon black, and also from 0.1 to 70 parts by weight, preferably from 0.1 to 40 parts by weight, particularly preferably from 1 to 30 parts by weight, extremely preferably from 1 to 20 parts by weight, of the mixture of the invention, composed of silicon-containing coupling reagents, based in each case on 100 parts by weight of rubber.

The rubber mixtures can also comprise silicone oil and/or alkylsiliane.

The rubber mixtures of the invention can comprise other known rubber auxiliaries, e.g. crosslinking agents, vulcanization accelerators, reaction accelerators, reaction retarders, antioxidants, stabilizers, processing aids, platicizers, waxes, or metal oxides, and also if appropriate activators, such as triethanolamine or hexanetriol.

Other rubber auxiliaries can be: polyethylene glycol or/and polypropylene glycol or/and polybutylene glycol with molar masses from 50 to 50 000 g/mol, preferably from 50 to 20 000 g/mol, particularly preferably from 200 to 10 000 g/mol, very particularly preferably from 400 to 6000 g/mol, extremely preferably from 500 to 3000 g/mol, neopentyl glycol HO—CH$_2$—C(Me)$_2$-CH$_2$—OH, pentaerythritol C(CH$_2$—OH)$_4$ or trimethylolpropane CH$_3$—CH$_2$—C(CH$_2$OH)$_3$ etherified with polyethylene glycol, etherified with polypropylene glycol, etherified with polybutylene glycol, or etherified with a mixture thereof, where the number of repeat units of ethylene glycol, propylene glycol or/and butylene glycol in the etherified polyalcohols can be from 2 to 100, preferably from 2 to 50, particularly preferably from 3 to 30, very particularly preferably from 3 to 15.

Amounts that can be used of the rubber auxiliaries are conventional, depending inter alia on the intended use. Examples of conventional amounts can be amounts of from 0.1 to 50% by weight, based on rubber.

Crosslinking agents that can be used are sulfur or organic sulfur donors.

The rubber mixtures of the invention can comprise further vulcanization accelerators. Examples of suitable vulcanization accelerators that can be used are mercapto-benzothiazoles, sulfenamides, guanidines, dithiocarbamates, thioureas, thiocarbonates, and also their zinc salts, e.g. zinc dibutyldithiocarbamate.

Amounts that can be used of the vulcanization accelerators and sulfur are from 0.1 to 10% by weight, preferably from 0.1 to 5% by weight, based on the rubber used.

The invention also provides a process for the production of the inventive rubber mixtures, characterized in that at least one rubber, at least one filler, and the mixture of the invention, composed of silicon-containing coupling reagents, are mixed.

Addition of the mixture of the invention, composed of silicon-containing coupling reagents, and also the addition of the fillers, can take place when the temperature of the composition is from 100 to 200° C. However, it can also take place at lower temperatures of from 40 to 100° C., for example together with further rubber auxiliaries.

The blending of the rubbers with the filler and, if appropriate, with rubber auxiliaries and with the mixture of the invention, composed of silicon-containing coupling reagent can take place in or on conventional mixing assemblies, such as rolls, internal mixers, and mixing extruders. These rubber mixtures can usually be produced in internal mixers, beginning with one or more successive thermomechanical mixing stages in which the rubbers, the filler, the mixture of the invention, composed of silicon-containing coupling reagents, and the rubber auxiliaries are incorporated by mixing at from 100 to 170° C. The sequence of addition and the juncture of addition of the individual components here can have a decisive effect on the resultant properties of the mixture. The crosslinking chemicals can usually be admixed in an internal mixer or on a roll at from 40 to 110° C. with the rubber mixture thus obtained, and processed to give what is known as a crude mixture for the subsequent steps of the process, for example shaping and vulcanization.

Vulcanization of the rubber mixtures of the invention can take place at temperatures of from 80 to 200° C., preferably from 130 to 180° C., if appropriate under a pressure of from 10 to 200 bar.

The rubber mixtures of the invention can be used for the production of moldings, for example for the production of tires, including pneumatic tires, tire treads, cable sheathing, hoses, drive belts, conveyor belts, roll coverings, shoe soles, and sealing elements, e.g. ring seals, and damping elements.

The invention further provides moldings obtainable from the rubber mixture of the invention, by vulcanization.

The rubber mixtures of the invention have the advantage that alcohol emission during the mixing process has been reduced, while at the same time processing properties are at least identical, and/or dynamic properties are at least identical, when comparison is made with known mixtures.

EXAMPLES

The raw materials used are commercially available or are produced in accordance with known specifications.

The ethoxylated alcohols are products marketed by BASF (Lutensol TO 5 and Lutensol ON 50), Sasol (Marlipal 013/50), and Schärer & Schläpfer (Aduxol Hex 05B, Aduxol ST 04, Aduxol ST 05, and Aduxol LH-05). C1E3 Alcohol can be purchased as item number 8.14587.0250 from Merck. Titanium tetrabutoxide, THF, $NH_3$ solution, and $MgSO_4$ are purchased from Merck. 3-Mercaptopropyltriethoxysilane is a product of Degussa GmbH, and can be purchased with tradename VP Si 263.

XP S±363 variants are obtained in accordance with known specifications from the respective ethoxylated alcohol, as described by way of example in patent application DE 102005057801.2. VP Si 363 is a product marketed by Degussa GmbH.

The mixtures of the invention, containing silanol groups, can be separated and characterized by the conventional physical and chemical methods. In particular, HPLC, GC, and GPC can be used for separation, and $^1$H NMR, $^{13}$C NMR, and $^{29}$Si NMR spectroscopy, IR spectroscopy, or else mass spectrometry, can be used for their characterization. The accurate masses of the compounds of the general formula I are shown by APCIMS spectra recorded by methods known to the person skilled in the art under anhydrous conditions and with addition of $NH_4^+$ salts, in positive and negative load.

Silanol-containing species and species free from silanol can be distinguished by virtue of different shifts of the attendant O and/or Si atoms in X-ray photoelectron spectra measured with very high spectrometer resolution. Gaussian or Lorentzian line-shape analysis of the X-ray photoelectron spectra obtained can permit quantification of the silanol-containing species.

X-ray photoelectron spectra can be obtained by the methods known to the person skilled in the art (D. Briggs and M. P. Seah (Eds.) "Practical Surface Analysis", 2nd edn., Vol. 1 "Auger- and X-ray Photoelectron Spectroscopy", Wiley & Sons Chichester, Salle+Sauerländer Aarau, 1990).

$^{29}$Si NMR spectra and $^{13}$C NMR spectra can be recorded by methods known to the person skilled in the art. $^{29}$Si NMR spectra exhibit signals for monomeric silane species in the range from −44 to −45 ppm, signals of silane-M structures from −52 to −54, and signals of the species having a higher level of oligomerization starting at −57 ppm.

$^{13}$C NMR spectra exhibit signals belonging to bonded alkylpolyether alcohol moieties around 62 ppm, signals belonging to unbonded alkylpolyether alcohols of the general formula V around 61 ppm, signals belonging to bonded EtOH moieties around 58 ppm, and signals belonging to unbonded EtOH around 57 ppm.

The integrals of these $^{29}$Si NMR signals and $^{13}$C NMR signals can be used to calculate the content of free silanol groups, the ratio by weight of species containing silanol groups to species free from silanol groups, and also the proportion by weight of free alkylpolyether alcohol.

The proportion of polysulfidic organo(alkylpolyethersilanes) can be determined by dissolving the product mixture in acetonitrile and derivatizing it with DTNB (5,5'-dithiobis(2-nitrobenzoic acid)) with addition of $NEt_3$. Absorption at wavelength 480 nm of a $7*10^{-5}$ M solution of this derivative correlates linearly with the content of free SH groups. The amount of polysulfidic organo(alkylpolyethersilanes) is found by taking the difference from 100.

General Operating Specifications:

Unless otherwise stated, the silanol-containing specimens are produced in accordance with one of the following general operating specifications.

A: The silane is dissolved (c=0.4 mol/L) in THF in a round-bottomed flask with reflux condenser and dropping funnel. 4% (% by v, based on THF) of 25% aqueous $NH_3$ are added dropwise to this mixture, and the resultant solution is heated to boiling for 2 h. After cooling to RT, the phases are separated if appropriate, and the organic phase is dried over $MgSO_4$. Removal of the solvent in vacuo gives the silanol-containing product.

B: 2 equivalents of the ethoxylated alcohol, 1 equivalent of 3-mercaptopropyltriethoxysilane, and 0.05% by weight of $Ti(On-Bu)_4$ (based on silane) are mixed in a round-bottomed flask with distillation bridge, and the mixture is heated up to 140° C. The resultant EtOH is removed by distillation by continuous lowering of the pressure after 1 h of reaction time at 140° C. The silanol-containing product is obtained as bottom product.

C: The stated amount of silane is dissolved in the stated amount of THF in a round-bottomed flask with reflux condenser and dropping funnel. 25% aqueous $NH_3$ are added dropwise to this mixture, and the resultant solution is heated to boiling for the stated time. After cooling to about 50° C., the mixture is neutralized with saturated aqueous $KH_2PO_4$ solution, filtered at RT, and dried over $MgSO_4$. Removal of the solvent in vacuo gives the silanol-containing product.

Example 1

59.5 g of 3-mercaptopropyl(triethoxysilane) (0.25 mol) are used as initial charge under $N_2$ as inert gas in a 500 ml flask with stirrer, thermometer, and distillation bridge. 210 g of Lutensol TO 5 (0.5 mol), to which 3% by weight of water (based on the silane) has previously been added, are added to this mixture. The reaction mixture is vigorously stirred for some minutes, and then 0.05% by weight of titanium tetrabutoxide (based on the silane used) is added, with stirring. The mixture is then heated to 80° C. for 1 h, and then to 140° C. for 1 h. After this time, the pressure is slowly lowered down to 50 mbar, and ethanol produced is removed by distillation. After a reaction time of 7 h, the mixture is cooled and depressurized, and a further 0.05% by weight of titanium tetrabutoxide (based on the silane used) is added. The mixture is again heated to 140° C. and the pressure is slowly reduced down to 50 mbar. This gives 245 g of a colorless, slightly cloudy liquid.

Example 2

59.5 g of 3-mercaptopropyl(triethoxysilane) (0.25 mol) are used as initial charge under $N_2$ as inert gas in a 500 ml flask with stirrer, thermometer, and distillation bridge. 210 g of Lutensol TO 5 (0.5 mol), to which 6% by weight of water (based on the silane) has previously been added, are added to this mixture.

The reaction mixture is vigorously stirred for some minutes, and then 0.05% by weight of titanium tetrabutoxide (based on the silane used) is added, with stirring. The mixture is then heated to 80° C. for 1 h, and then to 140° C. for 1 h. After this time, the pressure is slowly lowered down to 50 mbar, and ethanol produced is removed by distillation. After a reaction time of 7 h, the mixture is cooled and depressurized, and a further 0.05% (w/w) of titanium tetrabutoxide (based on the silane used) is added. The mixture is again heated to 140° C. and the pressure is slowly reduced down to 50 mbar. This gives 235 g of a colorless, slightly cloudy liquid.

Table 1 shows the composition of examples 1 and 2 determined by $^1H$ NMR, $^{13}C$ NMR, and $^{29}Si$ NMR.

TABLE 1

| Example | Alkylpolyether alcohol | (Mercaptoorganyl)-alkylpolyether-silanes containing silanol groups | (Mercaptoorganyl)-alkylpolyether-silanes free from silanol groups | Free alkylpoly-ether alcohol | Polysulfidic organo(alkyl-polyethersilanes) free from silanol groups |
|---|---|---|---|---|---|
| Determination by | | $^{29}Si$ NMR | $^{29}Si$ NMR | $^{13}C$ NMR | $^1H$ NMR |
| | | % by weight of mixture of the invention | % by weight of mixture of the invention | % by weight, in relation to column 3 + 4 | % by weight, in relation to column 3 + 4 |
| 1 | Lutensol TO 5 | 14 | 86 | 1 | 0.2 |
| 2 | Lutensol TO 5 | 27 | 73 | 4 | 0.2 |

Example 3

Vulcanizate Testing

The mixing specifications used for the rubber mixtures is stated in table 2 below. The unit phr here means proportions by weight based on 100 parts of the crude rubber used. Equimolar amounts were used of the organosilicon compounds, i.e. an identical molar amount was used.

The general process for the production of rubber mixtures and their vulcanizates is described in the book: "Rubber Technology Handbook", W. Hofmann, Hanser Verlag 1994.

TABLE 2

| | Mixture 1 Comparative example [phr] | Mixture 2 Example 1 [phr] | Mixture 3 Example 2 [phr] |
|---|---|---|---|
| 1st stage | | | |
| Buna VSL 5025-1 | 96 | 96 | 96 |
| Buna CB 24 | 30 | 30 | 30 |
| Ultrasil 7000 GR | 80 | 80 | 80 |
| VP Si 363 | 10 | — | — |
| Example 1 | — | 9.7 | — |
| Example 2 | — | — | 9.7 |
| ZnO | 3 | 3 | 3 |
| Stearic acid | 2 | 2 | 2 |
| Naftolen ZD | 10 | 10 | 10 |
| Vulkanox 4020 | 1.5 | 1.5 | 1.5 |
| Protektor G 3108 | 1 | 1 | 1 |
| 2nd stage | | | |
| Stage 1 batch | | | |
| 3rd stage | | | |
| Stage 2 batch | | | |
| Vulkacit D | 0.25 | 0.25 | 0.25 |
| Vulkacit CZ | 1.5 | 1.5 | 1.5 |
| Perkacit TBzTD | 0.5 | 0.5 | 0.5 |
| Sulfur | 2.2 | 2.2 | 2.2 |

VSL 5025-1 polymer is a solution-polymerized SBR copolymer from Bayer AG, having styrene content of 25% by weight and butadiene content of 75% by weight. The copolymer comprises 37.5 phr of oil and its Mooney viscosity (ML 1+4/100° C.) is 50.

Buna CB 24 polymer is a cis-1,4-polybutadiene (neodymium type) from Bayer AG, having cis-1,4 content of at least 96%, its Mooney viscosity being 44±5.

Ultrasil 7000 GR is a readily dispersible silica from Degussa AG, its BET surface area being 170 m²/g.

Naftolen ZD from Chemetall is used as aromatic oil, and Vulkanox 4020 is PPD from Bayer AG, and Protektor G3108 is an ozone-protection wax from Paramelt B. V. Vulkacit C Z (CBS) and Vulkacit D (DPG) are commercially available products from Bayer AG. Perkacit TBzTD (tetrabenzylthiuram tetrasulfide) is a product from Flexsys N.V.

The rubber mixtures are produced in an internal mixer in accordance with the mixing specification in table 3.

TABLE 3

| Stage 1 | |
|---|---|
| Settings | |
| Mixing assembly | Werner & Pfleiderer type E |
| Rotation rate | 70 min$^{-1}$ |
| Ram pressure | 5.5 bar |
| Capacity | 1.58 L |
| Fill level | 0.56 |
| Chamber temp. | 70° C. |
| Mixing procedure | |
| 0 to 1 min | Buna VSL 5025-1 + Buna CB 24 |
| 1 to 2 min | ½ silica, ZnO, stearic acid, Naftolen ZD, coupling agent |
| 2 to 4 min | ½ silica, Vulkanox, Protektor |
| 4 min | Purge |
| 4 to 5 min | Mix |
| 5 min | Aerate |
| 5 to 6 min | Mix and discharge |
| Batch temp. | 140-150° C. |
| Storage | 24 h at room temperature |
| Stage 2 | |
| Settings | |
| Mixing assembly | As in stage 1, except: |
| Rotation rate | 60 min$^{-1}$ |
| Chamber temp. | 80° C. |
| Fill level | 0.54 |
| Mixing procedure | |
| 0 to 2 min | Break up stage 1 batch |
| 2 to 5 min | Maintain 145° C. batch temperature via rotation rate variation |
| 5 min | Discharge |
| Batch temp. | 140-150° C. |
| Storage | 4 h at room temperature |
| Stage 3 | |
| Settings | |
| Mixing assembly | As in stage 1, except: |
| Rotation rate | 40 min$^{-1}$ |
| Fill level | 0.52 |
| Chamber temp. | 50° C. |
| Mixing procedure | |
| 0 to 2 min | Stage 2 batch, accelerator, sulfur |
| 2 min | Discharge and form sheet on laboratory mixing rolls (diameter 200 mm, length 450 mm, chamber temperature 50° C.) Homogenize: Cut the material 5 times towards the left and 5 times towards the right and 6 times with wide nip (6 mm) and 3 times with narrow nip (3 mm), and peel milled sheet away. |
| Batch-Temp. | <110° C. |

Table 4 collates the methods for rubber testing.

TABLE 4

| Physical testing | Standard/conditions |
|---|---|
| ML 1 + 4, 100° C., 3$^{rd}$ stage | DIN 53523/3, ISO 667 |
| Vulcameter test, 165° C. | DIN 53529/3, ISO 6502 |
| Dmax – Dmin (dNm) | |
| Ring tensile test, 23° C. | DIN 53504, ISO 37 |
| Tensile strength (MPa) | |
| Elongation at break (%) | |
| Shore A hardness, 23° C. (SH) | DIN 53 505 |
| Ball Rebound, 60° C. (%) | ASTM D5308 |

Table 5 shows the results of vulcanizate testing. The mixtures were vulcanized at 165° C. for 10 min.

TABLE 5

| | Unit | Mixture 1 (comparative example) | Mixture 2 Example 1 | Mixture 3 Example 2 |
|---|---|---|---|---|
| Crude mixture data | | | | |
| ML 1 + 4, 3rd stage | [—] | 61 | 60 | 59 |
| Dmax – Dmin | [dNm] | 14.4 | 14.9 | 15.0 |
| Vulcanizate data | | | | |
| Tensile strength | [MPa] | 13.1 | 13.5 | 13.4 |
| Elongation at break | [%] | 310 | 325 | 330 |

As can be discerned from the data in table 5, a feature of the mixtures using the mixtures of the invention, of examples 1 and 2, is that the Mooney viscosity of the crude mixtures is lower. The mixtures using the mixtures of the invention also have higher Dmax-Dmin and higher tensile strengths, attributable to a higher level of reinforcement. Since mixtures 2 and 3 at the same time have higher tensile strain at break values, they have advantageous tensile strain behavior.

Example 4

33.2 g of XP Si 363 (C1E1-3) are reacted in accordance with general operating specification A. This gives 39.8 g of product whose silanol fraction is 5%.

Example 5

47.8 g of XP Si 363 (C1E1-2) are reacted in accordance with general operating specification A. This gives 56 g of product whose silanol fraction is 11%.

Example 6

189.9 g of XP Si 363 (C1E3-2) are dissolved in 250 mL of THF, and 3 mL of 25% aqueous $NH_3$ are admixed, and the mixture is then reacted as described in general operating specification A. This gives 187.1 g of product whose silanol fraction is 1%.

Example 7

630 g of Aduxol Hex 05B (1.8 mol) are reacted with 3-mercaptopropyltriethoxysilane in accordance with general operating specification B. This gives 707.2 g of product whose silanol fraction is 10%.

Example 8

268 g of Lutensol ON 50 (0.7 mol) are reacted with 3-mercaptopropyltriethoxysilane in accordance with general operating specification B. 5% by weight of water (based on 3-mercaptopropyltriethoxysilane) are added. This gives 329.1 g of product whose silanol fraction is 4%.

Example 9

327.1 g of Lutensol ON 50 (0.86 mol) are reacted with 3-mercaptopropyltriethoxysilane in accordance with general operating specification B. This gives 374.7 g of product whose silanol fraction is 26%.

Example 10

132.1 g of XP Si 363 (C12E5-3) are reacted in accordance with general operating specification A. This gives 132.9 g of product whose silanol fraction is 44%.

Example 11

106.1 g of Lutensol TO 5, 3.6 g of water, and 29.8 mg of $Ti(O-nBu)_4$ are admixed with 59.6 g of 3-mercaptopropyltri-ethoxysilane in a 500 mL flask with distillation bridge. The reaction mixture is heated to 140° C., and EtOH produced is removed by distillation. This gives 143.2 g of product whose silanol fraction is 23%.

Beispiel 12

99.8 g of VP Si 363 (C13E5-2) (0.1 mol) in 250 mL of THF are reacted with 1 mL of 25% aqueous $NH_3$ for 1 h in accordance with general operating specification C. This gives 88 g of product whose silanol fraction is 6%.

Example 13

100.3 g of VP Si 363 (C13E5-2) (0.1 mol) in 250 mL of THF are reacted with 10 mL of 25% aqueous $NH_3$ for 2 h in accordance with general operating specification C. This gives 81.4 g of product whose silanol fraction is 28%.

Example 14

136.2 g of XP Si 363 (C13E5-3) are reacted in accordance with general operating specification A. This gives 137.4 g of product whose silanol fraction is 58%.

Example 15

104 g of XP Si 363 (C18E4-2) are reacted in accordance with general operating specification A. This gives 104.2 g of product whose silanol fraction is 21%.

Example 16

103.9 g of XP Si 363 (C18E4-2) are reacted in accordance with general operating specification A. This gives 102.7 g of product whose silanol fraction is 24%.

Example 17

100.2 g of XP Si 363 (C18E5-2) (0.1 mol) in 350 mL of THF are reacted with 10 mL of 25% aqueous $NH_3$ for 2 h in accordance with general operating specification C. This gives 96.3 g of product whose silanol fraction is 14%.

Example 18

Table 2 states the mixing specification used for the rubber mixtures, the only variations being the compounds of the invention and their amounts. VP Si 363 is used as comparative example.

In the case of the compounds of the invention, either the same amount is added or both the molar mass and the analytical results from table 6 are taken into consideration in order that an equal number of species capable of coupling is present in the rubber mixtures (table 7).

TABLE 6

| Example | Alkylpolyether alcohol | Alcohol component CxEv | % by weight of free alkylpoly-ether | % by weight of polysulfidic organo(alkylpoly-ethersilanes) | Ratio by weight of silanol-containing species to species free from silanol |
|---|---|---|---|---|---|
| 4 | XP Si 363 C1E1 | C1E1 | 2 | nd | 14:86 |
| 5 | XP Si 363 C1E3 | C1E3 | 9 | nd | 11:89 |
| 6 | XP Si 363 C1E3 | C1E3 | 2 | — | 1:99 |
| 7 | Aduxol Hex 05B | C8E5 | 5 | nd | 31:69 |
| 8 | Lutensol ON 50 | C10E5 | 22 | — | 12:88 |
| 9 | Lutensol ON 50 | C10E5 | 8 | 8 | 70:30 |
| 10 | Aduxol LH-05 | C12E5 | 22 | 11 | 100:0 |
| 11 | Lutensol TO 5 | C13E5 | 0 | — | 62:38 |
| 12 | Lutensol TO 5 + Marlipal O13/50 (1:1) | C13E5 | 3 | 2 | 13:87 |
| 13 | Lutensol TO 5 + Marlipal O13/50 (1:1) | C13E5 | 14 | 2 | 79:21 |
| 14 | Lutensol TO 5 | C13E5 | 21 | 11 | 100:0 |
| 15 | Aduxol ST 04 | C18E4 | 10 | — | 61:39 |
| 16 | Aduxol ST 04 | C18E4 | 14 | — | 69:31 |
| 17 | Aduxol ST 05 | C18E5 | 6 | — | 37:63 |

"nd": not determinable,
"—": not determined
CxEv: Number x of carbon atoms in the Alk alkyl chain, number v of ethylene oxide units

TABLE 7

| Example | Amount added in phr (per hundred rubber) |
|---|---|
| Comparative example VP Si 363 | 10 |
| 13 | 10 |
| 12 | 10 |
| 15 | 12.1 |
| 5 | 7.1 |
| 17 | 13.4 |
| 16 | 12.6 |

TABLE 7-continued

| Example | Amount added in phr (per hundred rubber) |
|---|---|
| 14 | 9.7 |
| 10 | 12.9 |
| 9 | 10.6 |

The rubber mixtures were produced in an internal mixer in accordance with the mixing specification in table 3.

Table 4 collates the methods for rubber testing.

Table 8 shows the results of vulcanizate testing for examples 12 and 13. Mixture 4 is vulcanized for 20 min, and mixtures 5 and 6 are vulcanized for 15 min, at 165° C.

TABLE 8

| | Unit | Mixture 4 (comparative example) | Mixture 5 Example 13 | Mixture 6 Example 12 |
|---|---|---|---|---|
| Crude mixture data | | | | |
| ML 1 + 4, 3rd stage | [—] | 59 | 59 | 59 |
| Dmax – Dmin | [dNm] | 13.4 | 13.4 | 13.4 |
| Vulcanizate data | | | | |
| Tensile strength | [MPa] | 13.2 | 12.2 | 12.3 |
| Elongation at break | [%] | 335 | 325 | 320 |

TABLE 8-continued

| | Unit | Mixture 4 (comparative example) | Mixture 5 Example 13 | Mixture 6 Example 12 |
|---|---|---|---|---|
| Shore A hardness | [—] | 56 | 56 | 57 |
| Ball rebound | [%] | 73.2 | 73.3 | 73.9 |

As can be discerned from table 8, the Mooney viscosities of the rubber mixtures are identical. The same applies to the Dmax-Dmin value.

The ball rebound data for mixtures 5 and 6 are slightly higher when compared with the comparative example (mixture 4).

Table 9 shows the results of vulcanizate testing for examples 5 and 15. Mixture 7 is vulcanized for 20 min, and mixtures 8 and 9 are vulcanized for 10 min, at 165° C.

TABLE 9

| | Unit | Mixture 7 (comparative example) | Mixture 8 Example 15 | Mixture 9 Example 5 |
|---|---|---|---|---|
| Crude mixture data | | | | |
| ML 1 + 4, 3rd stage | [—] | 62 | 60 | 60 |
| Dmax – Dmin | [dNm] | 15.5 | 12.9 | 14.9 |
| Vulcanizate data | | | | |
| Tensile strength | [MPa] | 12.3 | 13.8 | 13.1 |
| Elongation at break | [%] | 325 | 360 | 325 |
| Shore A hardness | [—] | 59 | 56 | 58 |
| Ball rebound | [%] | 73.7 | 73.8 | 73.1 |

Mixtures 8 and 9 exhibit lower Mooney viscosity, when compared with comparative mixture 7.

Shore A hardness and elongation at break of the vulcanized rubber mixtures are also comparable.

Table 10 shows the results of vulcanizate testing for examples 9, 10, 14, 16, and 17. Mixture 10 is vulcanized for 20 min, and mixtures 11-15 are vulcanized for 10 min, at 165° C.

As can be discerned from table 10, all of the mixtures other than mixture 11 have lower viscosities than the comparative mixture. Mixture 11 has higher ball rebound than the comparative mixture.

TABLE 10

| | Unit | Mixture 10 (comparative example) | Mixture 11 Example 17 | Mixture 12 Example 16 | Mixture 13 Example 14 | Mixture 14 Example 10 | Mixture 15 Example 9 |
|---|---|---|---|---|---|---|---|
| Crude mixtung data | | | | | | | |
| ML 1 + 4, 2nd stage | [—] | 73 | 76 | 72 | 72 | 73 | 76 |
| ML 1 + 4, 3rd stage | [—] | 60 | 62 | 58 | 58 | 58 | 59 |
| Dmax-Dmin | [dNm] | 14.3 | 12.5 | 12.3 | 16.9 | 13.8 | 13.8 |
| Vulcanizate data | | | | | | | |
| Tensile strength | [MPa] | 13.9 | 11.2 | 9.6 | 11.8 | 8.4 | 12.4 |
| Elongation at break | [%] | 350 | 290 | 295 | 360 | 270 | 320 |
| Shore A hardness | [—] | 58 | 57 | 56 | 62 | 57 | 59 |
| Ball rebound | [%] | 74.3 | 75.6 | 76.2 | 73.0 | 74.7 | 73.5 |

What is claimed is:

1. A mixture composed of silicon-containing coupling reagents, wherein the mixture comprises both, (mercaptoorganyl)alkylpolyethersilanes containing silanol groups and (mercaptoorganyl)alkylpolyethersilanes free from silanol groups, in a ratio by weight of from 13:87 to 79:21, wherein the (mercaptoorganyl)alkylpolyethersilanes containing silanol groups are compounds of the general formula I $$(X)(X')(X'')Si-R^I-SH \qquad I,$$

where, independently of one another,

X is 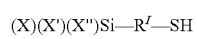,

X' is branched or unbranched alkyl, branched or unbranched alkoxy, a branched or unbranched $C_2$-$C_{25}$—alkenyloxy group, an alkylpolyether group , where v=1-40, w=1-40, or a hydroxy group (—OH), $R^{II}$, independently of one another, is H, or an unbranched or branched alkyl group, Alk is a branched or unbranched, saturated or unsaturated, substituted or unsubstituted, aliphatic, monovalent $C_1$-$C_{35}$-hydrocarbon group, X" is a hydroxy group (—OH), and $R^I$ is a branched or unbranched, saturated or unsaturated, aliphatic, divalent $C_1$-$C_{30}$-hydrocarbon group, optionally having substitution, and wherein the (mercaptoorganyl)alkylpolyethersilanes free from silanol groups are compounds of the general formula II, $$(X)(X''')(X''')Si—R^I—SH \qquad II$$

where, independently of one another,

X and $R^I$ are defined as above, and

X''', independently of one another, is branched or unbranched alkyl, branched or unbranched alkoxy, a branched or unbranched $C_2$-$C_{25}$-alkenyloxy group, or the alkylpolyether group O—$((CR^{II}_2)_w$—O—$)_v$Alk, are reacted via water addition and/or additive addition.

2. The mixture composed of silicon-containing coupling reagents, as claimed in claim 1, wherein it has been absorbed onto an inert organic or inorganic carrier or has been mixed with the same, or has been prereacted with an organic or inorganic carrier.

3. The mixture composed of silicon-containing coupling reagents, as claimed in claim 1, wherein it comprises from 0.01 to 50% by weight of polysulfidic organo(alkylpolyethersilanes) containing silanol groups, based on the total weight of the (mercaptoorganyl)alkylpolyethersilanes containing silanol groups and free from silanol groups.

4. The mixture composed of silicon-containing coupling reagents, as claimed in claim 1, wherein it comprises from 0.1 to 50% by weight of polysulfidic organo(alkylpolyethersilanes) free from silanol groups, based on the total weight of the (mercaptoorganyl)alkylpolyethersilanes containing silanol groups and free from silanol groups.

5. The mixture composed of silicon-containing coupling reagents, as claimed in claim 1, wherein it comprises from 0.1 to 50% by weight of alkylpolyether alcohols, based on the total weight of the (mercaptoorganyl)alkylpolyethersilanes containing silanol groups and free from silanol groups.

6. A rubber mixture, wherein it comprises rubber, filler, if appropriate further rubber auxiliaries, and also mixtures composed of silicon-containing coupling reagents, as claimed in claim 1.

7. The use of rubber mixtures as claimed in claim 6 for the production of moldings.

8. The use of rubber mixtures as claimed in claim 6 for the production of tires, including pneumatic tires, rubber-containing tire constituents, tire treads, cable sheathing, hoses, drive belts, conveyor belts, roll coverings, shoe soles, ring seals, and damping elements.

9. A tire tread, wherein it comprises a rubber mixture as claimed in claim 6.

10. A process for the preparation of the mixtures composed of silicon-containing coupling reagents, as claimed in claim 1, wherein mercaptoorganyl(alkoxysilanes) are transesterified and hydrolyzed using alkylpolyether alcohols of the general formula V, $$HO—((CR^{II}_2)_w—O—)_v Alk \qquad V$$

where $R^{II}$, independently of one another, is H, or an unbranched or branched alkyl group, Alk is a branched or unbranched, saturated or unsaturated, substituted or unsubstituted, aliphatic, aromatic, or mixed aliphatic/aromatic monovalent $C_1$-$C_{35}$-hydrocarbon group, v=1-40, and w=1-40, in the presence of water.

11. A process for the preparation of the mixtures composed of silicon-containing coupling reagents, as claimed in claim 1, wherein mercaptoorganyl(alkoxysilanes) or mixtures of mercaptoorganyl (alkoxysilanes) are partially hydrolyzed by water and/or additive addition, and then, or during the hydrolysis, alkylpolyether alcohols of the general formula V, $$HO—((CR^{II}_2)_w—O—)_v Alk \qquad V$$

where $R^{II}$, independently of one another, is H, or an unbranched or branched alkyl group, Alk is a branched or unbranched, saturated or unsaturated, substituted or unsubstituted, aliphatic, aromatic, or mixed aliphatic/aromatic monovalent $C_1$-$C_{35}$-hydrocarbon group, v=1-40, and w=1-40, are added and reacted.

12. A process for the preparation of the mixtures composed of silicon-containing coupling reagents, as claimed in claim 1, wherein silicon-containing coupling reagents of the general formula II, $$(X)(X''')(X''')Si—R^I—SH \qquad II$$

where, independently of one another,

X''', independently of one another, is branched or unbranched alkyl, branched or unbranched alkoxy, a branched or unbranched $C_2$-$C_{25}$-alkenyloxy group, or the alkylpolyether group O—$((CR^{II}_2)_w$—O—$)_v$Alk, are reacted via water addition and/or additive addition.

* * * * *